US010729562B2

(12) United States Patent
Knapp et al.

(10) Patent No.: US 10,729,562 B2
(45) Date of Patent: **\*Aug. 4, 2020**

(54) BONE FUSION SYSTEM, DEVICE AND METHOD INCLUDING A MEASURING MECHANISM

(71) Applicant: Neuropro Technologies, Inc., Modesto, CA (US)

(72) Inventors: Troy D. Knapp, Glenwood City, WI (US); Gregory C. Stalcup, Fort Wayne, IN (US); Kreigh R. Williams, Fort Wayne, IN (US); Steven E. Dietzel, Peru, IN (US)

(73) Assignee: Neuropro Technologies, Inc., Modesto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/121,301

(22) Filed: Sep. 4, 2018

(65) Prior Publication Data

US 2019/0008658 A1    Jan. 10, 2019

Related U.S. Application Data

(63) Continuation of application No. 15/409,407, filed on Jan. 18, 2017, now Pat. No. 10,111,760.

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/447* (2013.01); *A61F 2/4657* (2013.01); *A61F 2/4603* (2013.01);

(Continued)

(58) Field of Classification Search
CPC .................. A61F 2/4611; A61F 2/4657; A61F 2002/4659–4661

See application file for complete search history.

(56) References Cited

U.S. PATENT DOCUMENTS 4,309,777 A    1/1982  Patil
4,388,921 A *  6/1983  Sutter ............... A61B 17/8047
                                              411/537

(Continued)

FOREIGN PATENT DOCUMENTS

CN    102429805 A    5/2015
DE    29911382       8/1999

(Continued)

OTHER PUBLICATIONS

Search Report from European Application No. EP13797446.

(Continued)

*Primary Examiner* — Jacqueline T Johanas
*Assistant Examiner* — Michelle C Eckman
(74) *Attorney, Agent, or Firm* — Haverstock & Owens LLP

(57) ABSTRACT

A bone fusion method, system and device for insertion between bones that are to be fused together and/or in place of one or more of the bones, such as, for example, the vertebrae of a spinal column. The bone fusion device comprises one or more extendable tabs having a central rib. The bone fusion device includes one or more support channels configured to receive an insertion instrument that is then secured to the bone fusion device via a coupling mechanism. As a result, the coupled device is able to be securely positioned between vertebrae using the insertion instrument with minimal risk of slippage.

28 Claims, 28 Drawing Sheets

(52) U.S. Cl.
CPC .............. *A61F 2002/30131* (2013.01); *A61F 2002/30153* (2013.01); *A61F 2002/30411* (2013.01); *A61F 2002/30507* (2013.01); *A61F 2002/30515* (2013.01); *A61F 2002/30523* (2013.01); *A61F 2002/30556* (2013.01); *A61F 2002/30593* (2013.01); *A61F 2002/4622* (2013.01); *A61F 2002/4627* (2013.01); *A61F 2002/4628* (2013.01); *A61F 2002/4635* (2013.01); *A61F 2002/4658* (2013.01); *A61F 2250/0009* (2013.01)

(56) References Cited

U.S. PATENT DOCUMENTS

| | | |
|---|---|---|
| 4,863,476 A | 9/1989 | Shepperd |
| 4,961,740 A | 10/1990 | Ray et al. |
| 5,015,247 A | 5/1991 | Michelson |
| 5,059,193 A | 10/1991 | Kuslich |
| 5,123,926 A | 6/1992 | Pisharodi |
| 5,171,278 A | 12/1992 | Pisharodi |
| 5,443,514 A | 8/1995 | Steffee |
| 5,458,642 A | 10/1995 | Beer et al. |
| 5,489,307 A | 2/1996 | Kuslich et al. |
| 5,522,899 A | 6/1996 | Michelson |
| 5,653,763 A | 8/1997 | Allen |
| 5,658,335 A | 8/1997 | Allen |
| 5,665,122 A | 8/1997 | Kambin |
| 5,693,100 A | 12/1997 | Pisharodi |
| 5,702,391 A | 12/1997 | Lin |
| 5,716,415 A | 2/1998 | Steffee |
| 5,782,832 A | 9/1998 | Larsen et al. |
| 5,800,547 A | 9/1998 | Schafer et al. |
| 5,800,550 A | 9/1998 | Sertich |
| 5,827,328 A | 10/1998 | Buttermann |
| 5,865,848 A | 2/1999 | Baker |
| 5,885,287 A | 3/1999 | Bagby |
| 5,928,284 A | 7/1999 | Mehdizadeh |
| 5,980,522 A | 11/1999 | Koros et al. |
| 6,045,579 A | 4/2000 | Hochshuler et al. |
| 6,080,158 A | 6/2000 | Lin |
| 6,080,193 A | 8/2000 | Hochshuler et al. |
| 6,102,949 A | 8/2000 | Biedermann et al. |
| 6,102,950 A | 8/2000 | Vaccaro |
| 6,117,174 A | 9/2000 | Nolan |
| 6,129,763 A | 10/2000 | Chauvin et al. |
| 6,156,067 A | 12/2000 | Bryan et al. |
| 6,159,244 A | 12/2000 | Suddaby |
| 6,174,311 B1 | 1/2001 | Branch |
| 6,174,334 B1 | 1/2001 | Suddaby |
| 6,176,881 B1 | 1/2001 | Suddaby |
| 6,176,882 B1 * | 1/2001 | Biedermann ........... A61F 2/447 623/17.11 |
| 6,179,873 B1 | 1/2001 | Zientek |
| 6,183,517 B1 | 2/2001 | Suddaby |
| 6,190,414 B1 | 2/2001 | Young et al. |
| 6,231,609 B1 | 5/2001 | Mehdizadeh |
| 6,319,257 B1 | 11/2001 | Carignan et al. |
| 6,342,074 B1 | 1/2002 | Simpson |
| 6,371,968 B1 | 4/2002 | Kogasaka et al. |
| 6,371,987 B1 | 4/2002 | Weiland et al. |
| 6,375,655 B1 | 4/2002 | Zdeblick et al. |
| 6,375,683 B1 | 4/2002 | Crozet et al. |
| 6,409,766 B1 | 6/2002 | Brett |
| 6,419,705 B1 | 7/2002 | Erickson |
| 6,436,140 B1 | 8/2002 | Liu et al. |
| 6,443,989 B1 | 9/2002 | Jackson |
| 6,454,806 B1 | 9/2002 | Cohen et al. |
| 6,454,807 B1 | 9/2002 | Jackson |
| 6,464,727 B1 | 10/2002 | Sharkey et al. |
| 6,488,710 B2 | 12/2002 | Besselink |
| 6,491,695 B1 | 12/2002 | Roggenbuck |
| 6,527,803 B1 | 3/2003 | Crozet et al. |
| 6,562,041 B1 | 5/2003 | Yonemura et al. |
| 6,572,619 B2 | 6/2003 | Santilli |
| 6,572,653 B1 | 6/2003 | Simonson |
| 6,575,042 B1 | 6/2003 | Rinner |
| 6,576,016 B1 | 6/2003 | Hochshuler et al. |
| 6,582,431 B1 | 6/2003 | Ray |
| 6,582,451 B1 | 6/2003 | Marucci |
| 6,582,467 B1 | 6/2003 | Teitelbaum et al. |
| 6,595,995 B2 | 7/2003 | Zdeblick et al. |
| 6,613,091 B1 | 9/2003 | Zdeblick et al. |
| 6,645,249 B2 | 11/2003 | Ralph et al. |
| 6,652,584 B2 | 11/2003 | Michelson |
| 6,666,888 B1 | 12/2003 | Jackson |
| 6,685,742 B1 | 2/2004 | Jackson |
| 6,706,070 B1 | 3/2004 | Wagner et al. |
| 6,709,458 B2 | 3/2004 | Michelson |
| 6,723,126 B1 | 4/2004 | Berry |
| 6,723,128 B2 | 4/2004 | Uk |
| 6,746,454 B2 | 6/2004 | Winterbottom et al. |
| 6,767,367 B1 | 7/2004 | Michelson |
| 6,770,095 B2 | 8/2004 | Grinberg et al. |
| 6,770,096 B2 | 8/2004 | Bolger et al. |
| 6,808,537 B2 | 10/2004 | Michelson |
| 6,821,298 B1 | 11/2004 | Jackson |
| 6,830,589 B2 | 12/2004 | Erickson |
| 6,835,206 B2 | 12/2004 | Jackson |
| 6,923,830 B2 | 8/2005 | Michelson |
| 6,902,568 B2 | 9/2005 | Serhan |
| 6,962,606 B2 | 11/2005 | Michelson |
| 6,979,353 B2 | 12/2005 | Bresina |
| 6,989,011 B2 | 1/2006 | Paul et al. |
| 7,008,453 B1 | 3/2006 | Michelson |
| 7,018,415 B1 | 3/2006 | McKay |
| 7,041,309 B2 | 5/2006 | Remington et al. |
| 7,048,763 B2 | 5/2006 | Ralph et al. |
| 7,094,257 B2 | 8/2006 | Mujwid et al. |
| 7,097,648 B1 | 8/2006 | Globerman |
| 7,108,862 B2 | 9/2006 | Remington et al. |
| 7,118,598 B2 | 10/2006 | Michelson |
| 7,128,760 B2 | 10/2006 | Michelson |
| 7,166,130 B2 | 1/2007 | Ferree |
| 7,172,561 B2 | 2/2007 | Grimberg |
| 7,211,112 B2 | 5/2007 | Baynham et al. |
| 7,217,291 B2 | 5/2007 | Zucherman et al. |
| 7,217,293 B2 | 5/2007 | Branch, Jr. |
| 7,220,280 B2 | 5/2007 | Kast et al. |
| 7,235,103 B2 | 7/2007 | Rivin |
| 7,238,186 B2 | 7/2007 | Zdeblick et al. |
| 7,331,994 B2 | 2/2008 | Gordon et al. |
| 7,331,996 B2 | 2/2008 | Soto et al. |
| 7,431,735 B2 | 10/2008 | Liu et al. |
| 7,445,636 B2 | 11/2008 | Michelson |
| 7,479,160 B2 | 1/2009 | Branch et al. |
| 7,500,992 B2 | 3/2009 | Li |
| 7,537,612 B2 | 5/2009 | Kunzler |
| 7,578,849 B2 | 8/2009 | Trieu |
| 7,584,682 B2 | 9/2009 | Hsiao |
| 7,588,573 B2 | 9/2009 | Berry |
| 7,608,107 B2 | 10/2009 | Michelson |
| 7,621,956 B2 | 11/2009 | Paul et al. |
| 7,674,296 B2 | 3/2010 | Rhonda et al. |
| 7,678,148 B2 | 3/2010 | Peterman |
| 7,682,376 B2 | 3/2010 | Trieu |
| 7,691,147 B2 | 4/2010 | Gutlin et al. |
| 7,703,727 B2 | 4/2010 | Selness |
| 7,727,280 B2 | 6/2010 | McLuen |
| 7,749,252 B2 | 7/2010 | Zucherman et al. |
| 7,753,958 B2 | 7/2010 | Gordon et al. |
| 7,758,617 B2 | 7/2010 | Lott et al. |
| 7,794,501 B2 | 9/2010 | Edie et al. |
| 7,799,081 B2 | 9/2010 | McKinley |
| D626,233 S | 10/2010 | Cipoletti et al. |
| 7,811,287 B2 | 10/2010 | Errico et al. |
| 7,811,327 B2 | 10/2010 | Hansell et al. |
| 7,828,849 B2 | 11/2010 | Lin |
| 7,837,688 B2 | 11/2010 | Boyer, II et al. |
| 7,837,734 B2 | 11/2010 | Zucherman et al. |
| 7,850,733 B2 | 12/2010 | Baynham et al. |
| 7,931,688 B2 | 4/2011 | Landry et al. |
| 7,932,825 B2 | 4/2011 | Berger |
| 7,935,117 B2 | 5/2011 | Sackett et al. |

(56) References Cited

U.S. PATENT DOCUMENTS

| | | | |
|---|---|---|---|
| RE42,480 E | 6/2011 | Bryan et al. | |
| 7,985,231 B2 | 7/2011 | Sankaran | |
| 8,002,834 B2 | 8/2011 | de Villiers et al. | |
| 8,043,295 B2 | 10/2011 | Reed | |
| 8,062,375 B2 | 11/2011 | Glerum et al. | |
| 8,070,813 B2 | 12/2011 | Grotz et al. | |
| 8,088,402 B2 | 1/2012 | Remington et al. | |
| 8,105,382 B2 | 1/2012 | Olmos et al. | |
| 8,110,004 B2 | 2/2012 | Valdevit et al. | |
| 8,114,092 B2 | 2/2012 | Altarac | |
| 8,187,332 B2 | 5/2012 | McLuen | |
| 8,221,502 B2 | 7/2012 | Branch, Jr. | |
| 8,262,666 B2 | 9/2012 | Baynham et al. | |
| 8,262,736 B2 | 9/2012 | Michelson | |
| 8,267,968 B2 | 9/2012 | Remington et al. | |
| 8,273,129 B2 | 9/2012 | Baynham et al. | |
| 8,282,683 B2 | 10/2012 | McLaughlin et al. | |
| 8,292,963 B2 | 10/2012 | Miller et al. | |
| 8,303,601 B2 | 11/2012 | Bandeira et al. | |
| 8,303,658 B2 | 11/2012 | Peterman | |
| 8,308,801 B2 | 11/2012 | Halverson et al. | |
| 8,308,804 B2 | 11/2012 | Kreuger et al. | |
| 8,308,805 B2 | 11/2012 | Lynn | |
| 8,317,025 B1 | 11/2012 | Kolozs et al. | |
| 8,317,798 B2 | 11/2012 | Lim | |
| 8,328,962 B2 | 12/2012 | Schussler | |
| 8,337,562 B2 | 12/2012 | Landry et al. | |
| 8,343,222 B2 | 1/2013 | Cope | |
| 8,361,152 B2 | 1/2013 | McCormack et al. | |
| 8,366,777 B2 | 2/2013 | Matthis et al. | |
| 8,403,990 B2 | 3/2013 | Dryer et al. | |
| 8,444,696 B2 | 5/2013 | Michelson | |
| 8,444,697 B1 | 5/2013 | Butler et al. | |
| 8,454,623 B2 | 6/2013 | Patel | |
| 8,485,075 B1 | 7/2013 | Gauthier et al. | |
| 8,579,904 B2 | 11/2013 | Siccardi | |
| 8,585,763 B2 | 11/2013 | Olevsky et al. | |
| 8,591,587 B2 | 11/2013 | Refai et al. | |
| 8,597,360 B2 | 12/2013 | McLuen et al. | |
| 8,690,886 B2 | 4/2014 | Li | |
| 8,734,337 B2 | 5/2014 | Deitch | |
| 8,740,980 B2 | 6/2014 | Merves | |
| 8,894,710 B2 | 11/2014 | Simpson et al. | |
| 9,119,725 B2 | 9/2015 | Barrall | |
| 9,155,629 B2 | 10/2015 | Remington et al. | |
| 9,186,262 B2 | 11/2015 | McLuen et al. | |
| 9,216,098 B2 | 12/2015 | Trudeau | |
| 9,301,853 B2 | 4/2016 | Richter | |
| 9,308,098 B2 | 4/2016 | Boehm | |
| 9,320,610 B2* | 4/2016 | Alheidt | A61F 2/4611 |
| 9,358,123 B2 | 6/2016 | McLuen et al. | |
| 9,358,672 B2 | 6/2016 | Gauthier et al. | |
| 9,445,920 B2* | 9/2016 | Baynham | A61F 2/447 |
| 9,526,525 B2 | 12/2016 | Remington et al. | |
| 9,532,883 B2 | 1/2017 | McLuen et al. | |
| 9,545,283 B2 | 1/2017 | Sack | |
| 9,655,740 B1 | 5/2017 | Faulkner | |
| 9,700,425 B1* | 7/2017 | Smith | A61B 17/025 |
| 9,724,208 B2 | 8/2017 | Robinson | |
| 9,737,316 B2 | 8/2017 | Bertagnoli | |
| 9,750,617 B2 | 9/2017 | Lim | |
| 9,757,111 B2 | 9/2017 | Fehling | |
| 9,757,249 B2 | 9/2017 | Radcliffe | |
| 9,757,250 B2 | 9/2017 | Josse | |
| 9,782,267 B2 | 10/2017 | Barrall | |
| 9,782,271 B2 | 10/2017 | Cipoletti | |
| 9,801,734 B1 | 10/2017 | Stein | |
| 9,931,224 B2 | 4/2018 | Lindenmann | |
| 9,949,841 B2* | 4/2018 | Glerum | A61F 2/4455 |
| 9,974,665 B2 | 5/2018 | McLuen et al. | |
| 10,016,283 B2 | 7/2018 | McLuen et al. | |
| 10,092,422 B2 | 10/2018 | McLuen et al. | |
| 10,098,757 B2 | 10/2018 | Logan et al. | |
| 10,111,760 B2 | 10/2018 | Knapp et al. | |
| 10,159,583 B2 | 12/2018 | Dietzel et al. | |
| 10,213,321 B2 | 2/2019 | Knapp et al. | |
| 2002/0033305 A1 | 3/2002 | Koyama et al. | |
| 2002/0049445 A1* | 4/2002 | Hall, IV | A61B 17/746 |
| | | | 606/281 |
| 2002/0128713 A1 | 9/2002 | Ferree | |
| 2002/0128716 A1 | 9/2002 | Cohen et al. | |
| 2002/0165613 A1 | 11/2002 | Lin et al. | |
| 2003/0036762 A1 | 2/2003 | Kerr | |
| 2003/0109932 A1 | 6/2003 | Keynan | |
| 2003/0149484 A1 | 8/2003 | Micheson | |
| 2003/0229355 A1 | 12/2003 | Keller | |
| 2003/0232065 A1 | 12/2003 | Remington et al. | |
| 2003/0236520 A1 | 12/2003 | Lim | |
| 2004/0024461 A1 | 2/2004 | Ferree | |
| 2004/0039448 A1 | 2/2004 | Pisharodi | |
| 2004/0068269 A1 | 4/2004 | Bonati | |
| 2004/0087947 A1 | 5/2004 | Lim et al. | |
| 2004/0087949 A1 | 5/2004 | Lim et al. | |
| 2004/0102077 A1 | 5/2004 | Trieu | |
| 2004/0102774 A1 | 5/2004 | Trieu | |
| 2004/0106998 A1 | 6/2004 | Ferree | |
| 2004/0127993 A1 | 7/2004 | Kast et al. | |
| 2004/0138750 A1 | 7/2004 | Michell | |
| 2004/0148027 A1 | 7/2004 | Errico et al. | |
| 2004/0153065 A1 | 8/2004 | Lim | |
| 2004/0181285 A1 | 9/2004 | Simonson | |
| 2004/0204762 A1 | 10/2004 | Ralph et al. | |
| 2004/0230309 A1 | 11/2004 | DiMauro et al. | |
| 2004/0243238 A1 | 12/2004 | Arnin et al. | |
| 2005/0015149 A1 | 1/2005 | Michelson | |
| 2005/0021042 A1 | 1/2005 | Marnay | |
| 2005/0027360 A1 | 2/2005 | Webb et al. | |
| 2005/0038515 A1 | 2/2005 | Kunzler | |
| 2005/0065610 A1 | 3/2005 | Pisharodi | |
| 2005/0107878 A1 | 5/2005 | Conchy | |
| 2005/0182416 A1 | 8/2005 | Lim et al. | |
| 2005/0278036 A1 | 12/2005 | Leonard et al. | |
| 2005/0283236 A1 | 12/2005 | Razin | |
| 2006/0052872 A1 | 3/2006 | Studer et al. | |
| 2006/0069436 A1 | 3/2006 | Sutton et al. | |
| 2006/0074431 A1 | 4/2006 | Sutton | |
| 2006/0095136 A1 | 5/2006 | McLuen | |
| 2006/0116769 A1 | 6/2006 | Marnay et al. | |
| 2006/0122701 A1 | 6/2006 | Keister | |
| 2006/0129244 A1 | 6/2006 | Ensign | |
| 2006/0142859 A1 | 6/2006 | McLuen | |
| 2006/0149381 A1 | 7/2006 | Kim | |
| 2006/0155295 A1 | 7/2006 | Supper | |
| 2006/0190084 A1 | 8/2006 | Doubler et al. | |
| 2006/0200243 A1 | 9/2006 | Rothman et al. | |
| 2006/0200244 A1* | 9/2006 | Assaker | A61F 2/44 |
| | | | 623/17.15 |
| 2006/0233853 A1 | 10/2006 | Remington et al. | |
| 2006/0235426 A1 | 10/2006 | Lim | |
| 2006/0241643 A1 | 10/2006 | Lim et al. | |
| 2006/0241764 A1 | 10/2006 | Michelson | |
| 2006/0241766 A1 | 10/2006 | Felton et al. | |
| 2006/0241767 A1 | 10/2006 | Doty | |
| 2006/0241770 A1* | 10/2006 | Rhoda | A61F 2/44 |
| | | | 623/17.15 |
| 2006/0241774 A1 | 10/2006 | Attali et al. | |
| 2006/0247679 A1 | 11/2006 | Peterman | |
| 2006/0253201 A1 | 11/2006 | McLuen | |
| 2006/0276899 A1 | 12/2006 | Zipnick et al. | |
| 2006/0293752 A1 | 12/2006 | Mourmene et al. | |
| 2006/0293753 A1 | 12/2006 | Thramann | |
| 2007/0050030 A1 | 3/2007 | Kim | |
| 2007/0067038 A1 | 3/2007 | Studer et al. | |
| 2007/0093897 A1 | 4/2007 | Gerbee et al. | |
| 2007/0093901 A1 | 4/2007 | Grotz et al. | |
| 2007/0191954 A1 | 8/2007 | Hansell et al. | |
| 2007/0233254 A1 | 8/2007 | Hansell et al. | |
| 2007/0209222 A1* | 9/2007 | Fischer | A61F 2/4657 |
| | | | 33/512 |
| 2007/0213641 A1 | 9/2007 | Francis | |
| 2007/0255407 A1 | 11/2007 | Castleman et al. | |
| 2007/0255409 A1* | 11/2007 | Dickson | A61F 2/30744 |
| | | | 623/17.11 |
| 2007/0255413 A1 | 11/2007 | Edie et al. | |

(56) References Cited

U.S. PATENT DOCUMENTS

| | | |
|---|---|---|
| 2007/0255415 A1 | 11/2007 | Edie et al. |
| 2007/0260260 A1 | 11/2007 | Hahn |
| 2007/0270954 A1* | 11/2007 | Wu ............... A61B 17/70 623/17.11 |
| 2007/0270968 A1* | 11/2007 | Baynham ............... A61F 2/447 623/17.11 |
| 2007/0282372 A1 | 12/2007 | Yedlicka |
| 2007/0282441 A1 | 12/2007 | Stream et al. |
| 2008/0009868 A1 | 1/2008 | Gotfried et al. |
| 2008/0009880 A1 | 1/2008 | Warnick et al. |
| 2008/0015701 A1 | 1/2008 | Garcia et al. |
| 2008/0021476 A1* | 1/2008 | Kirschman ........ A61B 17/7059 606/288 |
| 2008/0021555 A1 | 1/2008 | White |
| 2008/0021558 A1 | 1/2008 | Thramann |
| 2008/0021559 A1 | 1/2008 | Thramann |
| 2008/0046083 A1 | 2/2008 | Hewko |
| 2008/0051787 A1 | 2/2008 | Remington et al. |
| 2008/0051902 A1 | 2/2008 | Dwyer |
| 2008/0077153 A1 | 3/2008 | Pernsteiner et al. |
| 2008/0097435 A1 | 4/2008 | Deridder et al. |
| 2008/0114367 A1 | 5/2008 | Gauthier |
| 2008/0125778 A1 | 5/2008 | Li |
| 2008/0132949 A1 | 6/2008 | Aferzon et al. |
| 2008/0140207 A1* | 6/2008 | Olmos ............... A61F 2/4611 623/17.16 |
| 2008/0147193 A1 | 6/2008 | Matthis et al. |
| 2008/0154381 A1 | 6/2008 | Parrish |
| 2008/0161817 A1 | 7/2008 | Parsons et al. |
| 2008/0177275 A1 | 7/2008 | Wing et al. |
| 2008/0208264 A1 | 8/2008 | Lazarof |
| 2008/0269756 A1 | 10/2008 | Tomko |
| 2008/0269905 A1 | 10/2008 | Link |
| 2008/0287995 A1 | 11/2008 | Gauthier |
| 2008/0288073 A1 | 11/2008 | Renganath |
| 2008/0288076 A1 | 11/2008 | Soo et al. |
| 2008/0306489 A1 | 12/2008 | Altarac et al. |
| 2009/0030422 A1 | 1/2009 | Parsons et al. |
| 2009/0099601 A1 | 4/2009 | Aferzon et al. |
| 2009/0105828 A1 | 4/2009 | Gimbel |
| 2009/0112217 A1 | 4/2009 | Hester |
| 2009/0112220 A1 | 4/2009 | Kraus |
| 2009/0112324 A1* | 4/2009 | Refai ............... A61F 2/44 623/17.11 |
| 2009/0112325 A1* | 4/2009 | Refai ............... A61F 2/30734 623/17.16 |
| 2009/0164018 A1 | 6/2009 | Sommerich |
| 2009/0164020 A1 | 6/2009 | Janowski et al. |
| 2009/0182343 A1* | 7/2009 | Trudeau ............... A61F 2/4657 606/102 |
| 2009/0192611 A1* | 7/2009 | Lindner ............... A61F 2/44 623/17.11 |
| 2009/0198241 A1 | 8/2009 | Phan |
| 2009/0198245 A1* | 8/2009 | Phan ............... A61B 17/7065 606/99 |
| 2009/0198338 A1* | 8/2009 | Phan ............... A61B 17/7065 623/17.16 |
| 2009/0210061 A1 | 8/2009 | Sledge |
| 2009/0222100 A1 | 9/2009 | Cipoletti et al. |
| 2009/0222101 A1 | 9/2009 | de Villiers et al. |
| 2009/0228110 A1 | 9/2009 | McClintock |
| 2009/0265008 A1 | 10/2009 | Thibodeau |
| 2009/0292361 A1 | 11/2009 | Lopez |
| 2009/0299478 A1 | 12/2009 | Carls et al. |
| 2009/0306672 A1 | 12/2009 | Reindel et al. |
| 2010/0010494 A1* | 1/2010 | Quirno ............... A61F 2/4657 606/90 |
| 2010/0015747 A1 | 1/2010 | Kwon et al. |
| 2010/0023057 A1 | 1/2010 | Aeschlimann et al. |
| 2010/0024487 A1 | 2/2010 | Khoo et al. |
| 2010/0057204 A1 | 3/2010 | Kadaba et al. |
| 2010/0100100 A1* | 4/2010 | Refai ............... A61F 2/4611 606/99 |
| 2010/0114106 A1* | 5/2010 | Weber ............... A61F 2/4657 606/102 |
| 2010/0114183 A1 | 5/2010 | Wassinger et al. |
| 2010/0145456 A1 | 6/2010 | Simpson et al. |
| 2010/0168862 A1 | 7/2010 | Edie |
| 2010/0179657 A1* | 7/2010 | Greenhalgh ............... A61F 2/44 623/17.11 |
| 2010/0204795 A1 | 8/2010 | Greenhalgh |
| 2010/0211119 A1* | 8/2010 | Refai ............... A61F 2/44 606/86 A |
| 2010/0211176 A1* | 8/2010 | Greenhalgh ............... A61F 2/447 623/17.15 |
| 2010/0222884 A1 | 9/2010 | Greenhalgh |
| 2010/0234956 A1 | 9/2010 | Attia et al. |
| 2010/0241231 A1 | 9/2010 | Marino et al. |
| 2010/0256768 A1 | 10/2010 | Lim et al. |
| 2010/0262247 A1 | 10/2010 | Arnin |
| 2010/0274357 A1* | 10/2010 | Miller ............... A61F 2/44 623/17.16 |
| 2010/0280622 A1 | 11/2010 | McKinley |
| 2010/0286779 A1 | 11/2010 | Thibodeau |
| 2010/0286780 A1 | 11/2010 | Dryer et al. |
| 2010/0292796 A1 | 11/2010 | Greenhalgh et al. |
| 2010/0298939 A1 | 11/2010 | Delfosse et al. |
| 2010/0324606 A1 | 12/2010 | Moskowitz et al. |
| 2010/0331885 A1 | 12/2010 | Remington et al. |
| 2011/0015638 A1 | 1/2011 | Pischi et al. |
| 2011/0015682 A1* | 1/2011 | Lewis ............... A61B 17/8047 606/305 |
| 2011/0015741 A1 | 1/2011 | Melkent |
| 2011/0015742 A1 | 1/2011 | Hong |
| 2011/0015747 A1 | 1/2011 | McManus |
| 2011/0035007 A1* | 2/2011 | Patel ............... A61F 2/4465 623/17.11 |
| 2011/0035011 A1 | 2/2011 | Cain |
| 2011/0054621 A1 | 3/2011 | Lim |
| 2011/0077738 A1 | 3/2011 | Ciupik et al. |
| 2011/0087329 A1 | 4/2011 | Poulos |
| 2011/0093074 A1* | 4/2011 | Glerum ............... A61F 2/447 623/17.16 |
| 2011/0112587 A1 | 5/2011 | Patel et al. |
| 2011/0130835 A1 | 6/2011 | Ashley et al. |
| 2011/0130838 A1 | 6/2011 | Morgenstern Lopez |
| 2011/0138948 A1 | 6/2011 | Jimenez et al. |
| 2011/0160861 A1 | 6/2011 | Jimenez et al. |
| 2011/0172716 A1 | 7/2011 | Glerum |
| 2011/0172774 A1* | 7/2011 | Varela ............... A61F 2/447 623/17.16 |
| 2011/0202135 A1 | 8/2011 | Baek |
| 2011/0213465 A1 | 9/2011 | Landry et al. |
| 2011/0218627 A1 | 9/2011 | Rampersaud et al. |
| 2011/0230970 A1 | 9/2011 | Lynn et al. |
| 2011/0238184 A1 | 9/2011 | Zdeblick et al. |
| 2011/0251691 A1* | 10/2011 | McLaughlin ............... A61F 2/44 623/17.16 |
| 2011/0251692 A1 | 10/2011 | McLaughlin |
| 2011/0257751 A1* | 10/2011 | Sherman ............... A61F 2/44 623/17.16 |
| 2011/0282453 A1 | 11/2011 | Greenhalgh et al. |
| 2011/0301712 A1 | 12/2011 | Palmatier et al. |
| 2011/0307066 A1 | 12/2011 | Lim et al. |
| 2011/0319997 A1* | 12/2011 | Glerum ............... A61F 2/447 623/17.15 |
| 2012/0035729 A1 | 2/2012 | Glerum et al. |
| 2012/0058451 A1 | 3/2012 | Lazarof |
| 2012/0059470 A1* | 3/2012 | Weiman ............... A61F 2/442 623/17.11 |
| 2012/0059472 A1* | 3/2012 | Weiman ............... A61F 2/44 623/17.12 |
| 2012/0059473 A1* | 3/2012 | Weiman ............... A61F 2/44 623/17.16 |
| 2012/0059474 A1* | 3/2012 | Weiman ............... A61F 2/44 623/17.16 |
| 2012/0059475 A1* | 3/2012 | Weiman ............... A61F 2/44 623/17.16 |
| 2012/0059481 A1 | 3/2012 | Abernathie et al. |
| 2012/0064487 A1 | 3/2012 | Lazarof |
| 2012/0064488 A1 | 3/2012 | Lazarof |

(56) References Cited

U.S. PATENT DOCUMENTS

| | | |
|---|---|---|
| 2012/0071979 A1 | 3/2012 | Zipnick |
| 2012/0089228 A1 | 4/2012 | Poulos |
| 2012/0130493 A1* | 5/2012 | McLaughlin ......... A61F 2/4455 623/17.16 |
| 2012/0130494 A1 | 5/2012 | DeLurio et al. |
| 2012/0136448 A1 | 5/2012 | Seifert et al. |
| 2012/0143194 A1 | 6/2012 | Seifert et al. |
| 2012/0143201 A1 | 6/2012 | Seifert et al. |
| 2012/0150304 A1 | 6/2012 | Glerum et al. |
| 2012/0150305 A1 | 6/2012 | Glerum et al. |
| 2012/0158071 A1 | 6/2012 | Jimenez et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0191194 A1 | 7/2012 | Olmos et al. |
| 2012/0197403 A1* | 8/2012 | Merves ................ A61F 2/44 623/17.16 |
| 2012/0197404 A1 | 8/2012 | Brun et al. |
| 2012/0203347 A1 | 8/2012 | Glerum et al. |
| 2012/0209384 A1* | 8/2012 | Arnold ................ A61F 2/4455 623/17.15 |
| 2012/0209386 A1 | 8/2012 | Triplett |
| 2012/0226357 A1* | 9/2012 | Varela ................. A61F 2/447 623/17.16 |
| 2012/0232552 A1 | 9/2012 | Morgenstern Lopez |
| 2012/0232601 A1 | 9/2012 | Chabansky et al. |
| 2012/0232659 A1* | 9/2012 | Himmelberger ...... A61F 2/4465 623/17.16 |
| 2012/0232660 A1* | 9/2012 | Davenport ............ A61F 2/44 623/17.16 |
| 2012/0245691 A1 | 9/2012 | Reimels |
| 2012/0253412 A1 | 10/2012 | Lee |
| 2012/0265303 A1* | 10/2012 | Refai .................. A61F 2/44 623/17.11 |
| 2012/0271422 A1 | 10/2012 | Miller et al. |
| 2012/0276204 A1 | 11/2012 | Remington et al. |
| 2012/0277810 A1 | 11/2012 | Siccardi et al. |
| 2012/0277875 A1 | 11/2012 | Arnin |
| 2012/0290090 A1* | 11/2012 | Glerum ............... A61F 2/447 623/17.16 |
| 2012/0300124 A1 | 11/2012 | Yamashita |
| 2012/0303124 A1* | 11/2012 | McLuen ............. A61F 2/4455 623/17.16 |
| 2012/0310350 A1* | 12/2012 | Farris ................. A61F 2/4425 623/17.16 |
| 2012/0323327 A1 | 12/2012 | McAfee |
| 2012/0323328 A1* | 12/2012 | Weiman .............. A61F 2/442 623/17.16 |
| 2012/0330421 A1* | 12/2012 | Weiman .............. A61F 2/442 623/17.16 |
| 2012/0330422 A1* | 12/2012 | Weiman .............. A61F 2/442 623/17.16 |
| 2013/0006358 A1* | 1/2013 | Olevsky ............. A61F 2/4465 623/17.16 |
| 2013/0006359 A1* | 1/2013 | Fedorov ............. A61F 2/4465 623/17.16 |
| 2013/0006361 A1 | 1/2013 | Glerum et al. |
| 2013/0006364 A1 | 1/2013 | McCormack et al. |
| 2013/0018468 A1 | 1/2013 | Moskowitz et al. |
| 2013/0018469 A1 | 1/2013 | Moskowitz et al. |
| 2013/0018470 A1 | 1/2013 | Moskowitz et al. |
| 2013/0023991 A1 | 1/2013 | Moskowitz et al. |
| 2013/0023992 A1 | 1/2013 | Moskowitz et al. |
| 2013/0023993 A1* | 1/2013 | Weiman .............. A61F 2/442 623/17.16 |
| 2013/0023994 A1* | 1/2013 | Glerum .............. A61F 2/447 623/17.16 |
| 2013/0030534 A1 | 1/2013 | DeLurio et al. |
| 2013/0035724 A1 | 2/2013 | Fitzpatrick |
| 2013/0035763 A1 | 2/2013 | Krueger |
| 2013/0053962 A1 | 2/2013 | Moskowitz et al. |
| 2013/0073046 A1 | 3/2013 | Zaveloff |
| 2013/0079790 A1* | 3/2013 | Stein ................... A61B 17/025 606/102 |
| 2013/0079793 A1* | 3/2013 | Stein ................... A61F 2/4657 606/102 |
| 2013/0085572 A1* | 4/2013 | Glerum ............... A61F 2/442 623/17.16 |
| 2013/0103153 A1 | 4/2013 | Blackwell et al. |
| 2013/0103156 A1 | 4/2013 | Packer et al. |
| 2013/0110248 A1 | 5/2013 | Zipnick |
| 2013/0123927 A1* | 5/2013 | Malandain ......... A61B 17/8852 623/17.16 |
| 2013/0158663 A1 | 6/2013 | Miller et al. |
| 2013/0158664 A1 | 6/2013 | Palmatier et al. |
| 2013/0158668 A1* | 6/2013 | Nichols .............. A61F 2/4455 623/17.16 |
| 2013/0158669 A1* | 6/2013 | Sungarian ........... A61F 2/442 623/17.16 |
| 2013/0197642 A1* | 8/2013 | Ernst .................. A61F 2/442 623/17.16 |
| 2013/0204371 A1* | 8/2013 | McLuen .............. A61F 2/4455 623/17.16 |
| 2013/0211525 A1* | 8/2013 | McLuen .............. A61F 2/4455 623/17.16 |
| 2013/0211526 A1 | 8/2013 | Alheidt |
| 2013/0253650 A1 | 9/2013 | Ashley et al. |
| 2013/0274883 A1* | 10/2013 | McLuen .............. A61F 2/447 623/17.16 |
| 2013/0310938 A1 | 11/2013 | Sournac et al. |
| 2013/0317554 A1* | 11/2013 | Purcell ............... A61B 17/8047 606/319 |
| 2014/0012383 A1 | 1/2014 | Triplett |
| 2014/0039622 A1* | 2/2014 | Glerum .............. A61F 2/442 623/17.15 |
| 2014/0058521 A1 | 2/2014 | McLuen et al. |
| 2014/0066941 A1 | 3/2014 | Mignucci |
| 2014/0088708 A1 | 3/2014 | McLaughlin et al. |
| 2014/0094917 A1* | 4/2014 | Salerni .............. A61F 2/447 623/17.16 |
| 2014/0114414 A1* | 4/2014 | Abdou ............... A61F 2/4611 623/17.16 |
| 2014/0121774 A1* | 5/2014 | Glerum .............. A61F 2/4611 623/17.16 |
| 2014/0135776 A1* | 5/2014 | Huffmaster ......... A61F 2/4684 606/90 |
| 2014/0148902 A1 | 5/2014 | Dickson |
| 2014/0156006 A1 | 6/2014 | Bannigan et al. |
| 2014/0156007 A1* | 6/2014 | Pabst ................. A61F 2/442 623/17.16 |
| 2014/0156008 A1 | 6/2014 | Flickinger et al. |
| 2014/0180421 A1* | 6/2014 | Glerum .............. A61F 2/4611 623/17.16 |
| 2014/0214166 A1* | 7/2014 | Theofilos ........... A61F 2/4455 623/17.16 |
| 2014/0214167 A1* | 7/2014 | Theofilos ........... A61F 2/4455 623/17.16 |
| 2014/0236296 A1* | 8/2014 | Wagner .............. A61F 2/447 623/17.15 |
| 2014/0236297 A1* | 8/2014 | Iott .................... A61F 2/447 623/17.15 |
| 2014/0243982 A1* | 8/2014 | Miller ................ A61F 2/4455 623/17.16 |
| 2014/0249629 A1 | 9/2014 | Moskowitz et al. |
| 2014/0257296 A1* | 9/2014 | Morgenstern Lopez ................ A61B 17/1671 606/80 |
| 2014/0257485 A1 | 9/2014 | Matthis et al. |
| 2014/0277470 A1 | 9/2014 | Baynham |
| 2014/0277490 A1 | 9/2014 | Perloff |
| 2014/0277500 A1* | 9/2014 | Logan ................ A61F 2/447 623/17.16 |
| 2014/0277504 A1* | 9/2014 | Forton ............... A61F 2/4611 623/17.16 |
| 2014/0277509 A1 | 9/2014 | Robinson et al. |
| 2014/0277510 A1* | 9/2014 | Robinson ........... A61F 2/447 623/17.16 |
| 2014/0288652 A1* | 9/2014 | Boehm ............... A61F 2/4465 623/17.15 |

(56) References Cited

U.S. PATENT DOCUMENTS

| | | | |
|---|---|---|---|
| 2014/0343677 A1 | 11/2014 | Davis et al. | |
| 2014/0343678 A1 | 11/2014 | Suddaby et al. | |
| 2015/0012097 A1* | 1/2015 | Ibarra | A61F 2/447 623/17.15 |
| 2015/0018954 A1 | 1/2015 | Loebl | |
| 2015/0018957 A1* | 1/2015 | Nichols | A61F 2/4611 623/17.16 |
| 2015/0025633 A1* | 1/2015 | McLaughlin | A61F 2/44 623/17.15 |
| 2015/0066145 A1 | 3/2015 | Rogers | |
| 2015/0094814 A1* | 4/2015 | Emerick | A61F 2/4455 623/17.16 |
| 2015/0148906 A1* | 5/2015 | Sicotte | A61F 2/442 623/17.15 |
| 2015/0157469 A1* | 6/2015 | Prado | A61F 2/4601 606/86 A |
| 2015/0190242 A1* | 7/2015 | Blain | A61F 2/30771 623/17.12 |
| 2015/0238327 A1 | 8/2015 | Cheng | |
| 2015/0250606 A1 | 9/2015 | McLean | |
| 2015/0250609 A1 | 9/2015 | McLean | |
| 2015/0257894 A1 | 9/2015 | Levy | |
| 2015/0272743 A1* | 10/2015 | Jimenez | A61F 2/447 623/17.16 |
| 2015/0282797 A1* | 10/2015 | O'Neil | A61B 17/025 606/279 |
| 2015/0328013 A1* | 11/2015 | Barrall | A61F 2/44 623/17.16 |
| 2015/0351925 A1* | 12/2015 | Emerick | A61F 2/447 623/17.16 |
| 2015/0366675 A1* | 12/2015 | Matthews | A61F 2/4425 623/17.16 |
| 2015/0374507 A1* | 12/2015 | Wolters | A61F 2/447 623/17.15 |
| 2015/0374509 A1 | 12/2015 | McLean | |
| 2016/0015523 A1* | 1/2016 | Lewis | A61F 2/447 623/17.16 |
| 2016/0022438 A1* | 1/2016 | Lamborne | A61F 2/4455 623/17.16 |
| 2016/0030191 A1 | 2/2016 | McLuen et al. | |
| 2016/0030195 A1* | 2/2016 | Prevost | A61F 2/4611 623/17.16 |
| 2016/0038305 A1* | 2/2016 | Weiman | A61F 2/4455 623/17.16 |
| 2016/0045326 A1* | 2/2016 | Hansen | A61F 2/447 623/17.16 |
| 2016/0058575 A1* | 3/2016 | Sutterlin, III | A61F 2/4465 623/17.16 |
| 2016/0089247 A1 | 3/2016 | Nicholas | |
| 2016/0354211 A1 | 3/2016 | Packer | |
| 2016/0106551 A1 | 4/2016 | Grimberg, Jr. | |
| 2016/0242932 A1 | 8/2016 | McLuen et al. | |
| 2016/0256291 A1 | 9/2016 | Miller | |
| 2016/0278933 A1* | 9/2016 | Semler | A61F 2/442 |
| 2016/0317323 A1* | 11/2016 | Cho | A61F 2/4611 |
| 2016/0374735 A1* | 12/2016 | Bootwala | A61B 17/7091 606/86 A |
| 2017/0056197 A1* | 3/2017 | Weiman | A61F 2/447 |
| 2017/0071750 A1* | 3/2017 | Urban | A61F 2/4455 |
| 2017/0071752 A1 | 3/2017 | McLuen et al. | |
| 2017/0071753 A1* | 3/2017 | Josse | A61F 2/4611 |
| 2017/0100260 A1 | 4/2017 | Duffield | |
| 2017/0119542 A1* | 5/2017 | Logan | A61F 2/4455 |
| 2017/0119543 A1* | 5/2017 | Dietzel | A61F 2/447 |
| 2017/0202684 A1* | 7/2017 | Padovani | A61F 2/4657 |
| 2017/0215767 A1* | 8/2017 | Ziemek | A61B 5/1076 |
| 2017/0216050 A1* | 8/2017 | Semler | A61F 2/4425 |
| 2017/0224500 A1 | 8/2017 | Perloff | |
| 2017/0245997 A1* | 8/2017 | Trischler | A61F 2/44 |
| 2017/0273804 A1 | 9/2017 | Emerick | |
| 2017/0290671 A1* | 10/2017 | Milz | A61F 2/44 |
| 2017/0304066 A1 | 10/2017 | Smith | |
| 2017/0325969 A1 | 11/2017 | McLean | |
| 2017/0333198 A1* | 11/2017 | Robinson | A61F 2/447 |
| 2018/0014944 A1* | 1/2018 | Davis | A61F 2/447 |
| 2018/0036138 A1* | 2/2018 | Robinson | A61F 2/4455 |
| 2018/0042735 A1* | 2/2018 | Schell | A61F 2/4684 |
| 2018/0049890 A1 | 2/2018 | Propejoy | |
| 2018/0064551 A1* | 3/2018 | Stein | A61F 2/447 |
| 2018/0116815 A1* | 5/2018 | Kuyler | A61F 2/447 |
| 2018/0185163 A1* | 7/2018 | Weiman | A61F 2/442 |
| 2018/0200075 A1* | 7/2018 | Baker | A61F 2/4611 |
| 2018/0200076 A1* | 7/2018 | Knapp | A61F 2/4611 |
| 2018/0200077 A1* | 7/2018 | Knapp | A61F 2/4611 |
| 2018/0200078 A1* | 7/2018 | Remington | A61F 2/4611 |
| 2018/0228622 A1 | 8/2018 | McLuen et al. | |
| 2018/0263787 A1 | 9/2018 | McLuen et al. | |
| 2018/0289506 A1* | 10/2018 | Kim | A61L 27/06 |
| 2018/0296361 A1* | 10/2018 | Butler | A61F 2/442 |
| 2018/0303530 A1* | 10/2018 | Kang | A61B 17/8605 |
| 2018/0318107 A1* | 11/2018 | Cummins | A61F 2/4465 |
| 2018/0344485 A1 | 12/2018 | McLuen et al. | |
| 2019/0008649 A1 | 1/2019 | Logan et al. | |
| 2019/0008658 A1 | 1/2019 | Knapp et al. | |
| 2019/0083283 A1* | 3/2019 | Sharifi-Mehr | A61F 2/4601 |
| 2019/0105183 A1* | 4/2019 | Adamo | A61F 2/447 |
| 2019/0183656 A1* | 6/2019 | Stein | A61F 2/4455 |
| 2019/0201210 A1* | 7/2019 | Besaw | A61F 2/442 |
| 2019/0254841 A1* | 8/2019 | To | A61F 2/4684 |

FOREIGN PATENT DOCUMENTS

| | | |
|---|---|---|
| WO | 2006134262 A1 | 12/2006 |
| WO | 2008035849 A1 | 3/2008 |
| WO | 2008070863 A2 | 6/2008 |
| WO | 2008086276 A2 | 7/2008 |
| WO | 201006258 | 1/2010 |
| WO | 2010045301 A1 | 4/2010 |
| WO | 2010121030 A2 | 10/2010 |
| WO | 2011116136 A1 | 9/2011 |
| WO | 2013023096 A1 | 2/2013 |
| WO | 2013023098 A1 | 2/2013 |
| WO | 2013025876 A1 | 2/2013 |

OTHER PUBLICATIONS

International Search Report and Written Opinion from International Application No. PCT/US2018/013394.
International Search Report and Written Opinion from International Application No. PCT/US18/13681.
International Search Report and Written Opinion from International Application No. PCT/US18/013851 dated May 17, 2018.
International Search Report and Written Opinion from International Application No. PCT/US18/013717 dated Mar. 7, 2018.
The Second Office Action from the Chinese Application No. 201710881041.X, dated Jun. 26, 2019.
The International Preliminary Report from the International Application No. PCT/US2018/013681, dated Aug. 1, 2019.
The International Preliminary Report from the International Application No. PCT/US2018/013394, dated Aug. 1, 2019.
The International Preliminary Report from the International Application No. PCT/US2018/013715, dated Aug. 1, 2019.
The International Preliminary Report from the International Application No. PCT/US2018/013717, dated Aug. 1, 2019.
The International Preliminary Report from the International Application No. PCT/US2018/013851, dated Aug. 1, 2019.
The International Preliminary Report from the International Application No. PCT/US2018/013644, dated Aug. 1, 2019.
Australian Examination Report No. 1, from Australian Patent Application No. 2014236698.
International Search Report and Written Opinion from International Application No. PCT/US2018/13644.
International Search Report and Written Opinion from International Application No. PCT/US18/13715.

* cited by examiner

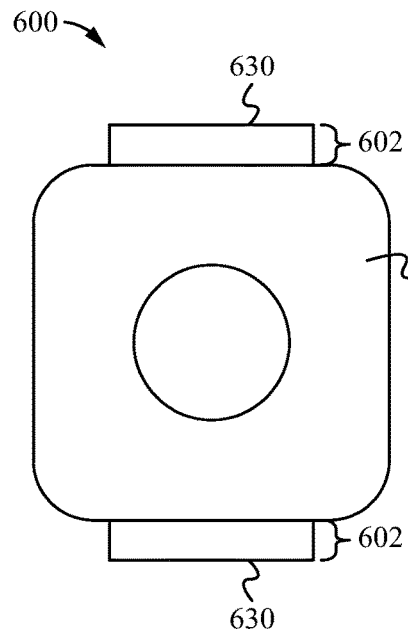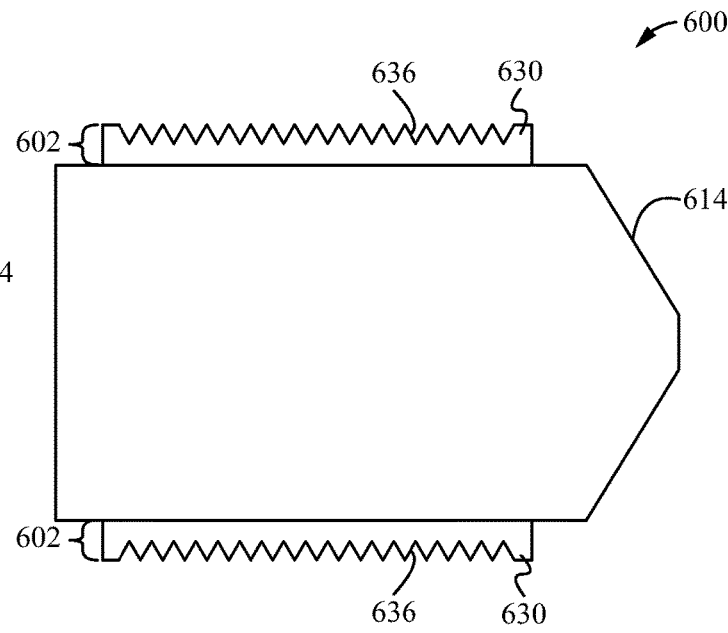
Fig. 6A  Fig. 6B
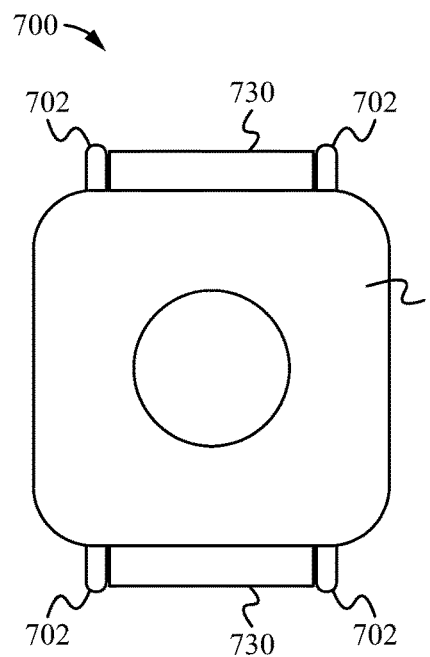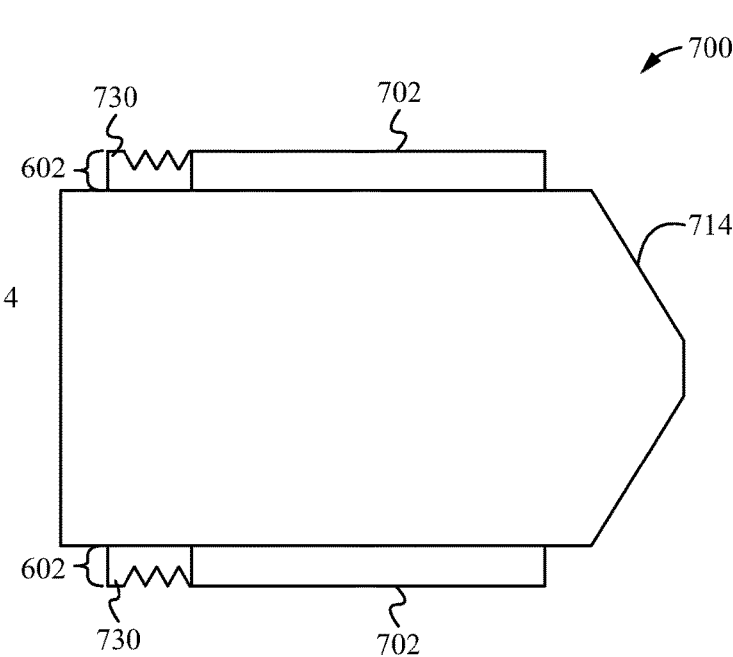
Fig. 7A  Fig. 7B

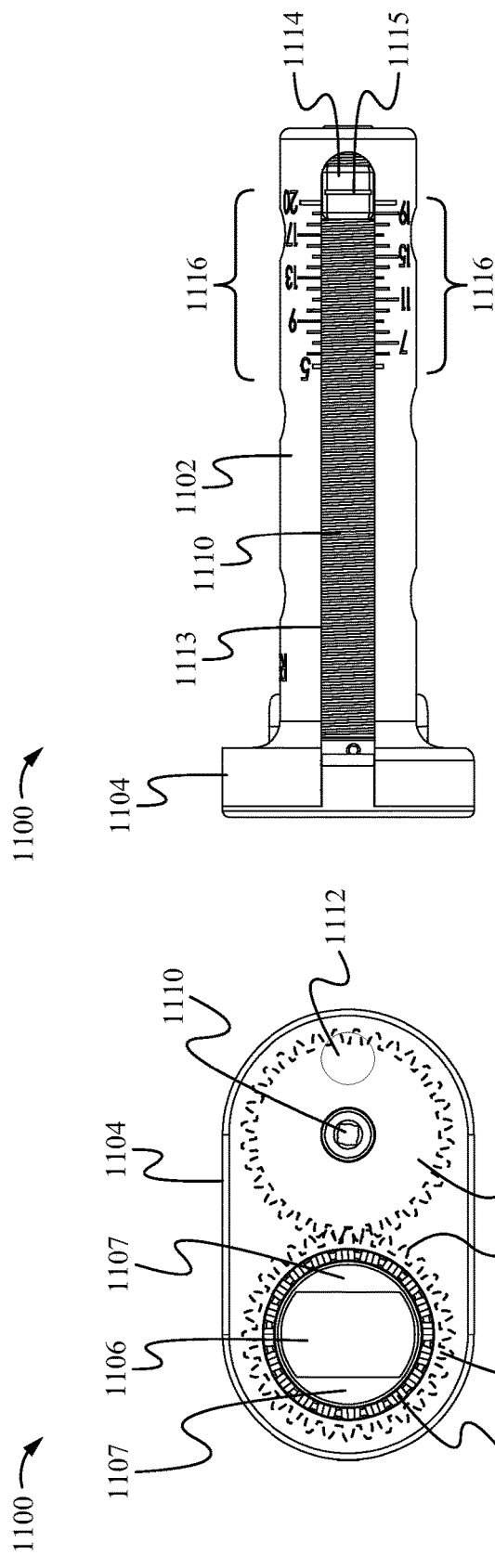
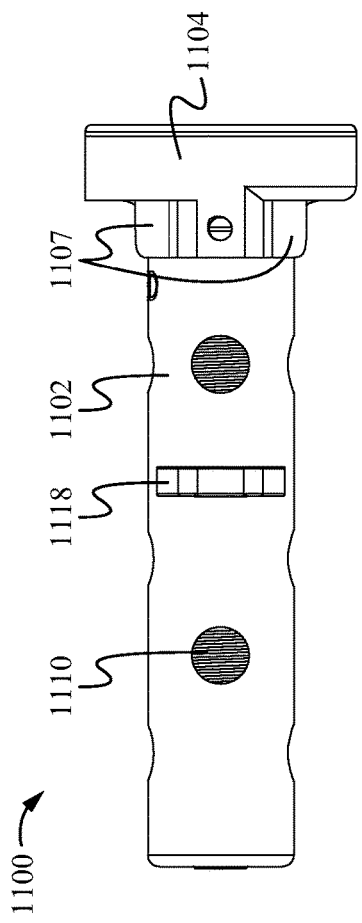
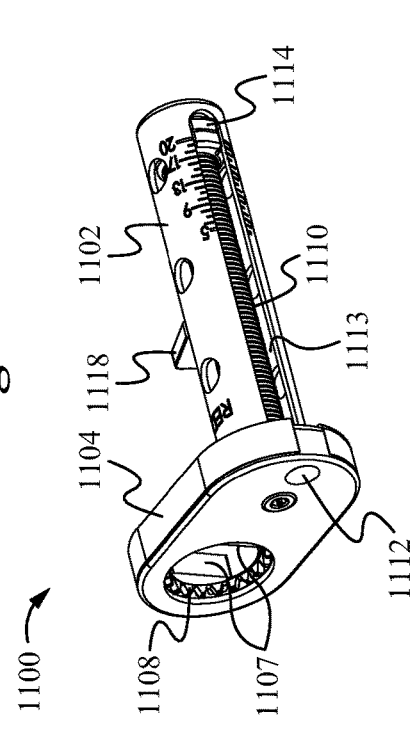
Fig. 11C
Fig. 11D
Fig. 11B
Fig. 11A

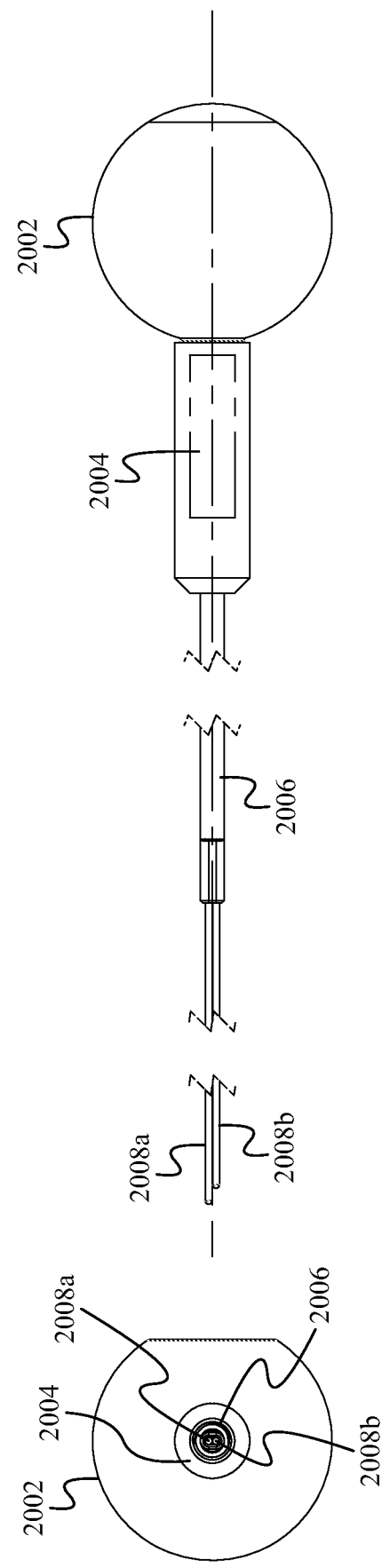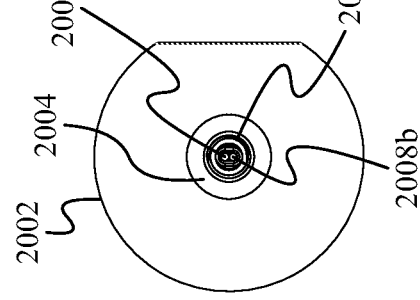
Fig. 20A
Fig. 20B
Fig. 20C

```
┌─────────────────────────────────────────────────────────────────────────┐
│ The user slides the docking rod through the central hollow channel of   │
│ the insertion instrument and couples the tip of the docking rod         │
│ into/with the positioning aperture of the bone fusion device.           │
└─────────────────────────────────────────────────────────────────────────┘ — 2102
                                    │
                                    ▼
┌─────────────────────────────────────────────────────────────────────────┐
│ The user spreads the fingers by rotating the control sleeve to the open │
│ or spread position thereby removing the fingers from the gripping       │
│ apertures and out of the channels.                                      │
└─────────────────────────────────────────────────────────────────────────┘ — 2104
                                    │
                                    ▼
┌─────────────────────────────────────────────────────────────────────────┐
│ The user then removes the insertion instrument from the patient leaving │
│ the docking rod coupled to the bone fusion device.                      │
└─────────────────────────────────────────────────────────────────────────┘ — 2106
                                    │
                                    ▼
┌─────────────────────────────────────────────────────────────────────────┐
│ The user couples the delivery member onto the docking rod until the     │
│ exit aperture is aligned with one or more of the channels of the device.│
└─────────────────────────────────────────────────────────────────────────┘ — 2108
                                    │
                                    ▼
┌─────────────────────────────────────────────────────────────────────────┐
│ The user prepares and inserts desired material into the cavity of the   │
│ funnel of the delivery member.                                          │
└─────────────────────────────────────────────────────────────────────────┘ — 2110
                                    │
                                    ▼
┌─────────────────────────────────────────────────────────────────────────┐
│ The user then pushes the material through the funnel and the shaft out  │
│ the exit aperture and into the bone fusion device using one or more of  │
│ the plungers.                                                           │
└─────────────────────────────────────────────────────────────────────────┘ — 2112
                                    │
                                    ▼
┌─────────────────────────────────────────────────────────────────────────┐
│ Once a desired amount of the material has been delivered to the device, │
│ the user removes or decouples the delivery member and/or docking rod    │
│ from the bone fusion device.                                            │
└─────────────────────────────────────────────────────────────────────────┘ — 2114
```

Fig. 21

BONE FUSION SYSTEM, DEVICE AND METHOD INCLUDING A MEASURING MECHANISM

RELATED APPLICATIONS

This application is a continuation of co-pending U.S. patent application Ser. No. 15/409,407, filed on Jan. 18, 2017 and entitled "BONE FUSION SYSTEM, DEVICE AND METHOD INCLUDING A MEASURING MECHANISM," which is hereby incorporated by reference.

FIELD OF THE INVENTION

This invention relates generally to bone fusion systems. More specifically, the present invention relates to systems for fusing vertebrae of the spine or other bones.

BACKGROUND OF THE INVENTION

The spinal column is made up of vertebrae stacked on top of one another. Between the vertebrae are discs which are gel-like cushions that act as shock-absorbers and keep the spine flexible. Injury, disease, or excessive pressure on the discs can cause degenerative disc disease or other disorders where the disc becomes thinner and allows the vertebrae to move closer together or become misaligned. Similarly, vertebrae are able to weaken due to impact or disease reducing their ability to properly distribute forces on the spine. As a result, nerves may become pinched, causing pain that radiates into other parts of the body, or instability of the vertebrae may ensue.

One method for correcting disc and/or vertebrae-related disorders is to insert a fusion cage as a replacement for and/or in between the vertebrae to act as a structural replacement for the deteriorated disc and/or vertebrae. The fusion cage is typically a hollow metal device usually made of titanium. Once inserted, the fusion cage maintains the proper separation between the vertebrae to prevent nerves from being pinched and provides structural stability to the spine. Also, the inside of the cage is filled with bone graft material which eventually fuses permanently with the adjacent vertebrae into a single unit. However, it is difficult to retain this bone graft material in the cage and in the proper positions to stimulate bone growth.

The use of fusion cages for fusion and stabilization of vertebrae in the spine is known in the prior art. U.S. Pat. No. 4,961,740 to Ray, et al. entitled, "V-Thread Fusion Cage and Method of Fusing a Bone Joint," discloses a fusion cage with a threaded outer surface, where the crown of the thread is sharp and cuts into the bone. Perforations are provided in valleys between adjacent turns of the thread. The cage can be screwed into a threaded bore provided in the bone structure at the surgical site and then packed with bone chips which promote fusion.

U.S. Pat. No. 5,015,247 to Michelson entitled, "Threaded Spinal Implant," discloses a fusion implant comprising a cylindrical member having a series of threads on the exterior of the cylindrical member for engaging the vertebrae to maintain the implant in place and a plurality of openings in the cylindrical surface.

U.S. Pat. No. 6,342,074 to Simpson entitled, "Anterior Lumbar Underbody Fusion Implant and Method For Fusing Adjacent Vertebrae," discloses a one-piece spinal fusion implant comprising a hollow body having an access passage for insertion of bone graft material into the intervertebral space after the implant has been affixed to adjacent vertebrae. The implant provides a pair of screw-receiving passages that are oppositely inclined relative to a central plane. In one embodiment, the screw-receiving passages enable the head of an orthopaedic screw to be retained entirely within the access passage.

U.S. Pat. No. 5,885,287 to Bagby entitled, "Self-tapping Interbody Bone Implant," discloses a bone joining implant with a rigid, implantable base body having an outer surface with at least one bone bed engaging portion configured for engaging between a pair of bone bodies to be joined, wherein at least one spline is provided by the bone bed engaging portion, the spline being constructed and arranged to extend outwardly of the body and having an undercut portion.

U.S. Pat. No. 6,582,467 to Teitelbaum et al. entitled, "Expandable Fusion Cage," discloses an expandable fusion cage where the surfaces of the cage have multiple portions cut out of the metal to form sharp barbs. As the cage is expanded, the sharp barbs protrude into the subcortical bone of the vertebrae to secure the cage in place. The cage is filled with bone or bone matrix material.

U.S. Pat. No. 5,800,550 to Sertich entitled, "Interbody Fusion Cage," discloses a prosthetic device which includes an inert generally rectangularly shaped support body adapted to be seated on hard end plates of vertebrae. The support body has top and bottom faces. A first peg is movably mounted in a first aperture located in the support body, and the first aperture terminates at one of the top and bottom faces of the support body. Further, the first peg projects away from the one of the top and bottom faces and into an adjacent vertebra to secure the support body in place relative to the vertebra.

U.S. Pat. No. 6,436,140 to Liu et al. entitled, "Expandable Interbody Fusion Cage and Method for Insertion," discloses an expandable hollow interbody fusion device, wherein the body is divided into a number of branches connected to one another at a fixed end and separated at an expandable end. The expandable cage may be inserted in its substantially cylindrical form and may be expanded by movement of an expansion member to establish lordosis of the spine. An expansion member interacts with the interior surfaces of the device to maintain the cage in the expanded condition and provide a large internal chamber for receiving bone in-growth material.

These patents all disclose fusion cage devices that can be inserted between vertebrae of the spine in an invasive surgical procedure. Such an invasive surgical procedure requires a long recovery period.

SUMMARY OF THE INVENTION

The present application is directed to a bone fusion system, method and device for insertion of a bone fusion device between bones that are to be fused together and/or in place of one or more of the bones, such as, for example, the vertebrae of a spinal column. The bone fusion device comprises one or more extendable plates having a central rib. The bone fusion device is able to be inserted between or replace the vertebrae by using an minimally invasive procedure. The bone fusion device comprises one or more support channels configured to receive an insertion instrument that is then secured to the bone fusion device via a coupling mechanism. As a result, the coupled device is able to be securely positioned between vertebrae using the insertion instrument with minimal risk of slippage. After the device has been positioned between the vertebrae, and the screw is rotated by the control mechanism to deliver the bone graft material and extend the plates. Two tabs or plates are extended upon rotating a rotating means wherein extending blocks travel up the screw pushing out the angled plates as the extending blocks approach the ends of the bone fusion device. The central rib of the tabs provides increased support against torsional forces creating more stable contact with the bones. In some embodiments, a single tab is extended. Thus, the tabs are able to be advantageously positioned in the confined space between the vertebrae to help brace the device until the bone has fused.

One aspect of the present application is directed to a bone fusion system for inserting a bone fusion device into a desired location. The system comprises an insertion instrument comprising a first end, a second end opposite the first end, a coupling mechanism having a control shaft and a plurality of fingers configured to move between a closed position wherein the fingers are close together to a spread position wherein the fingers are farther apart based on manipulation of the control shaft, a bone fusion device having a body and one or more extendable tabs, wherein the body of the bone fusion device is detachably coupled to the first end of the insertion instrument by the coupling mechanism and a measuring tool detachably coupled to the second end of the insertion instrument, the measuring tool comprising an indicating mechanism that indicates a variable tab extension value. In some embodiments, the system further comprises an engaging tool comprising a handle, an elongated member having a contoured tip and an interface gear, wherein the member and the interface gear are both coupled to a base of the handle with the interface gear being centered around the member. In some embodiments, the control shaft has a hollow axial cavity that extends from the first end to the second end, and further wherein the engaging tool detachably couples with the insertion instrument by sliding into the hollow axial cavity such that the base of the handle is adjacent to the second end. In some embodiments, the indicating mechanism comprises an indicating screw, a screw gear coupled to the indicating screw, a ring threaded onto the indicating screw and an offset gear operably coupled to a screw gear such that rotation of the offset gear causes rotation of the indicating screw via the screw gear thereby causing the ring to move up or down the indicating screw. In some embodiments, the offset gear comprises a first set of teeth and a second set of teeth, wherein the first set of teeth are operably coupled with the screw gear and, when coupled to the insertion instrument, the interface gear of the engaging tool is operably coupled with the second set of teeth such that rotation of the engaging tool causes rotation of the offset gear via the interface gear. In some embodiments, the bone fusion device comprises a positioning screw having a positioning aperture and operably coupled with the tabs such that rotation of the screw causes the tabs to extend from or retract into the body of the bone fusion device. In some embodiments, when the bone fusion device and the engaging tool are both coupled to the insertion instrument, the tip of the engaging tool slides into the positioning aperture of the positioning screw such that rotation of the engaging tool causes the positioning screw to rotate thereby extending or retracting the tabs. In some embodiments, the measuring tool couples to the insertion instrument by sliding the second end of the insertion instrument into a coupling aperture of the measuring tool and the engaging tool couples to the insertion instrument by sliding through the coupling aperture and the second end of the insertion instrument into the hollow axial cavity. In some embodiments, the measuring tool further comprises a compatibility marker that indicates a type of bone fusion device whose tab extension or retraction rate is proportional to a distance the ring moves up or down the indicating screw when the indicating screw is rotated with the positioning screw by the engaging tool.

A second aspect is directed to a method of operation of a bone fusion system. The method comprises providing an insertion instrument comprising a first end, a second end opposite the first end, a coupling mechanism having a control shaft and a plurality of fingers configured to move between a closed position wherein the fingers are close together to a spread position wherein the fingers are farther apart based on manipulation of the control shaft, detachably coupling a bone fusion device to the first end of the insertion instrument using the coupling mechanism, wherein the bone fusion device comprises a body and one or more extendable tabs and detachably coupling a measuring tool to the second end of the insertion instrument, the measuring tool comprising an indicating mechanism that indicates a variable tab extension value. In some embodiments, the method further comprises detachably coupling an engaging tool to the second end of the insertion instrument, the engaging tool comprising a handle, an elongated member having a contoured tip and an interface gear, wherein the member and the interface gear are both coupled to a base of the handle with the interface gear being centered around the member. In some embodiments, the control shaft has a hollow axial cavity that extends from the first end to the second end. In some embodiments, the indicating mechanism comprises an indicating screw, a screw gear coupled to the indicating screw, a ring threaded onto the indicating screw and an offset gear operably coupled to a screw gear, further comprising rotating the offset gear thereby causing rotation of the indicating screw via the screw gear which causes the ring to move up or down the indicating screw. In some embodiments, the offset gear comprises a first set of teeth and a second set of teeth, wherein the first set of teeth are operably coupled with the screw gear and, when coupled to the insertion instrument, the interface gear of the engaging tool is operably coupled with the second set of teeth such that rotation of the engaging tool causes rotation of the offset gear via the interface gear, wherein rotating the offset gear comprises rotating the handle of the engaging tool. In some embodiments, the bone fusion device comprises a positioning screw having a positioning aperture and operably coupled with the tabs such that rotation of the screw causes the tabs to extend from or retract into the body of the bone fusion device. In some embodiments, coupling the engaging tool to the second end of the insertion instrument comprises sliding the tip of the engaging tool into the positioning aperture of the positioning screw when the bone fusion device is coupled to the insertion instrument such that rotation of the engaging tool causes the positioning screw to rotate thereby extending or retracting the tabs. In some embodiments, coupling the measuring tool to the insertion instrument comprises sliding the second end of the insertion instrument into a coupling aperture of the measuring tool, and wherein the engaging tool couples to the insertion instrument by sliding through the coupling aperture and the second end of the insertion instrument into the hollow axial cavity. In some embodiments, the measuring tool further comprises a compatibility marker that indicates a type of bone fusion device whose tab extension or retraction rate is proportional to a distance the ring moves up or down the indicating screw when the indicating screw is rotated with the positioning screw by the engaging tool. In some embodiments, the detachably coupling of the bone fusion device to the insertion instrument comprises spreading a plurality of fingers of an insertion instrument with a control shaft of the insertion instrument, sliding the fingers of the insertion instrument into one or more surface channels of a bone fusion device and contracting the fingers with the control shaft such that the fingers move into the surface channels and the insertion instrument is detachably coupled with the bone fusion device.

A third aspect is directed to a measuring tool for use in the bone fusion device insertion system. The measuring tool comprises a housing including a gear chamber and a screw chamber, a screw that extends through the screw chamber and is rotatably coupled within the housing such that the screw is able to rotate about a screw axis within the screw chamber, an indicator ring threaded onto the screw within the screw chamber such that rotation of the screw causes the ring to move up or down the screw a distance along the screw axis, a screw gear positioned within the gear chamber and coupled to an end of the screw and centered around the screw axis such that rotation of the screw gear causes rotation of the screw and an offset gear positioned within the gear chamber offset from the screw axis and operably coupled with the screw gear such that rotation of the gear wheel causes the screw gear to correspondingly rotate, wherein a number of rotations of the screw gear in a direction is proportional to the distance moved by the ring caused by the rotation of the screw gear. In some embodiments, the gear chamber comprises a coupling aperture that extends through the gear chamber in a direction and is non-circular in a plane orthogonal to that direction. In some embodiments, the offset gear has a gear aperture that extends through the gear and aligns with the coupling aperture. In some embodiments, the offset gear comprises a first set of teeth and a second set of teeth, wherein the first set of teeth are operably coupled with the screw gear and the second set of teeth are accessible from outside the gear chamber via the coupling aperture. In some embodiments, the screw chamber comprises a viewing aperture that extends along a length of the screw such that the length of the screw and the ring are visible from outside the screw chamber via the viewing aperture. In some embodiments, the ring at least partially protrudes into the viewing aperture such that the inner walls of the screw chamber defining the viewing aperture prevent the ring from rotating with the screw when the screw rotates within the screw chamber. In some embodiments, the housing comprises a plurality of height lines positioned on an outer surface of the housing along the perimeter of the viewing aperture, wherein the height lines are all orthogonal to the screw axis within the screw chamber. In some embodiments, the outer surface of the housing further comprises a compatibility marker that indicates a type of a bone fusion device whose tab extension or retraction rate is proportional to a distance the ring moves up or down the screw when the screw is rotated.

A fourth aspect is directed to a engaging tool for use in the bone fusion device insertion system. The engaging tool comprises a handle having a base, an elongated member having a first end with a contoured tip and a second end opposite the first end and coupled to the base of the handle and an interface gear having a set of teeth and coupled to the base of the handle such that the set of teeth are centered around the elongated member. In some embodiments, the elongated member has a central axis and the contoured tip is non-circular in a plane orthogonal to the central axis. In some embodiments, the set of teeth protrude away from the base of the handle.

BRIEF DESCRIPTION OF THE DRAWINGS

FIGS. 6A and 6B illustrate a front and a side view of a bone fusion device having one or more protruding tabs according to some embodiments.

FIGS. 7A-7C illustrate a front, side and top view of a bone fusion device having one or more protruding rails according to some embodiments.

FIGS. 11A-11D illustrate perspective, top, front and back views, respectively, of a measuring tool according to some embodiments.

FIGS. 20A-C illustrate an exploded perspective view, a side view and a frontal view, respectively, of a flexible plunger of the plungers according to some embodiments.

FIG. 21 illustrates a method of operation of the bone fusion system according to some embodiments.

DETAILED DESCRIPTION

In the following description, numerous details and alternatives are set forth for purpose of explanation. However, one of ordinary skill in the art will realize that the invention can be practiced without the use of these specific details. For instance, the figures and description below often refer to the vertebral bones of a spinal column. However, one of ordinary skill in the art will recognize that some embodiments of the invention are practiced for the fusion of other bones, including broken bones and/or joints. In other instances, well-known structures and devices are shown in block diagram form in order not to obscure the description of the invention with unnecessary detail.

Figure 1A:
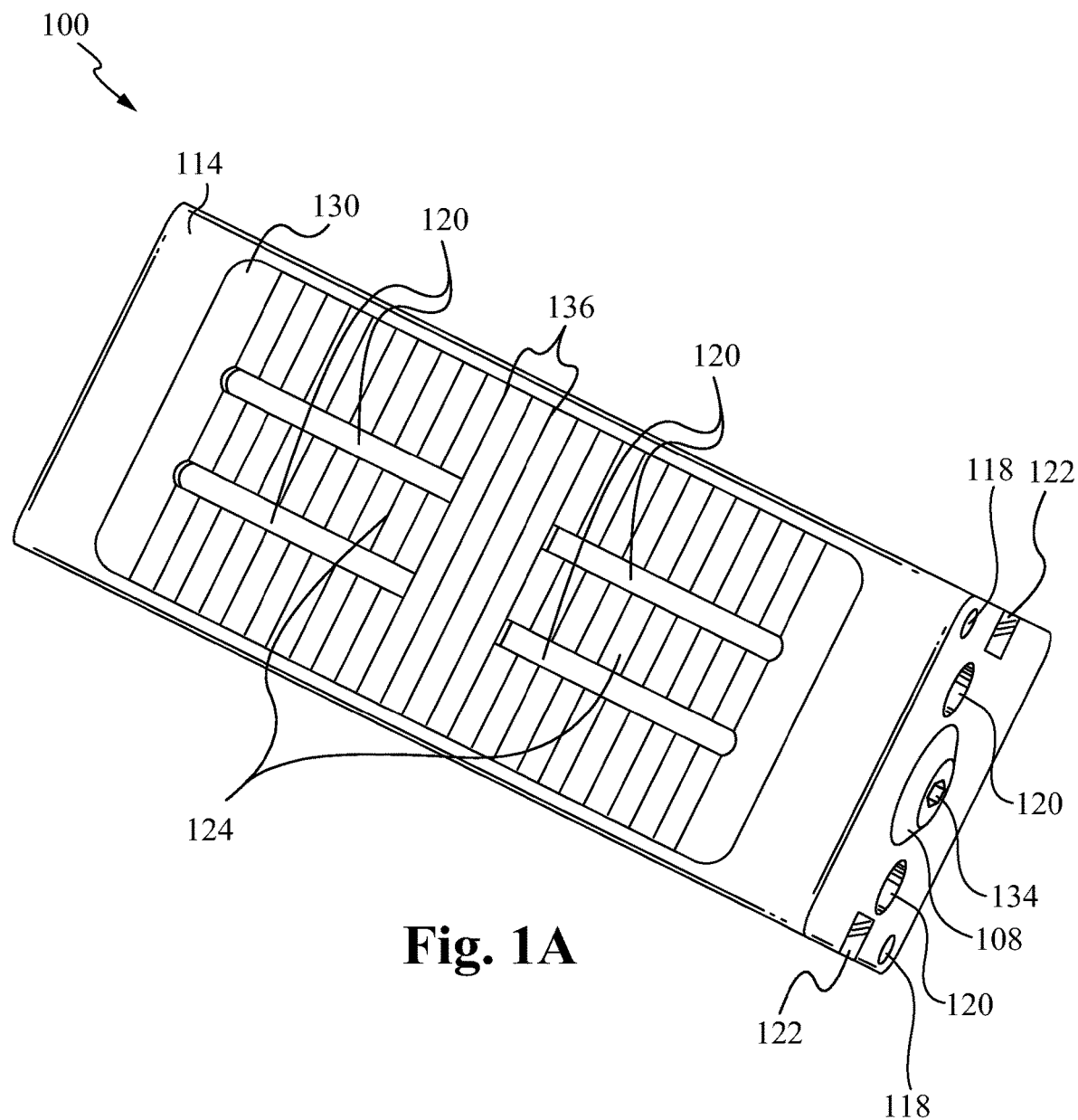
FIG. 1A illustrates a top perspective view of the bone fusion device according to some embodiments.
Figure 1B:
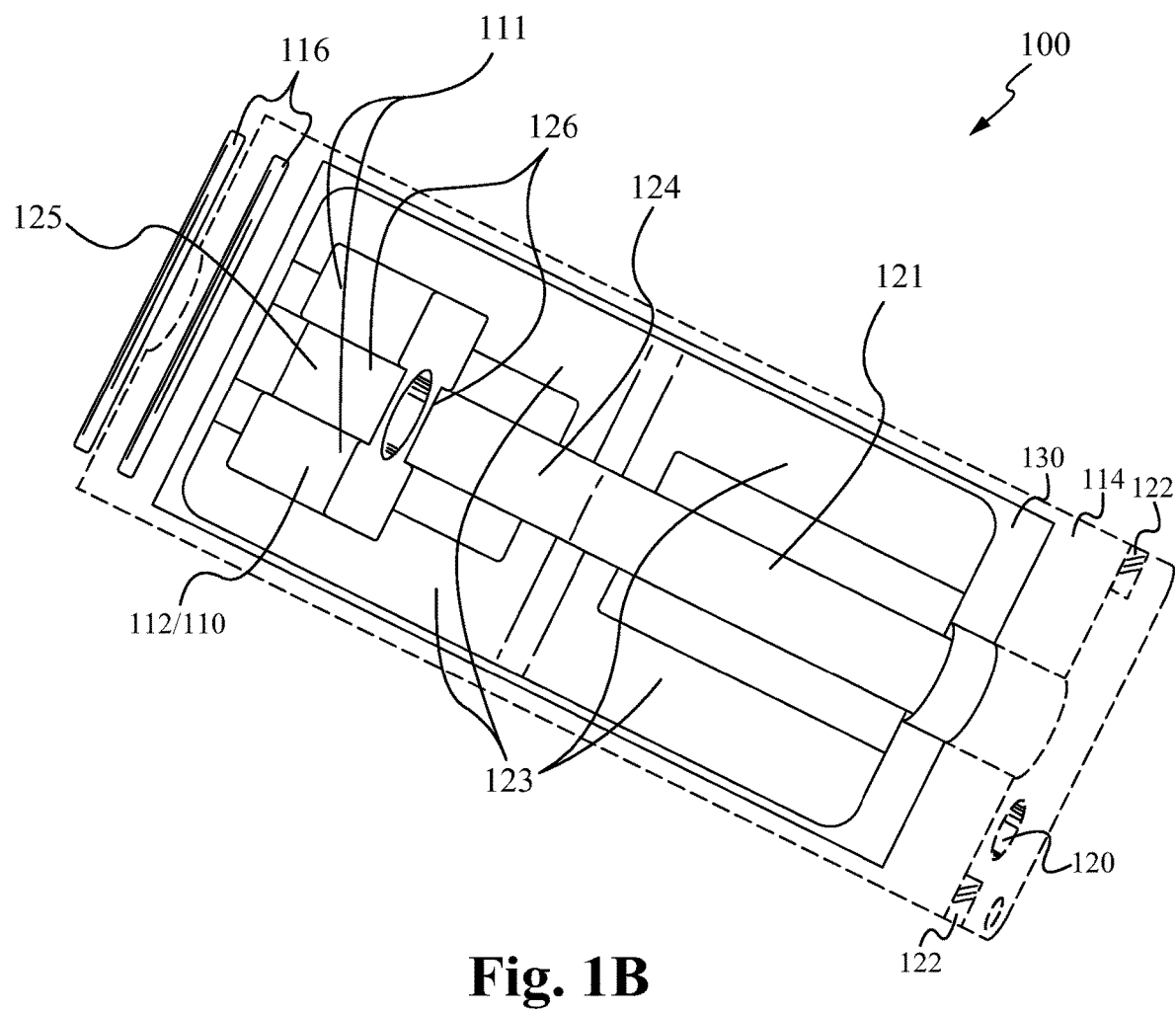
FIG. 1B illustrates a top cutout view of the bone fusion device according to some embodiments.

FIGS. 1A and 1B illustrate a top perspective and cutout view of the bone fusion device 100 according to some embodiments. As shown, the bone fusion device 100 has a substantially rectangular shape and has two end faces. The bone fusion device 100 is able to be constructed from a high strength biocompatible material, such as titanium, which has the strength to withstand forces in the spine that are generated by a patient's body weight and daily movements. Alternatively, part of all of the bone fusion device 100 is able to be constructed from one or more of the group consisting of high strength biocompatible material or a polymer such as PEEK, PEKK, and other polymeric materials know to be biocompatible and having sufficient strength. In some embodiments, the materials used to construct the bone fusion device include using additives, such as carbon fibers for better performance of the materials under various circumstances. The base biocompatible material is often textured or coated with a porous material conducive to the growth of new bone cells on the bone fusion device 100. In some embodiments, the porous material or coating is able to be a three-dimensional open-celled titanium scaffold for bone and tissue growth (e.g. an OsteoSync structure). For example, the coating is able to be a osteosync structure having a mean porosity of 50-70%, pore sizes ranging from 400-700 µm, and/or a mean pore interconnectivity of 200-300 µm. Alternatively, instead of a coating on the bone fusion device 100, the porous material is able to be integrated into the frame and component of the bone fusion device 100. The bone fusion device 100 is able to have several conduits or holes 120 (also see FIG. 2) which permit the bone graft material to be inserted into the device 100 and to contact the vertebral bone before or after the device 100 has been inserted between the vertebrae of the patient. The bone graft material and the surface texturing (e.g. porous material coating) of the device 100 encourage the growth and fusion of bone from the neighboring vertebrae. The fusion and healing process will result in the bone fusion device 100 aiding in the bridging of the bone between the two adjacent vertebral bodies of the spine which eventually fuse together during the healing period.

As further illustrated in FIGS. 1A and 1B, tabs 130 are located on opposing sides of the bone fusion device 100. The tabs 130 are shaped so that their outer surface is substantially flush with the frame 114 of the bone fusion device 100 in a nonextended position. Internally, the tabs 130 have a full or partial central rib 124 and an angled inner surface. Specifically, the central rib 124 is configured to provide further outer surface area and structural support to the tabs 130. Further, each tab 130 is shaped such that one or more angled surfaces 123 of the tab 130 for extending the tab 130 have end thicknesses that are larger than their middle thicknesses such that the thickness of the angled surfaces 123 gradually increases while going from the middle to the ends of the tab 130. A positioning component 108 within the frame 114 of the bone fusion device 100 comprises a positioning aperture 134, a first screw 102 and a second screw 104 coupled together (see FIGS. 4A and 4B). The positioning aperture 134 is configured to receive a drive/engaging mechanism of a tool such that the tool is able to rotate or otherwise manipulate the positioning component 108. The positioning aperture 134 is able to comprise numerous shapes and sizes as are well known in the art. The first screw 102 is threaded opposite of the second screw 104. For example, if the first screw 102 is left threaded, the second screw 104 is right threaded or vice-versa. Furthermore, the first screw 102 (see FIG. 2) is of a slightly different size than the second screw 104. The positioning component 108 is coupled to a first extending block 110 and a second extending block 112, each having a pair of rib slots 126 configured to receive the central ribs 124 of the tabs 130 (see FIG. 1B). Specifically, the rib slots 126 are sized such that they permit the central ribs 124 to slide into and out of the slots 126 (depending on the position of the blocks 110, 112) such that when positioned within the slots 126, the blocks 110, 112 are able to support the tabs 130 against torsional forces by holding and supporting the central ribs 124.

Further, the first extending block 110 is coupled to the first screw 102 and the second extending block 112 is coupled to the second screw 104, and the first extending block 110 and the second extending block 112 are positioned in the middle of the bone fusion device 100 in the compact position. When the positioning component 108 is turned appropriately, the extending blocks 110 and 112 each travel outwardly on their respective screws 102 and 104. As the extending blocks 110 and 112 travel outwardly, they push the tabs 130 outward and the central ribs 124 slide within the rib slots 126. In other words, the inner tab surface 123 when in contact with the extending blocks 110, 112 act in such a manner so as to push the respective tabs 130 apart. Specifically, the angled surfaces 111 of each extending block 110, 112 are able to be in contact with the tab surfaces 123 and the center rib surface 121 is in contact with the extending block slot surface 125. Thus, the tabs 130 will be fully extended when the extending blocks 110 and 112 reach the opposite ends of the screws 102, 104. To retract the tabs 130, the positioning device 108 is turned in the opposite direction and the extending blocks 110 and 112 will each travel back to the middle on their respective screws 102 and 104 with the central ribs 124 within the rib slots 126 enabling the tabs 130 to move into the retracted position due to gravity or another downward force. When the extending blocks 110 and 112 are positioned in the middle of the bone fusion device 100, the tabs 130 are compact and are within the frame 114 of the bone fusion device 100. In some embodiments, the extending blocks 110 and 112 are coupled to the tabs 130 such that they apply the needed downward force to retract the tabs. Alternatively, the tabs 130 are able to be biased with a biasing mechanism that applies the downward force needed to cause the tabs 130 to retract when enabled by the position of the extending blocks 110, 112. For example, one or more springs are able to be coupled to the tabs 130, wherein the springs apply a retraction biasing force to the tabs 130 that causing the tabs to retract when enabled by the extending blocks 110, 112.

It is contemplated that the operation of the device 100 is able to be reversed such that the tabs 130, extending blocks 110, 112, and positioning components 108 are configured such that the extending blocks 110, 112 travel inwardly to extend the tabs 130 into the extended position and travel outwardly to retract the tabs 130 into the compact position. Further, it is contemplated that the positioning component 108 is able to be a non-rotational or other type of force generating mechanism that is able to move the extending blocks 110, 112. For example, the positioning component 108 is able to be a mechanism where a non-rotational movement (e.g. in/out of the device 100) causes the movement of the extending blocks 110, 112. In any case, the nonextended tabs 130 of the bone fusion device 100 provide a compact assembly that is suitable for insertion into the patient's body through a open, or minimally invasive surgical procedure. As used herein, an open or a minimally invasive procedure comprises a procedure wherein a smaller surgical incision is employed as compared to the size of the incision required for conventional invasive surgery, for example, arthroscopic procedures. Moreover, minimally invasive procedures minimize or eliminate the need for excessive retraction of a patient's tissues such as muscles and nerves, thereby minimizing trauma and injury to the muscles and nerves and further reducing the patient's recovery time.

Figure 3:
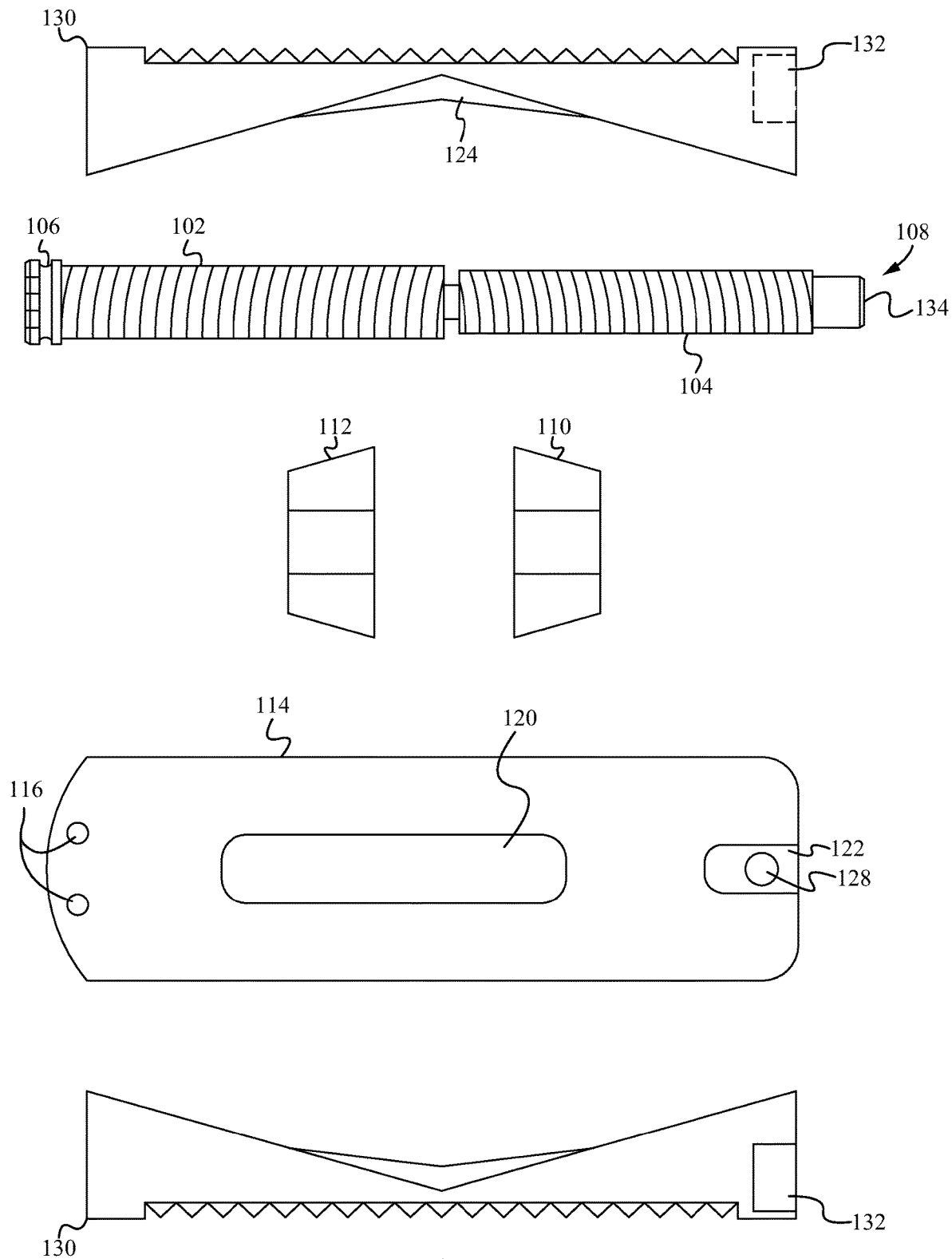
FIG. 3 illustrates a cross-sectional view of components of the bone fusion device according to some embodiments.

As the positioning component 108 is rotated causing the extending blocks 110 and 112 to move closer to the ends of the respective screws 102 and 104, the extending blocks 110 and 112 push the tabs 130 outward causing the tabs 130 to assert pressure against surrounding bones and securing the bone fusion device 100 in place. When the extending blocks 110 and 112 reach as close to the end of the positioning components 108 as allowed, the tabs 130 are fully extended. Furthermore, since the extending blocks 110 and 112 travel along the positioning components 108, along the threads of the screws 102 and 104, very precise positions of the tabs 130 are able to be achieved. The tabs 130 are able to have serrated edges or teeth 136 to further increase the bone fusion device's gripping ability and therefore ability to be secured in place between the bones for both a long-term purchase and a short-term purchase. In some embodiments, the serrated edges or teeth 136 are able to be in a triangular or form a triangular wave formation as shown in FIG. 3. Alternatively, the serrated edges or teeth 136 are able to be filleted, chamfered, or comprise other teeth shapes or edge waves as are well known in the art. In some embodiments, the device 100 is able to comprise a position locking mechanism that helps prevent the positioning component 108 from slipping. In particular, the locking mechanism is able to be substantially similar to those described in U.S. patent application Ser. No. 14/210,094, filed on Mar. 13, 2014 and entitled "BODILESS BONE FUSION DEVICE, APPARATUS AND METHOD," which is hereby incorporated by reference. In some embodiments, the locking mechanism is able to be positioned within a side wall of the frame 114 around the around the positioning aperture 134 instead of being within a support panel of the device 100.

To secure the bone fusion device 100 in place, a user generally utilizes an insertion instrument such as a screw driver to turn the positioning components 108. Screw drivers unfortunately have the ability to slip out of place. When performing surgery near someone's spine, it is preferable to prevent or at least minimize the slipping ability. Further, it is necessary to ensure that the surgeon is able to precisely place and control the device via a robust connection to the device. To do so, channels 122 having gripping apertures 128 are implemented to receive gripping fingers of a tool/insertion instrument (not shown) such that the tool cannot slip out of place during operation. Specifically, the channels 122 are sized to receive the fingers to prevent the tool from moving laterally with respect to the head of the positioning components 108 and the gripping apertures 128 are sized to receive the fingertips of the fingers of the tool such that the fingers (and tool) are unable to unintentionally be pulled out of the channels 122 (and positioning components 108). In some embodiments, the channels 122 are aligned such that they are at the same height on opposite sides of the frame 114 of the device 100. Alternatively, the channels 122 are able to be offset (e.g. not at the same height). Alternatively, the channels 122 are able to positioned on other portions of the frame 114. In operation, a surgeon causes the fingers of the tool to spread as the are inserted into the channels 122, and then the surgeon causes the fingers to clamp together inserting the fingertips of the fingers into the gripping apertures 128 and fully securing the tool onto the device 100. Thus, the tool is unable to slip out of place and is only able to be removed upon the spreading of the fingers such that the fingertips are removed from the apertures 128 and the fingers are removed from the channels 122. Furthermore, if the device 100 is next to relatively immovable tissue (e.g. bone, ligament or tendon under load), then this device 100 will still be able to disengage, whereas one that relies on clamping by bending two rods together will not work if one of the rods is restricted by the relatively immovable tissue.

Figure 2:
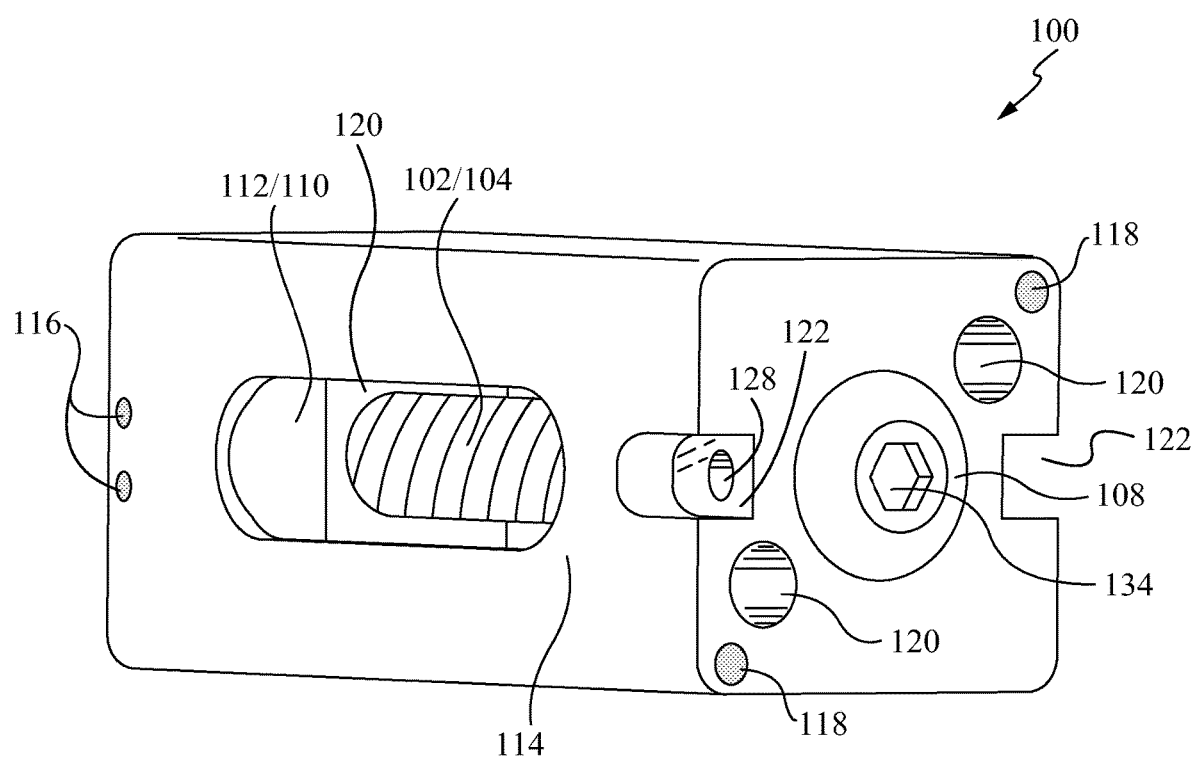
FIG. 2 illustrates a side perspective view of the bone fusion device according to some embodiments.

FIG. 2 illustrates a side perspective view of the bone fusion device 100 according to some embodiments. The bone fusion device 100 utilizes the positioning components 108 comprising the first screw 102 and the second screw 104 to move the first extending block 110 and the second extending block 112 outwardly from the middle of the bone fusion device 100 towards its ends. The positioning component 108 is held in place but permitted to turn utilizing one or more first pins 116. The one or more first pins 116 are secured within a retaining groove 106 (FIG. 3) of the positioning component 108. The extending blocks 110 and 112 force the tabs 130 to either extend or retract depending on where the extending blocks 110 and 112 are positioned. As described above, the tabs 130 are able to have serrated edges or teeth 136 to further increase gripping ability. The tabs 130 are each coupled to the frame 114 of the bone fusion device 100 by one or more pin slots 132 (FIGS. 3 and 4A) and one or more second pins 118 wherein the one or more second pins 118 fit within the one or more pin slots 132 and are able to travel along the interior of the one or more pin slots 132. In some embodiments, each tab 130 is secured with a single second pin 118 and pin slot 132. Alternatively, one or more of the tabs 130 are able to have multiple second pins 118 and pin slots 132. In some embodiments, the multiple pin slots 132 are able to be positioned at the corners of the tabs 130 similar to the single pin slot 132 shown in FIG. 3. In some embodiments, the multiple pin slots 132 of tabs 130 are symmetric such that any tab 130 is able to be placed on the top or bottom of the bone fusion device 100. Alternatively, the pin slots 132 of the tabs 130 are able to be positioned anywhere on the tab 130 and/or be positioned asymmetrically. In some embodiments, the pins/pin slots 118/132 are able to be replaced by or supplemented with one or more biasing elements positioned within biasing channels within the tabs 130 and/or frame 114 and thereby biasing the tabs 130 in the retracted position. In particular, the channels and/or biasing elements are able to be substantially similar to those described in U.S. patent application Ser. No. 14/210,094, filed on Mar. 13, 2014 and entitled "BODILESS BONE FUSION DEVICE, APPARATUS AND METHOD."

The holes/conduits 120 within the tabs 130 allow the bone graft material to contact the vertebral bone after the device 100 has been inserted between the vertebrae of the patient. A set of holes/conduits 120 within the frame 114 also allow bone graft material to be inserted within the bone fusion device 100 after the bone fusion device 100 has been placed. Specifically, as shown in FIG. 2, the side of the frame 114 has an elongated hole 120 exposing the positioning component 108 and extending blocks 112/110. This elongated hole 120 is able to serve as a channel for pushing bone graft material into the frame 114 once it is in position. In some embodiments, there is a matching elongated hole 120 on the opposite side of the frame 114 such that the bone graft material is able to be added from either side using the hole 120 on that side. In some embodiments, the channels 122 have gripping apertures 128 implemented to receive a tool. Alternatively, the gripping apertures 128 are able to be omitted.

FIG. 3 illustrates a cross-sectional view of components of the bone fusion device 100 according to some embodiments. As described above, the positioning component 108 comprises a first screw 102 and a second screw 104 wherein the first screw 102 is threaded differently than that of the second screw 104. Furthermore, the first screw 102 is of a slightly different size than the second screw 104. For example, in some embodiments the first screw 102 is an 8-32 screw and the second screw is a 6-32 screw. A retaining groove 106 is utilized to secure the positioning component 108 in place. In some embodiments, the retaining groove 106 is positioned opposite the end of the positioning component 108 having the positioning aperture 134. To ensure that the tool does not slip while turning the positioning component 108, the channels 122 having fingertip gripping apertures 128 are utilized to secure the tool as described above. Alternatively, the fingertip gripping apertures 128 are able to be omitted and the channels 122 are able to secure the tool as described above. A first extending block 110 and a second extending block 112 are utilized with the positioning component 108 to extend and compact one or more of tabs 130. The first extending block 110 has an internal opening and threading to fit around the first screw 102. The second extending block 112 has an internal opening and threading to fit around the second screw 104. As described above, the frame 114 of the bone fusion device 100 contains a set of holes/conduits 120 within the frame 114 for allowing bone graft material to be inserted. Furthermore, one or more first pins 116 secure the positioning component within the frame 114. One or more second pins 116 in conjunction with one or more pin slots 132 secure the tabs 130 to the frame 114.

Figure 4A:
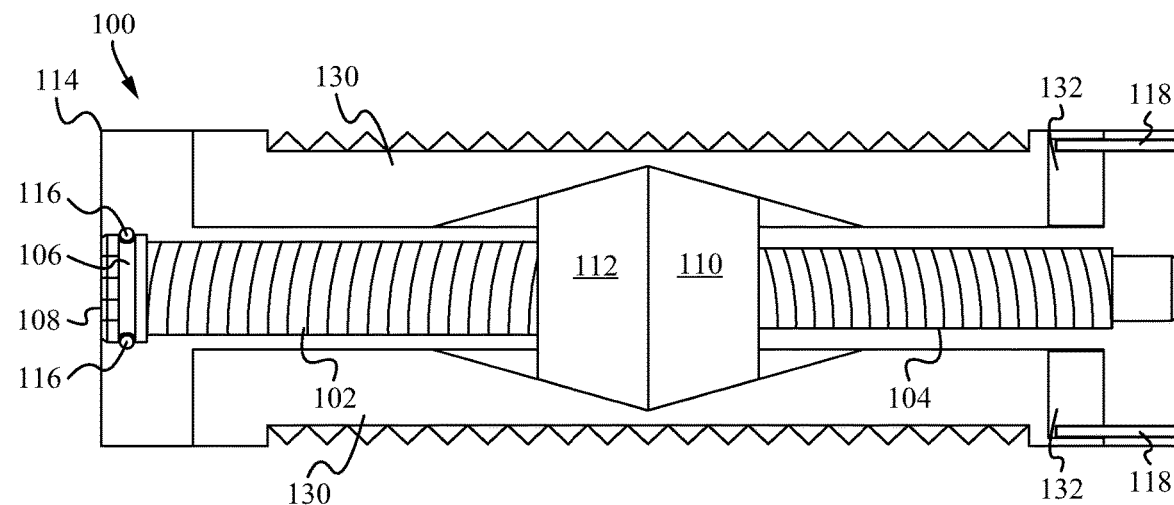
FIG. 4A illustrates a cross sectional view of the bone fusion device with the tabs compacted according to some embodiments.

FIG. 4A illustrates a cross sectional view of the bone fusion device 100 with the tabs retracted according to some embodiments. When the extending blocks 110 and 112 are positioned in the middle of the positioning component 108 with the first screw 102 and the second screw 104, the tabs 130 are positioned within the frame 114 of the bone fusion device 100 with the central ribs 124 slid within the rib slots 126. The retaining groove 106 holds the positioning component 108 in place with one or more first pins 116. The tabs 130 are coupled to the frame 114 of the bone fusion device 100 using the one or more slots 132 and the one or more second pins 118 wherein the one or more second pins 118 fit within the one or more slots 132 and are able to travel/slide along the interior of the one or more slots 132.

Figure 4B:
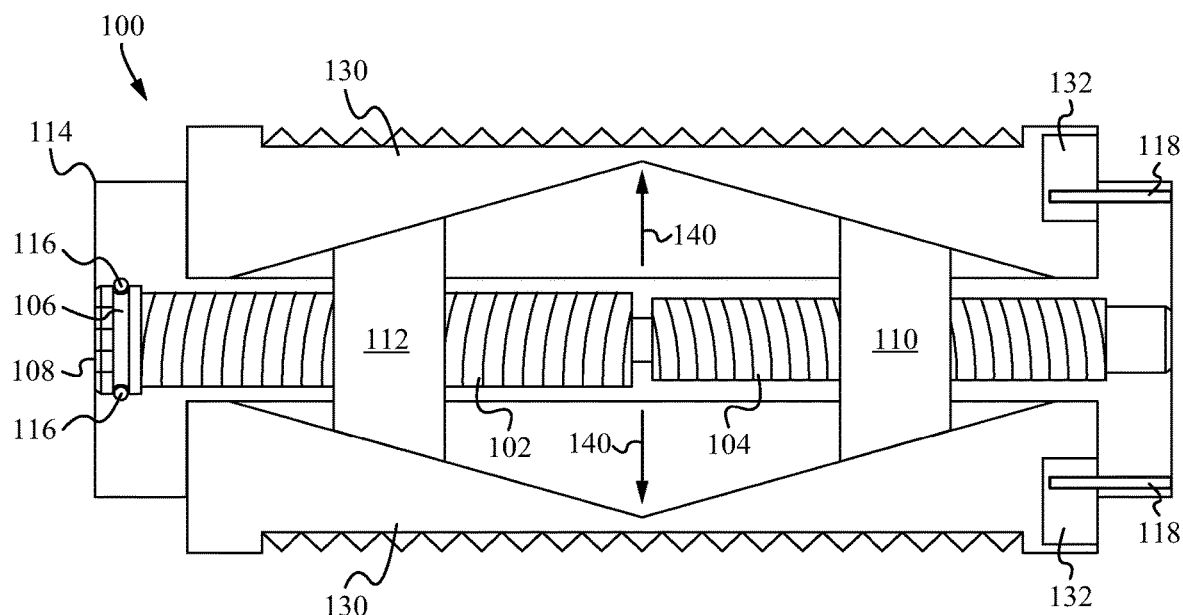
FIG. 4B illustrates a cross sectional view of the bone fusion device with the tabs extended according to some embodiments.

FIG. 4B illustrates a cross sectional view of the bone fusion device 100 with the tabs extended according to some embodiments. As shown in FIG. 4A, the bone fusion device 100 is compressed/contracted when the extending blocks 110 and 112 are in the middle of the bone fusion device 100. As a user turns the positioning component 108 via the positioning aperture 134, the extending blocks 110 and 112 gradually move outward from the middle. If the user turns the positioning component 108 in the opposite direction, the extending blocks move back towards the middle. As the extending blocks 110 and 112 are moving outward, the central ribs 124 slide out of the rib slots 126 and the extending blocks 110, 112 push on the tabs 130. Alternatively, the cental ribs 124 and/or rib slots 126 are able to be configured such that the central ribs 124 are fully within the rib slots 126, fully removed from the rib slots 126, or somewhere in between at any point along the path of the extending blocks 110, 112 from the center of the device to the ends of the device. The tabs 130 extend because the extending blocks 110 and 112 exert force against the angled tabs 130 outwardly as shown by the arrows 140. When the extending blocks 110 and 112 are positioned near the ends of the bone fusion device 100, the tabs 130 extend beyond the frame 114 of the bone fusion device 100 and ultimately secure the bone fusion device 100 between two bones. With the tabs 130 coupled to the frame 114 of the bone fusion device 100 by the one or more slots 132 and the one or more second pins 118, the tabs 130 are able to extend beyond the frame 114 of the bone fusion device 100 as the one or more second pins 118 travel within the interior of the one or more slots 132.

In operation, the bone fusion device 100 is initially configured in a compact position such that the extending blocks 110, 112 are located in the middle of the bone fusion device 100 thereby allowing the tabs 130 to rest within the frame 114 of the bone fusion device 100. The compact bone fusion device 100 is then inserted into position within the patient. The surgeon is able to then the expand the bone fusion device 100 by rotating the positioning component 108 which moves the extending blocks 110, 112 towards the opposing ends of the bone fusion device 100—one near the head of the positioning component 108 and the other towards the tail of the positioning component. As the extending blocks 110, 112 move away from the middle, the tabs 130 are pushed outwardly from the pressure of the extending blocks 110, 112 against the angled tabs 130. Initially, the central ribs 124 of the tabs 130 remain at least partially within the rib slots 126 of the extending blocks 110, 112 such that the blocks 110, 112 are able to resist torsional forces on the tabs 130 and/or device 100. Gradually, the central ribs 124 slide out of the rib slots 126 as the extending blocks 110, 112 approach the ends of the positioning component 108. Alternatively, the central ribs 124 are able to be configured such that they remain at least partially within the rib slots 126 as the extending blocks 110, 112 approach the ends of the positioning component 108. Eventually the extending blocks 110, 112 exert a satisfactory force between the extended tabs 130 and the bones to be fused. At that point the bone fusion device 100 is able to remain in place. Thereafter, material for fusing the bones together (e.g. bone graft material) is inserted through the holes and openings 120 within the bone fusion device 100. Alternatively, the insertion of the material for fusing the bones together is able to be omitted.

Figure 5:
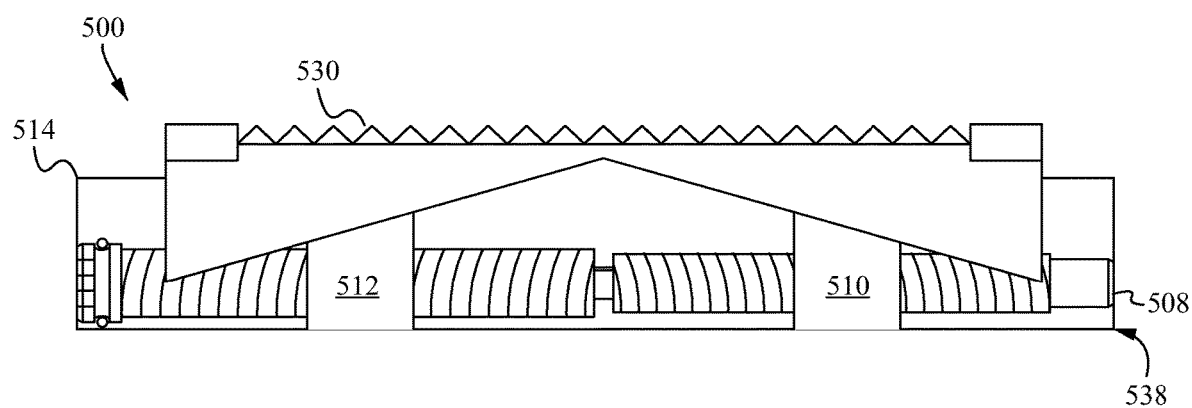
FIG. 5 illustrates a profile view of a bone fusion device having a single tab extension/retraction mechanism according to some embodiments.

FIG. 5 illustrates a bone fusion device 500 having a single tab extension/retraction mechanism according to some embodiments. The bone fusion device 500 shown in FIG. 5 is substantially similar to the bone fusion device 100 except for the differences described herein. In particular, the bone fusion device 500 comprises a half frame 514, one or more half extending blocks 510, 512, a tab 530 and positioning component 508. Similar to the bone fusion device 100, the half extending blocks 510, 512 are coupled around the positioning component 508 such that when the positioning components 508 are turned, the blocks 510, 512 move outwards causing the tab 530 to move to the extended position. The half frame 514 comprises a tab aperture (see FIG. 1A) for receiving the tab 530 and a solid floor 538 opposite the tab aperture. In some embodiments, the floor 538 is able to have one or more floor holes/conduits for receiving/distributing grafting material into and out of the device 500. In some embodiments, the device 500 is sized such that when the tab 530 is in the compact/retracted position the distance between the top of the tab 530 and the floor 538 is less than or equal to 5 mm, and when the tab 530 is in the extended position the distance between the top of the tab 530 and the floor 538 is less than or equal to 7 mm. Alternatively, the device 500 is sized such that when the tab 530 is in the compact/retracted position the distance between the top of the tab 530 and the floor 538 is in the range of 5 mm to 13 mm and when the tab 530 is in the extended position the distance between the top of the tab 530 and the floor 538 is in the range of 7 mm to 22 mm. Alternatively, other sizes of the device 500 are contemplated as are well known in the art. Thus, by including only a single tab 530, the height of the device 500 is able to be minimized. As a result, the bone fusion device 500 enables surgeons to use smaller incisions as well as to fit the bone fusion device 500 into smaller places and increasing the versatility of the device 500. Additionally, it should be noted that the single tab extension/retraction mechanism described in FIG. 5 is able to replace each of the dual or multiple tab extension/retraction mechanisms described herein wherein the devices having dual tab extension/retraction mechanisms are essentially halved (except for the positioning component) such that only one tab is remaining.

FIGS. 6A and 6B illustrate a front and a side view of a bone fusion device 600 having one or more protruding tabs according to some embodiments. The bone fusion device 600 shown in FIGS. 6A and 6B is substantially similar to the bone fusion device 100 except for the differences described herein. In particular, the bone fusion device 600 comprises one or more tabs 630 having a height such that even when fully retracted an outer end or surface 602 of the tabs 630 extends beyond the plane or face of the frame 614. For example, the outer end or surface 602 is able to comprise the outwardly pointing teeth 636 and/or other most outward portions of the tabs 630. As a result, when placed between two bones (e.g. vertebra) before being extended, the teeth 636 or other portions of the surface 602 of the bottom facing tab 630 are able to provide traction with the bone surface such that the device 600 does not slip out of place when the tabs 630 are being extended. In some embodiments, only one of the tabs 630 extends beyond the face of the frame 614 in the fully retracted position. Alternatively, two or more of the tabs 630 (e.g. all of the tabs) extend beyond the face of the frame 614 in the fully retracted position. In some embodiments, only a portion (not the full length) of the outward face or end 602 of the tabs 630 extend beyond the face of the frame 614 in the fully retracted position. Alternatively, the full length of the outward face or end 602 of the tabs 630 is able to extend beyond the face of the frame 614 in the fully retracted position. In some embodiments, the tabs 630 extend 0.25 millimeters beyond the face of the frame 614 in the fully retracted position. Alternatively, one or more of the tabs 630 are able to extend more or less than 0.25 millimeters (e.g. 0.1 mm) beyond the face of the frame 614 in the fully retracted position. Additionally, although as shown in FIGS. 6A and 6B the device 600 comprises two tabs 630 and all of the tabs 630 have ends 602 that extend beyond the face of the frame 614 in the fully retracted position, the device 600 is able to comprise any number of tabs 630 (e.g. one or more) wherein one or any combination of a plurality of the tabs 630 are able to have ends 602 that extend beyond the face of the frame 614 in the fully retracted position. Further, as described above, one or more of the components of the bone fusion device 600 are able to be incorporated into one or more of the other embodiments of bone fusion devices described herein.

Figure 7C:
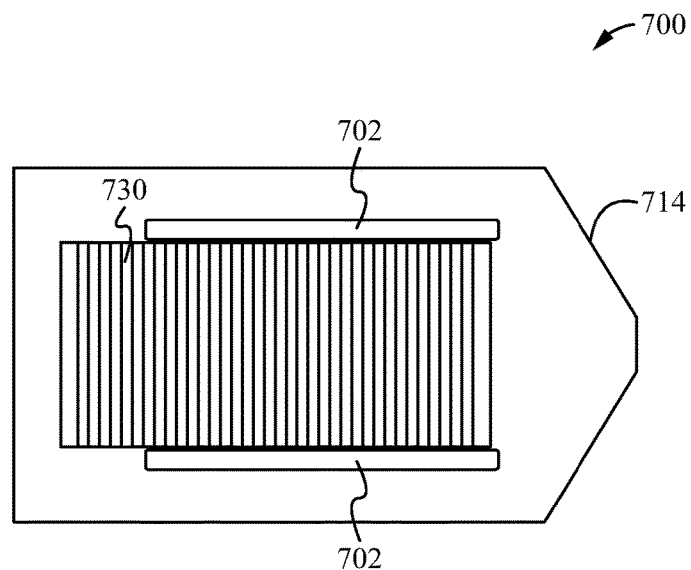

FIGS. 7A-7C illustrate a front, side and top view of a bone fusion device 700 having one or more protruding rails according to some embodiments. The bone fusion device 700 shown in FIGS. 7A-7C is substantially similar to the one or more of the other embodiments of bone fusion devices (e.g. bone fusion device 100) except for the differences described herein. In particular, the bone fusion device 700 comprises one or more rails 702 adjacent to one or more of the tabs 730 that protrude above the plane or face of the frame 714. For example, as shown in FIGS. 7A-7C, two rails 702 are positioned next to opposite sides/edges of each of the tabs 730. As a result, the rails 702 provide the advantage of preventing a protruding portion of one or more of the tabs 730 or other parts of the device 700 from catching on anything during insertion of the device 700 into position. In some embodiments, the rails 702 are utilized in conjunction with protruding tabs 630 as shown in FIGS. 6A and 6B. Alternatively, the rails 702 are able to be used in conjunction with protruding tabs, non-protruding tabs, other types of tabs described herein and/or any combination thereof. In some embodiments and as shown in FIGS. 7A-7C, the rails 702 only extend along a portion (not the entire length) of an edge of the perimeter of one or more of the tabs 730. As a result, those portions of the edges of the perimeter of the one or more of the tabs 730 will be guarded by the rails 702 whereas the remainder of the edges will not be guarded. In particular, if the tabs 730 are protruding tabs 630, despite protruding beyond the frame 714, as described above, the guarded portion of the ends 602 of the protruding tabs 630 will still be adjacent to the rails 702 whereas the unguarded portion of the ends 602 will extend beyond the face of the frame 714 without any adjacent rails 702.

In some embodiments, one or more of the rails 702 are able to have length such that they extend the full length of a side or sides of the perimeter of one of the tabs 730. For example, a rail 702 is able to form a ring such that it extends the entire perimeter of one of the tabs 730. As another example, one or more rails 702 are able to extend around the corners created by two or more of the sides of the perimeter of one of the tabs 730. In such embodiments, the rails 702 are able to make perpendicular and/or rounded turns in order to wrap around the multiple sides. Alternatively or in addition, one or more of the rails 702 are able to have length such that they do not extend the full length of a side or sides of the perimeter of one of the tabs 730 and/or one or more of the rails 702 are able to be discontinuous such that there are gaps between one or more portions of the one or more of the rails 702. In some embodiments, a plurality of rails 702 are able to be next to the same side of the perimeter of one of the tabs 730. In other words, two or more rails 702 next to the same side are able to be the same or different lengths and/or be aligned or otherwise overlap in the portions of the perimeter of the tab 730 that they are next to. In some embodiments, the positioning of the rails 702 next to the tabs 730 is biased toward the front of the device 700 (e.g. away from the side where the positioning component is accessible). For example, as shown in FIGS. 7A-7C, the rails 702 start at the front leading edge of the tabs 730 such that when the device 700 is inserted frontwards the rails will guard the front leading edge of the tabs 730 from getting caught during the insertion.

In some embodiments, a portion or all of one or more of the rails 702 are able to directly abut the edge of the tabs 730. Alternatively or in addition, a portion or all of one or more of the rails 702 is able to be spaced away from the edges of the tab 702 somewhere along the side of the frame 714 from which the tab 702 is able to extend. In some embodiments, one or more of the rails 702 form lines that are parallel or non-parallel with the closest edge of the tab 730. Alternatively, one or more of the rails 702 are able to be partially or wholly non-linear (e.g curved). In some embodiments, the rails 702 are positioned in matching or mirroring pairs around one or more of the tabs 730. For example, as shown in FIGS. 7A-C each of the tabs 730 have a pair of matching rails 702 that straddle the tab 730 along a portion of the longer edges of the perimeter of the tab 702, wherein the portion is the part of the longer edges closest to the front of the device 700. Alternatively, the one or more rails 702 next to a tab 730 are able to be asymmetric.

In some embodiments, one or more of the rails 702 are coupled to the sides of the frame 714 next to the tabs 730. Alternatively or in addition, one or more of the rails 702 are able to be integrated into the frame 714 itself (e.g a protrusion of the frame 714 itself). In some embodiments, one or more of the rails 702 extend 0.25 millimeters beyond the face of the frame 714 in the fully retracted position. Alternatively, one or more of the rails 702 are able to extend more or less than 0.25 millimeters (e.g. 0.1 mm) beyond the face of the frame 714 in the fully retracted position. Indeed, one or more of the rails 702 are able to be positioned anywhere along the perimeter of one or more of the tabs 730, wherein the perimeter includes the side, plane or face of the frame 714 that surrounds the outwardly facing face of the tabs 730. Additionally, as described above, one or more of the components of the bone fusion device 700 are able to be incorporated into one or more of the other embodiments of bone fusion devices described herein.

Insertion Apparatus

Figure 8:
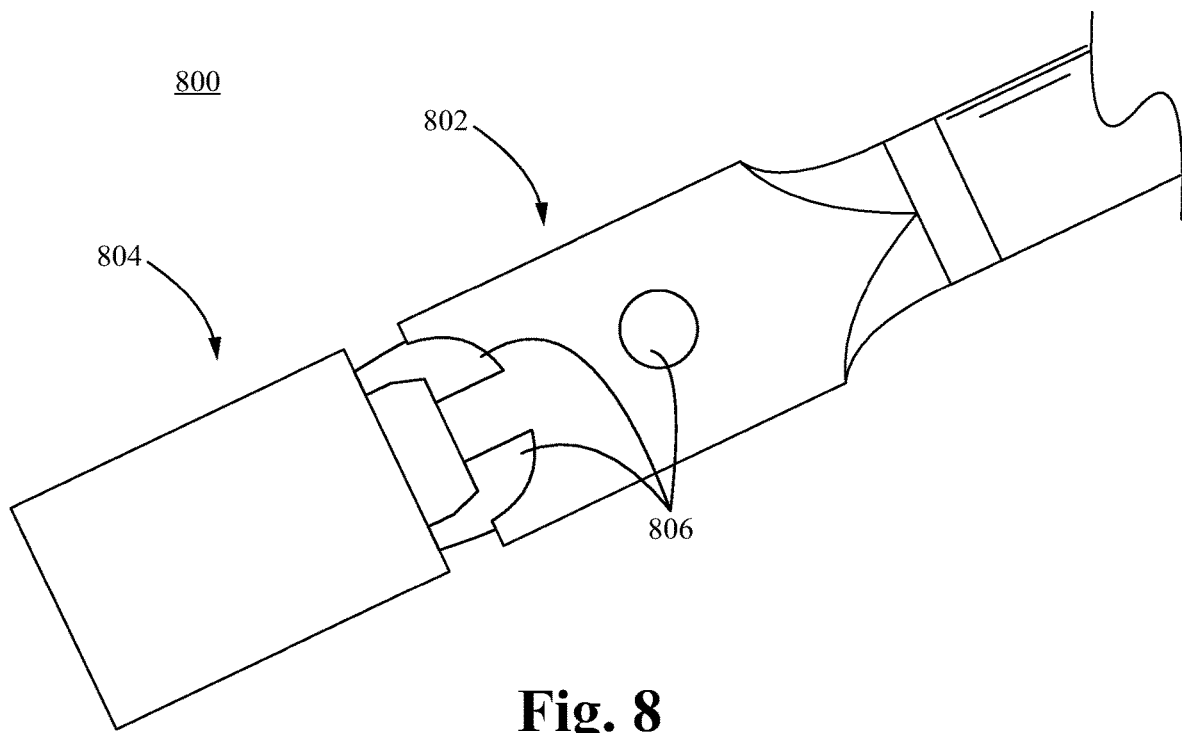
FIG. 8 illustrates a bone fusion apparatus according to some embodiments.

FIG. 8 illustrates a bone fusion device insertion apparatus 800 according to some embodiments. As shown in FIG. 8, the bone fusion apparatus 800 comprises a bone fusion insertion instrument 802 detachably coupled to a bone fusion device 804 via a coupling mechanism 806. In some embodiments, the bone fusion device 804 is substantially similar to the bone fusion device 100 described in FIGS. 1-7. Alternatively, the bone fusion device 804 is able to be other embodiments of bone fusion devices described herein or other types of bone fusion devices as are well known in the art. In some embodiments, the other types of bone fusion devices are able to be formed by one or more of polymers, bone, synthetic bone, metal or other biocompatible materials as are well known in the art. In some embodiments, the coupling mechanism 806 comprises a clamping mechanism. Alternatively, the coupling mechanism 806 is able to comprise any combination of a clamps, screws, locks, adhesives or other attachment elements as are well known in the art. In some embodiments, the insertion instrument 802 is able to detachably couple to a plurality of bone fusion devices 804 simultaneously such that the plurality of devices 804 are able to be simultaneously controlled (e.g. extension/contraction of the tabs) by the single insertion instrument 802.

Figure 9A:
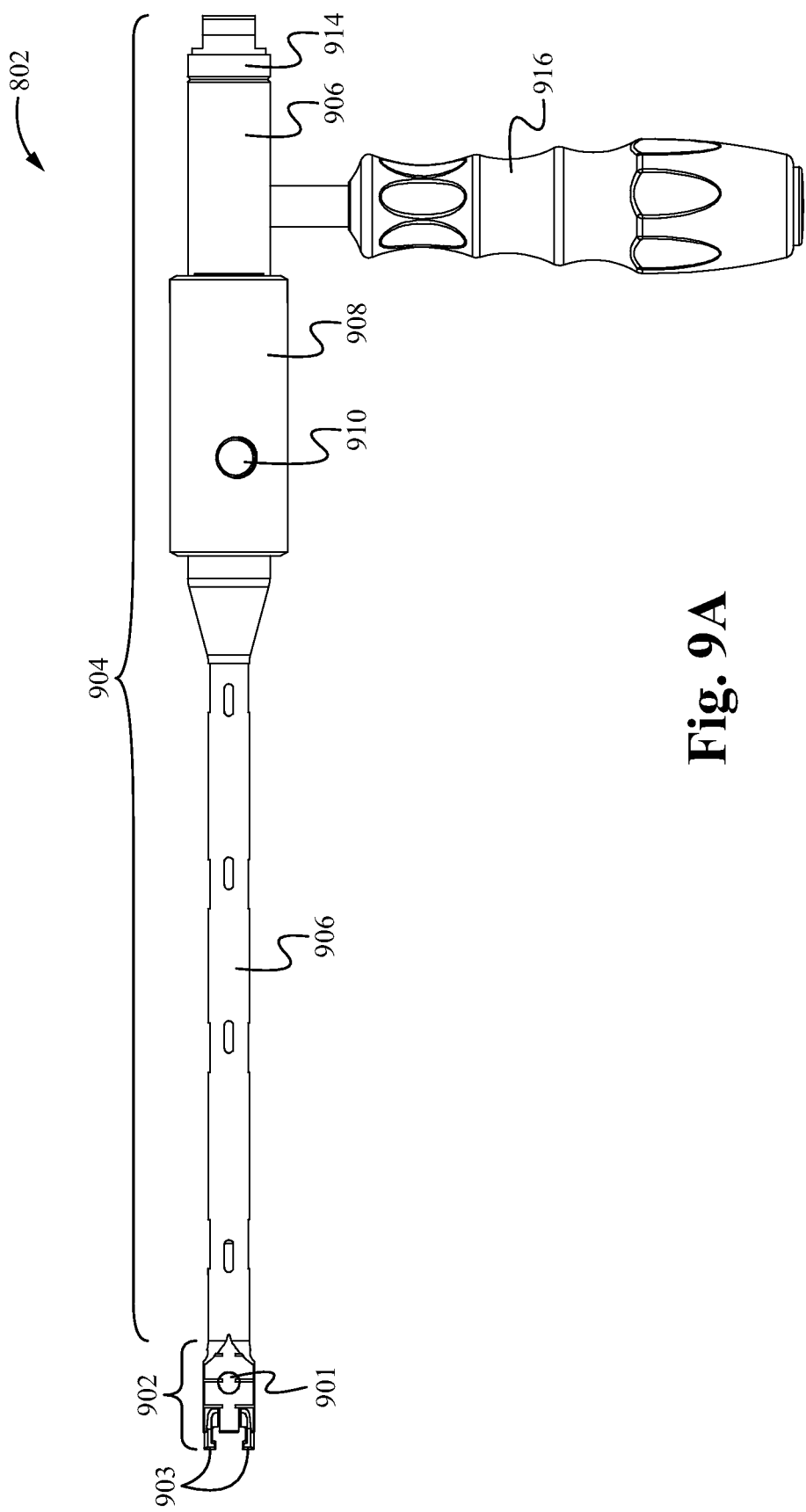
FIG. 9A illustrates a side view of the insertion instrument according to some embodiments.
Figure 9B:
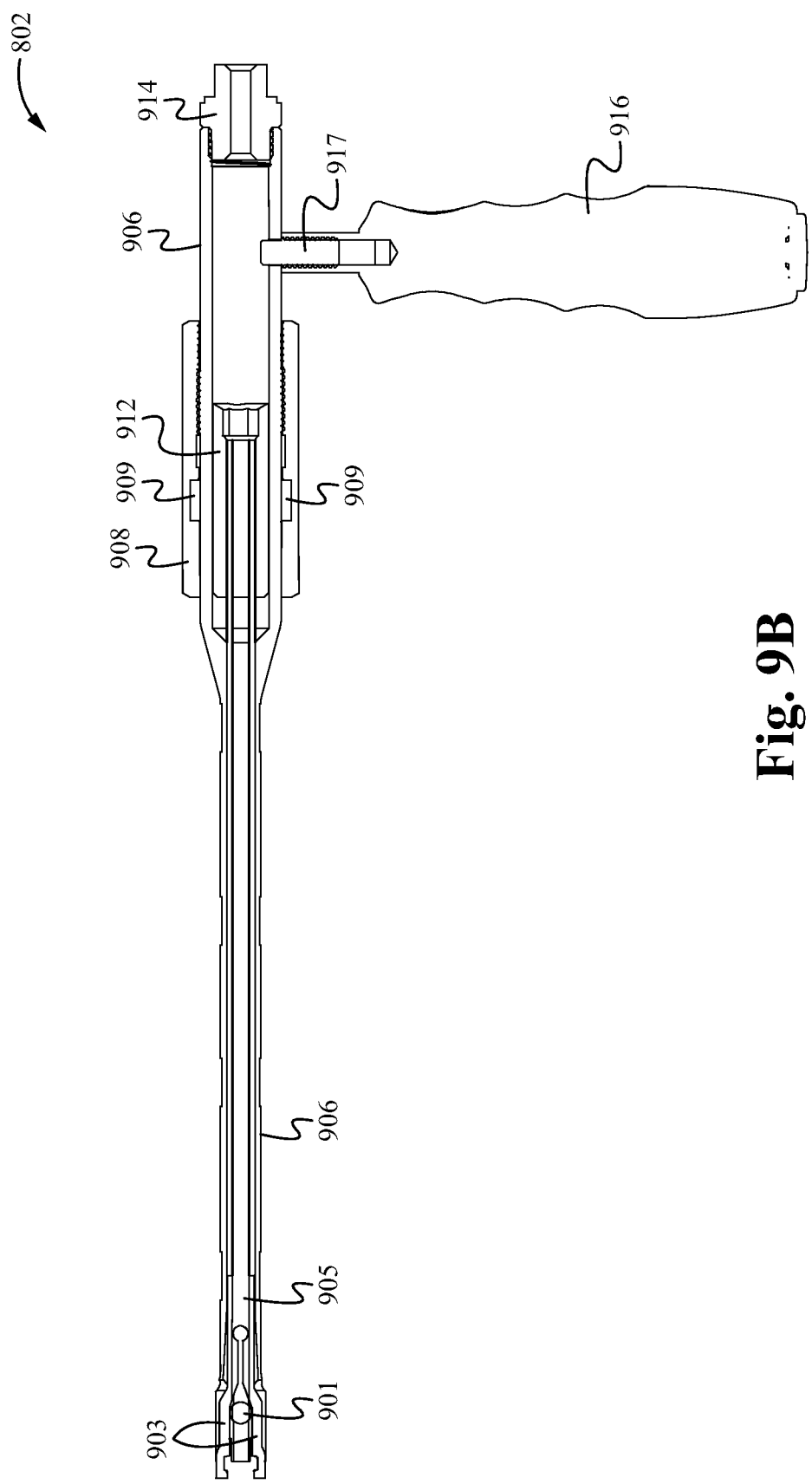
FIG. 9B illustrates a side cross-sectional view of the insertion instrument according to some embodiments.
Figure 9C:
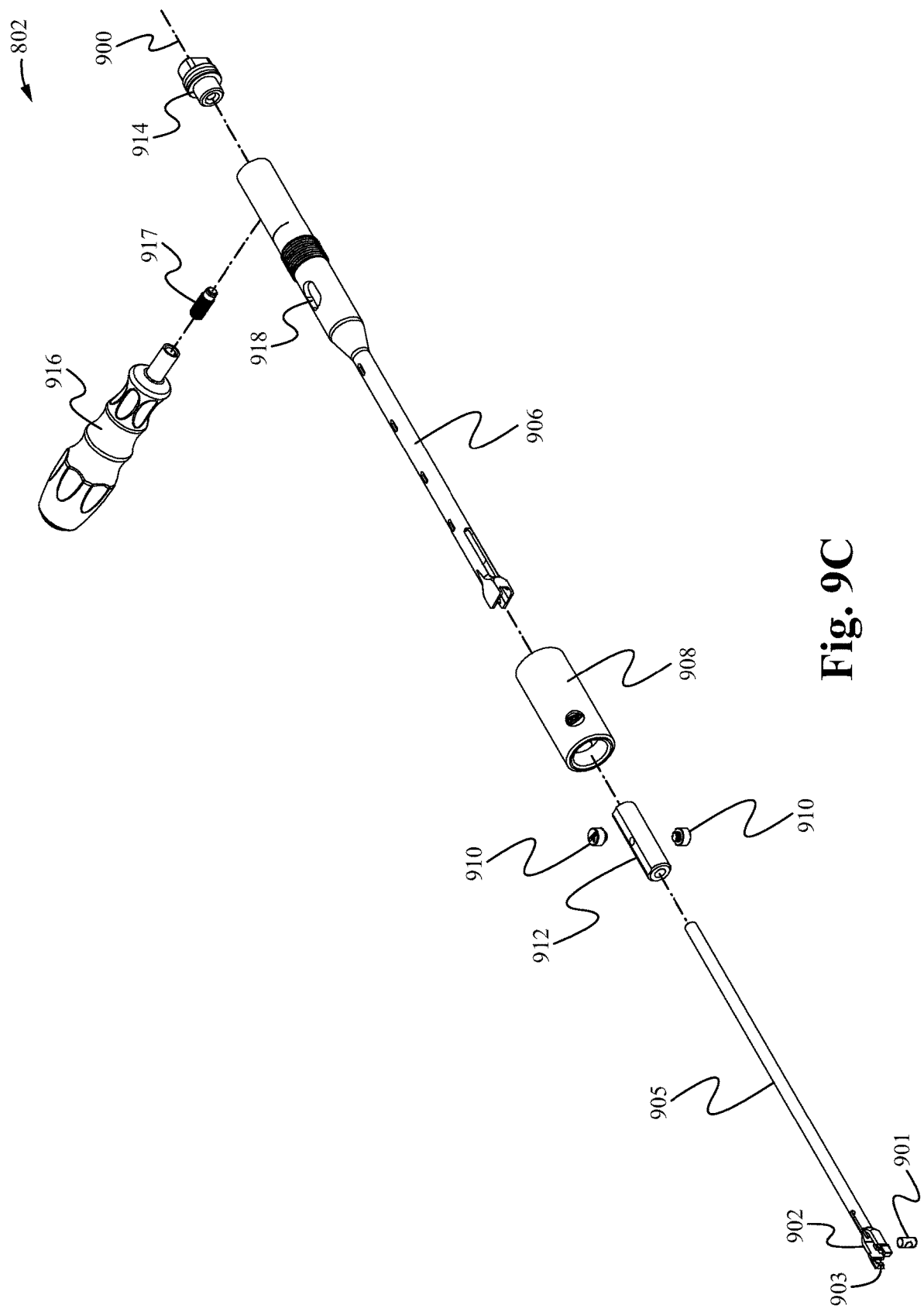
FIG. 9C illustrates a perspective exploded view of the insertion instrument according to some embodiments.
Figure 10A:
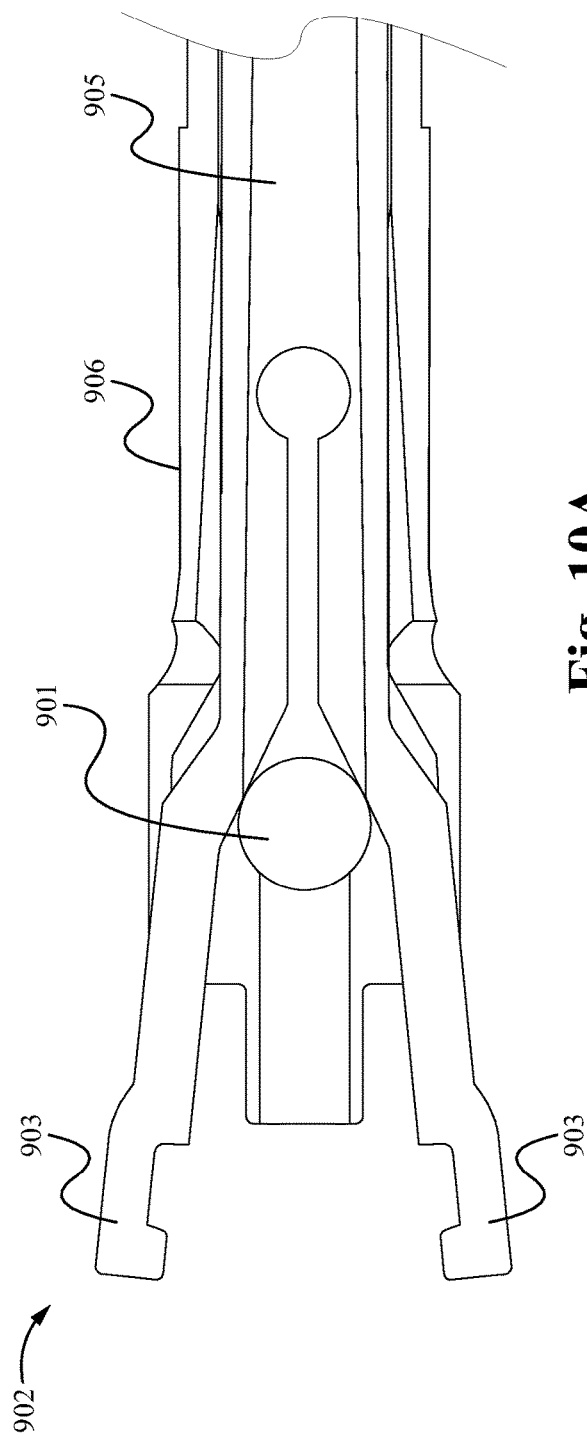
FIG. 10A illustrates an insertion instrument having fingers in a spread position according to some embodiments.
Figure 10B:
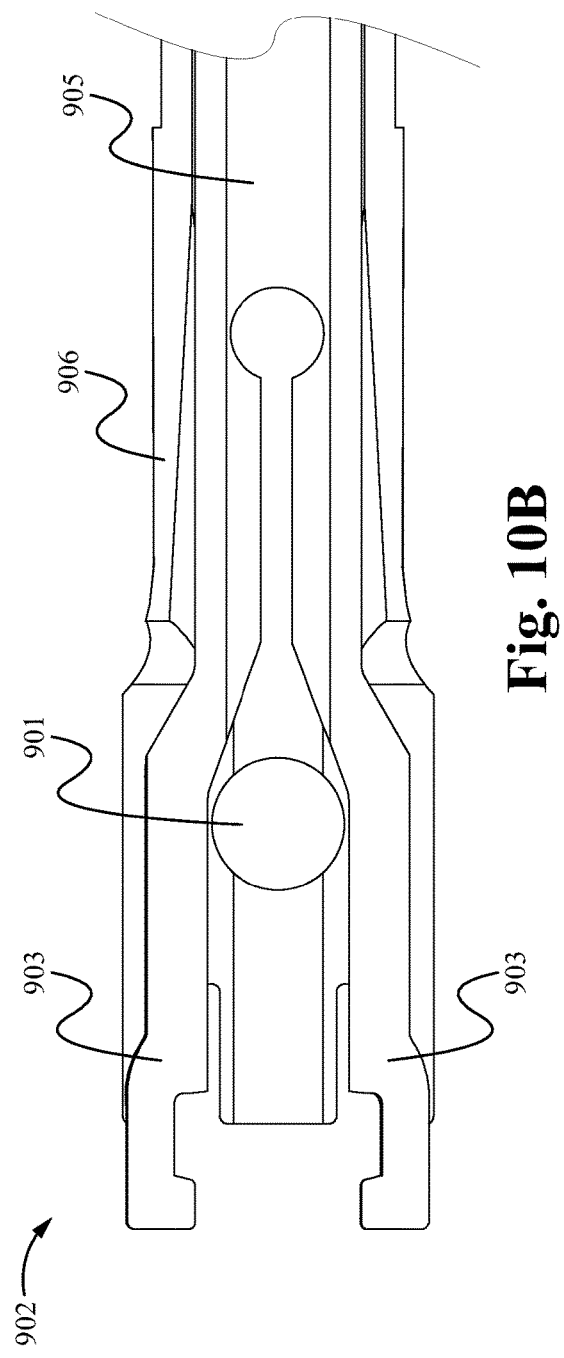
FIG. 10B illustrates an insertion instrument having fingers in a closed position according to some embodiments.

FIG. 9A illustrates a side view of the insertion instrument 802 according to some embodiments. FIG. 9B illustrates a side cross-sectional view of the insertion instrument 802 according to some embodiments. FIG. 9C illustrates a perspective exploded view of the insertion instrument 802 according to some embodiments. As shown in FIG. 9A, the insertion instrument 802 comprises a body portion 904 including a housing tube 906, a clamping sleeve 908, one or more channel knobs 910, a handle 916 and an end cap 914, and a head portion 902 including a plurality of clamping fingers 903 and a spreading rod 901 operably coupled within the head portion 902 of the housing tube 906. In some embodiments, the head portion 902 is sized such that the cross-section of the head 902 is smaller than the cross section of the bone fusion device 100. As shown in FIG. 9B, the spreading rod 901 is positioned within the head portion 902 of the housing tube 906 between the clamping fingers 903, which extend from a finger tube 905 that is positioned within a hollow cavity of the body portion 904 of the housing tube 906. Specifically, the spreading rod 901 is fixed in position relative to the housing tube 906. As a result, when the finger tube 905 is slide further out of the head 902 of the tube 906, the fingers 903 are forced further apart by the rod 901 until they are in a spread position as shown in FIG. 10A, and when the finger tube 905 is slide back into the head 902 of the tube 906, the fingers 903 are able to move closer together to a closed position as shown in FIG. 10B. In the spread position, the fingers 903 are separated by a distance greater than the distance between the surface of the gripping apertures 128 and/or the channels 122 having the gripping apertures 128. In the closed position, the fingers 903 are separated by a distance equal to or less than the distance between the surface of the gripping apertures 128 and/or the channels 122 having the gripping apertures 128. Thus, when in the closed position, the fingers 903 are able to enter the gripping apertures 128 and secure the coupling mechanism 806 to the bone fusion device 804, and when in the spread position, the fingers 903 are able to be removed from the gripping apertures 128 thereby releasing the coupling mechanism 806 from the device 804.

Figure 10C:
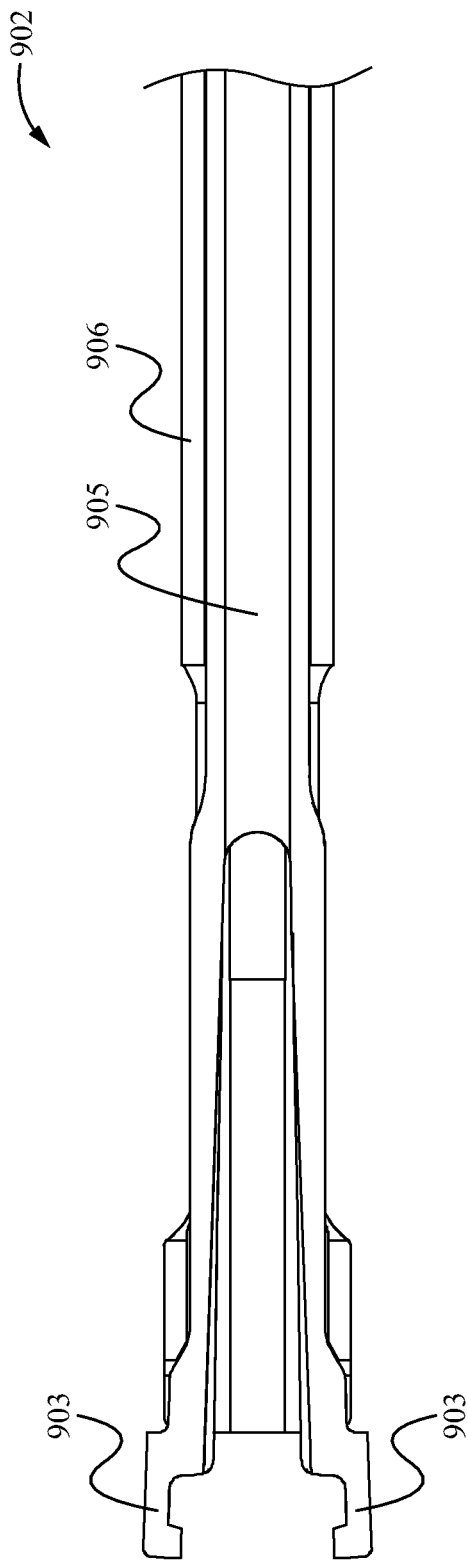
FIG. 10C illustrates an insertion instrument having fingers in a spread position according to some embodiments.
Figure 10D:
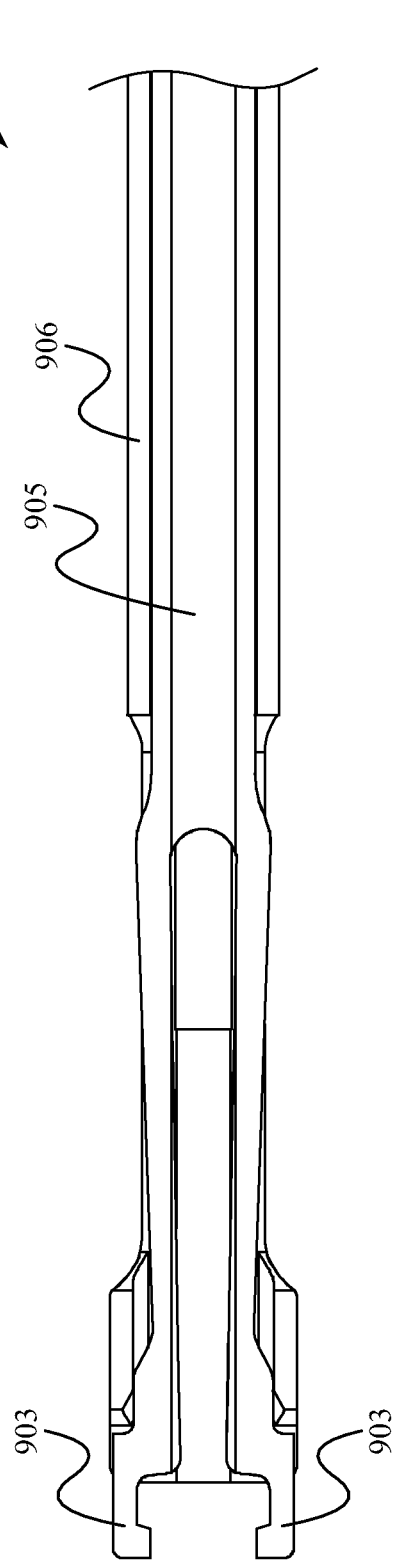
FIG. 10D illustrates an insertion instrument having fingers in a closed position according to some embodiments.

In some embodiments, the fingers 903 are biased toward the closed position such that when not forced apart by the rod 901 the fingers 903 automatically spring back to the closed position. Alternatively, the fingers 903 are able to not be biased and the walls of the head portion 902 of the housing tube 906 are able to push the fingers 903 back into the closed position as they are pulled back into the head 902. Alternatively, as shown in FIGS. 10C and 10D, the fingers 903 are able to be biased in the spread position such that when not forced together by the walls of the head 902 of the housing tube 906 the fingers 903 automatically spring to the spread position. In particular, in such embodiments the spreading rod 901 is able to be omitted. As also shown in FIG. 9B, the end cap 914 is threaded or screwed into the end of the housing tube 906 and the handle 916 is threaded or screwed into the side of the housing tube 906 via a threaded connection member 917 such that the handle is perpendicular or substantially perpendicular to a central axis 900 of the instrument 802 (as shown in FIG. 9C). The end cap 914 is able to be tubular with a round or circular exterior surface to facilitate the screwing and threadable coupling. However, a back end of the end cap 914 is able to have one or more cutouts such that instead of being circular, a cross section of the back end of the end cap 914 that is perpendicular to the central axis 900 will be non-circular. For example, as shown in FIGS. 9A-C, the top and bottom of the back end are cutout such that the cross-section is a partial circle minus portions above a top secant line and a bottom secant line. Alternatively, any other cutouts are able to be used that produce non-circular cross-sections. In particular, as described in detail below, the non-circular cross-section enables a measuring tool 1100 to slide onto the back end of the end cap 914, wherein the non-circular cross-section prevents the measuring tool 1100 from being able to rotate about the back end when coupled.

Further, an end tube 912 and the channel knobs 910 are able to be coupled to the end of the finger tube 905. In some embodiments, the end tube 912 and/or channel knobs 910 are able to be integrated into the finger tube 904. Alternatively, the end tube 912 is able to be omitted. The control sleeve 908 is threaded or screwed onto the outside of the housing tube 906 such that, when rotated in a first direction about the threading, the control sleeve 908 moves toward the head 902 and, when rotated in the opposite direction about the threading, the control sleeve 908 moves toward the opposite end of the instrument 802 near the end cap 914. Further, the inner surface of the sleeve 908 has an annular channel 909 configured for receiving the ends of the channel knobs 910 through one or more corresponding sliding apertures 918 within the housing tube 906. Specifically, the channel knobs 910 are able to extend from the end tube 912 and/or finger tube 905 through the sliding apertures 918 and at least partially into the channel 909 of the sleeve 908. As a result, when the sleeve 908 moves toward or away from the head 902 (via rotation about the threading), the position of the knobs 910 in the channel 909 causes the knobs 910 to be pushed/pulled by the sleeve 908 and thereby correspondingly move the finger tube 905 toward or away from the head 902 which, as described above, causes the fingers 903 to move between the spread and closed positions. The edges of the sliding apertures 918 are able to limit the extent to which the knobs 910 are able to slide and thereby prevent the fingers 903 from being spread too far apart or pulled too far into the tube 906. Accordingly, a user is able to controllably move the fingers 903 between the spread and closed positions by selectively rotating the sleeve 908 between a closed and open (or spread) position. Although as shown in FIGS. 9A-C, the instrument 802 includes two knobs 910 positioned through two separate apertures 918, more or less knobs 910 and/or apertures 918 are able to be used.

In some embodiments, the instrument 802 further comprises a central hollow channel that extends through the length of the instrument 802 along an axis 900 from the end of the head 902 to the end of the body 904 at the end cap 914 as shown in FIG. 9C. Specifically, each of the components of the instrument 802 that cross the axis 900 (e.g. finger tube 905, end cap 914, spreading rod 901) are able to have an aperture, channel or through-hole that aligns with the axis 900 such that together each of the components form the central hollow channel of the instrument 802. As a result, as discussed in detail below, a docking rod 1506 and/or a bone fusion device engaging tool 1200 (e.g. a screw driver rod) is able to be selectively removed or positioned through the central hollow channel in order to access the positioning aperture 134 of a bone fusion device 100 coupled to the instrument 802 by the fingers 903.

Measurement Apparatus

FIGS. 11A-11D illustrate perspective, top, front and back views, respectively, of a measuring tool 1100 according to some embodiments. Specifically, as shown in FIGS. 11A-11D, the measuring tool 1100 comprises an indicator body 1102 and a coupling cap 1104. The indicator body 1102 comprises a screw 1110, a viewing aperture 1113, an indicator ring 114, a height line 1115, height markings 116 and a support bridge 1118. The coupling cap 1104 comprises a coupling aperture 1106, aperture bracers 1107, a gear wheel 1108 having perimeter teeth 1109, a screw gear 1111 and a compatibility marker 1112. Alternatively, one or more of the components of the cap 1104 and/or the body 1102 are able to be omitted.

The indicator ring 1114 is threaded and screwed onto the screw 1110 and both are positioned within the body 1102. In some embodiments, the ring 1114 protrudes at least partially into the viewing aperture 1113. The height markings 1116 are positioned along the perimeter of at least a portion of the viewing aperture 1113, which extends vertically along a side of the body 1102. As a result, the ring 1114 is exposed or visible within the body 1102 when it is positioned on the screw 1110 adjacent to one or more of the height markings 1116. The screw 1110 is pivotably or rotatably coupled within the body 1102 and the ring 1114 is slidably coupled within the body 1102 such that the screw 1110 is able to rotate about its axis within the body 1102 causing the ring 1114 to slide up or down the screw 1110 along the viewing aperture 1113 depending on the direction of rotation. In some embodiments, the ring 1114 is prevented from rotating with the screw 1110 due to its protrusion into the viewing aperture 1113. As a result, the rotation of the screw 1110 causes the ring 1114 and its height line 1115 to move with respect to height markings 1116 (along the axis of the screw 1110) and thus sometimes align with the height markings 1116.

On the surface of the cap 1104, the compatibility marker 1112 indicates one or more bone fusion devices 804 with which the measuring instrument 802 is compatible. Specifically, in this context compatible means that the markings 1116 and/or the screw 1110/ring 1114 threading granularity are proportional to the rate of extension of the tabs of the indicated compatible bone fusion devices 804 indicated by the marker 1112. In other words, the instrument 1100 is compatible with a bone fusion device 802 if the amount of the extension of the tabs of the device 804 is accurately indicated by the alignment of the markings 1116 and the height line 1115 of the ring 1114 when the instrument 1100 is used in concert with the extension/retraction of the tabs as described in detail below.

Within the cap 1104, the gear wheel 1108 is rotatably coupled about the coupling aperture 1106 and has both inner gear teeth 1109a and outer gear teeth 1109b, wherein at least the inner gear teeth 1109a are exposed/accessible from the exterior of the cap 1104 about the aperture 1106. Similarly, the screw gear 1111 is fixedly coupled to the screw 1110, but rotatably coupled within the cap 1104 about the axis of the screw 1111 such that the screw 1110 and the screw gear 1111 together are able to rotate within the cap 1102 and body 1104 about the axis of the screw 1110. The outer gear teeth 1109b of the gear wheel 1108 are engaged with the gear teeth of the screw gear 1111. Consequently, the rotation of the screw 1110 is able to be caused by rotating the gear wheel 1108 (e.g. via the inner gear teeth 1109a) which in turn rotates the screw gear 1111 coupled to the screw 1110. Therefore, movement of the ring 1114 with respect to the markings 1116, the screw 1110 and/or the aperture 1113 is proportional to and based on the rotation of gear wheel 1108 and/or the corresponding rotation of the screw/screw gear 1110, 1111.

Figure 12:
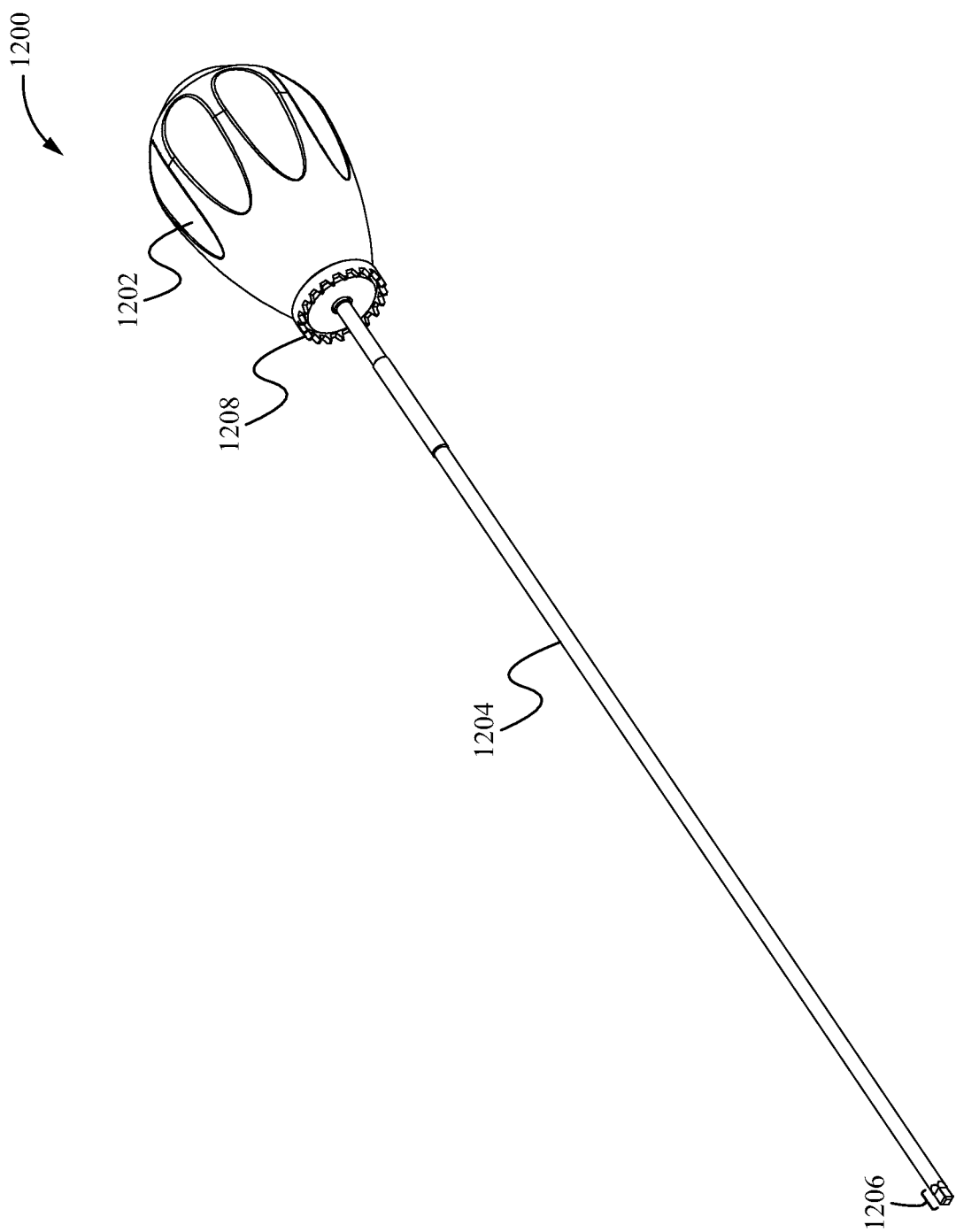
FIG. 12 illustrates a bone fusion device engaging tool according to some embodiments.
Figure 13:
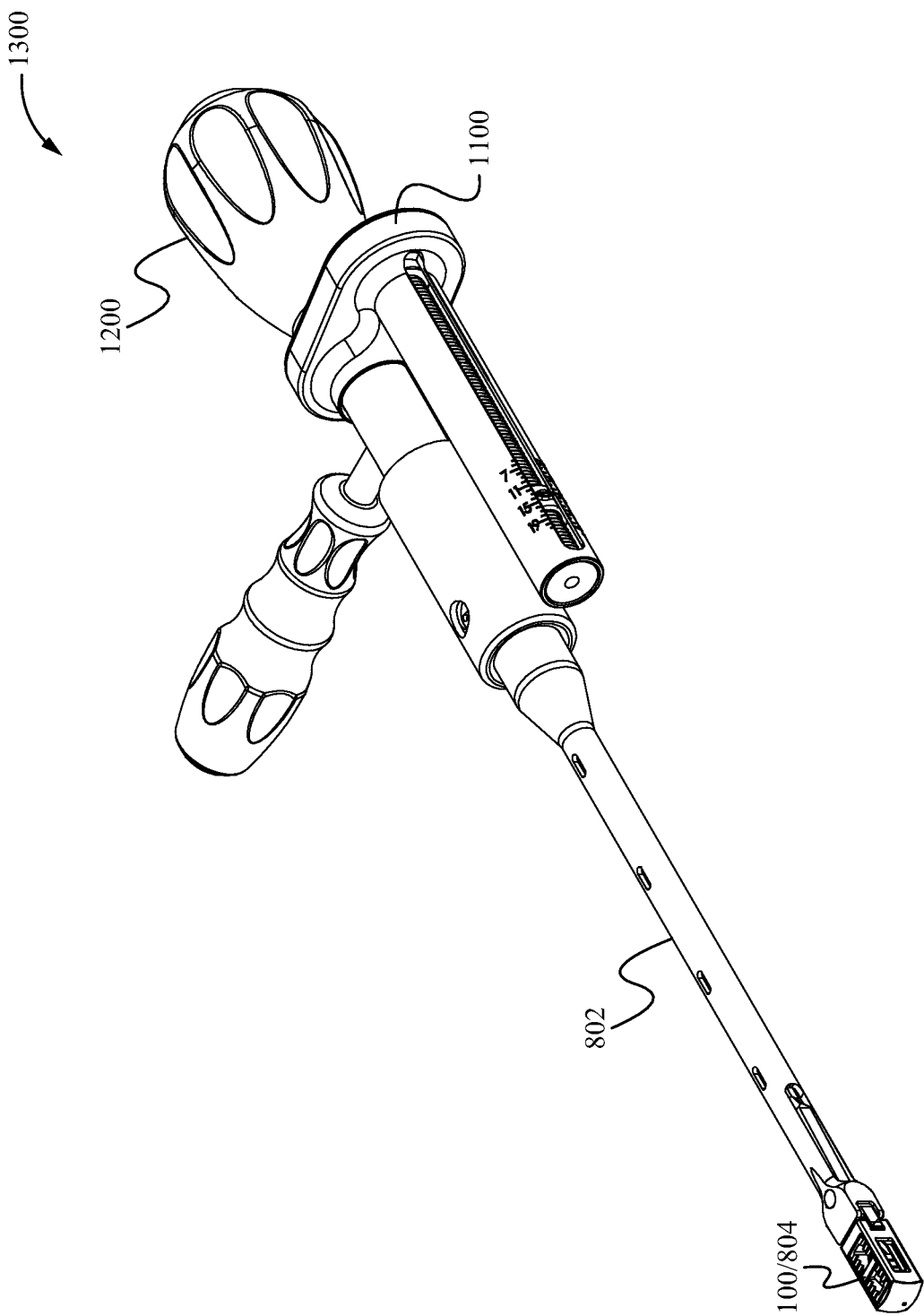
FIG. 13 illustrates a bone fusion device insertion and measuring system according to some embodiments.

As shown in FIG. 13, the coupling aperture 1106 is defined by the aperture bracers 1107 such that the back end of the end cap 914 of the insertion instrument 802 is able to fit in between the bracers 1107 within the aperture 1106. In particular, the aperture 1106 as defined by the bracers 1107 is able to have a non-circular cross-section that matches the cross-section of the back end of the end cap 914 in order to enable the end cap 914 to slide into the aperture 1106 but not rotate within the aperture 1106. As a result, the coupling aperture 1106 enables the measuring tool 1100 to detachably couple to the insertion instrument 802. Further, because of the position of the end cap 914, when coupled to the insertion instrument 802 the aperture 1106 and/or the gear wheel 1108 are centered about the central axis 900 and/or the central hollow channel of the insertion instrument 802. In particular, as described in detail below, this enables the engaging tool 1200 (FIG. 12) to align with the aperture 1106 and/or the gear wheel 1108 when slid through the aperture 1106 into the central hollow channel of the insertion instrument 802 for engaging the bone fusion device 804. Additionally, the support bridge 1118 is sized and contoured to match and contact the outer surface of the insertion instrument 802 when the measuring tool 1100 and the insertion instrument 802 are coupled together in order to prevent the body 1102 from bending the cap 1104 toward the instrument 802. Alternatively, the support bridge 1118 is able to be omitted.

Figure 11F:
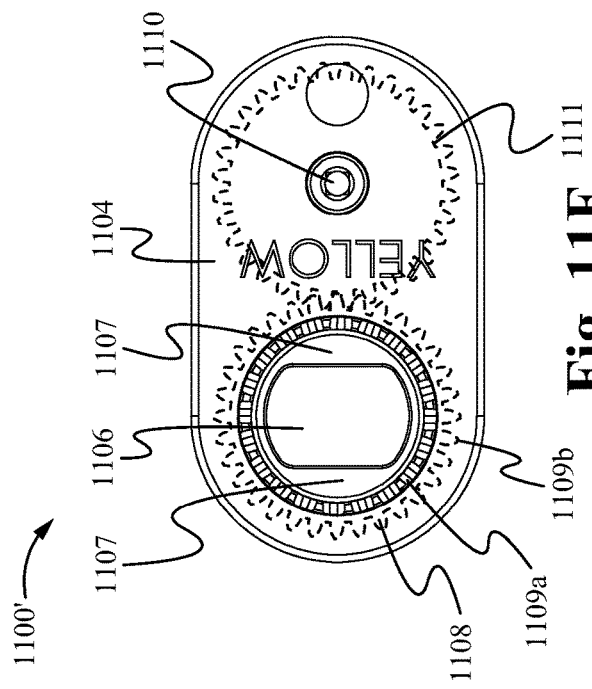
FIGS. 11E-11H illustrate perspective, top, front and back views, respectively, of a measuring tool according to some embodiments.
Figure 11H:
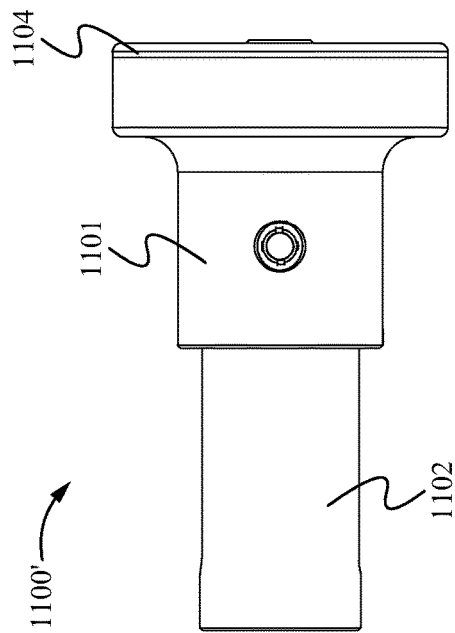
Figure 11E:
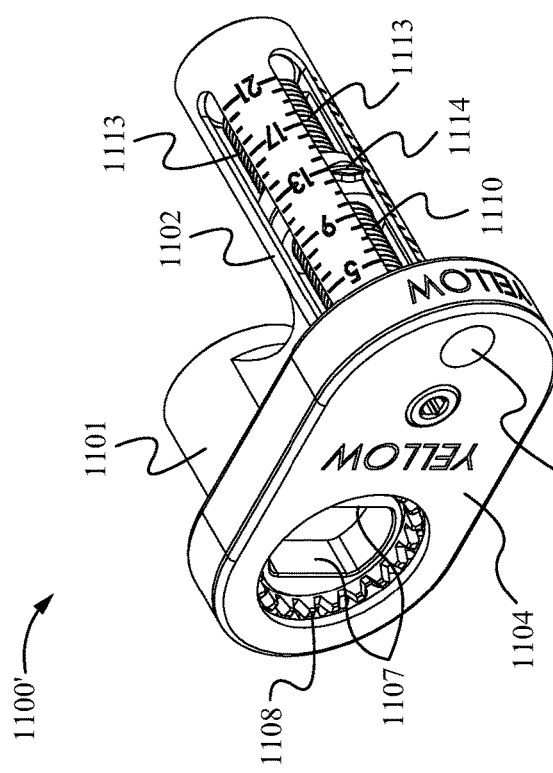
Figure 11G:
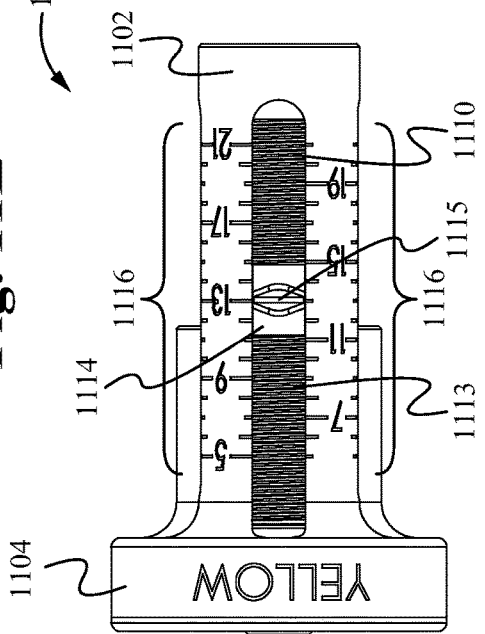

FIGS. 11E-11H illustrate perspective, top, front and back views, respectively, of an alternate embodiment of the measuring tool 1100' according to some embodiments. The measuring tool 1100' shown in FIGS. 11E-11H is able to be the substantially same as the measuring tool 1100 shown in FIGS. 11A-11D except for the differences described herein. Specifically, the measuring tool 1100' comprises an indicator body 1102 having a protruding neck 1101 that provides further support for the cap 914 when inserted into the coupling aperture 1116, wherein the support bridge 1118 is omitted. Additionally, the body 1102 is able to include a plurality of viewing apertures 1113. In some embodiments, there are three viewing apertures 1113. One aperture 1113 on the end of the body 1102, as shown in FIG. 11F, and two on either side of the body 1102 (one is shown in FIG. 11E and the other is hidden on the opposite side). As a result, the tool 1100' is able to be read from any of the three sides.

Further, each viewing aperture 1113 is able to have a corresponding set of markings 1116 and/or two or more of the viewing apertures 1113 are able to share a set of markings 1116. For example, as shown in FIG. 11E, a set of markings 1116 is able to be positioned in between two of the apertures 1113 such that the lines of the markings are able to be read (e.g. extend to) both of the apertures 1113.

FIG. 12 illustrates a bone fusion device engaging tool 1200 according to some embodiments. As shown in FIG. 12, the tool 1200 comprises a handle 1202 coupled to an elongated member or rod 1204 having an engaging tip 1206 and an interface gear 1208 coupled to the base of the handle 1202 centered around the member 1204. The elongated member 1204 is able to be tubular and/or sized to slide and rotate within the central hollow channel of the insertion instrument 802 along the axis 900. The tip 1206 is able to be configured (e.g. contoured) to operably fit within or otherwise interface with the positioning aperture 134 of the device 804 such that when positioned within the aperture 134, rotation of the tip 1206 causes the positioning component 108 to correspondingly rotate. For example, the tip 1206 is able to have a hexagonal shape, a star-shape, a flat-head shape, a phillips head shape or other types of bit shapes as are known in the art. The teeth of the interface gear 1208 are able to be configured to operably engage with the inner teeth 1109a of the gear wheel 1108. Further, as shown in FIG. 13, when fully slid into the central hollow channel of the insertion instrument 802 after the measuring tool 1100 is positioned on the end of the end cap 914 (e.g. through the coupling aperture 1106), the teeth of the interface gear 1208 operably engage with the inner teeth 1109a of the wheel gear 1108. As a result, rotation of the engaging tool 1200 causes the wheel gear 1108 to correspondingly rotate, which as described above moves the indicator ring 1114 up and down the screw 1110. Similarly as shown in FIG. 13, the elongated member 1204 is able to have a length such that when fully slid into the central hollow channel of the insertion instrument 802, the tip 1206 extends into the positioning aperture 134 when the device 100/804 is coupled to the insertion instrument 802. Accordingly, when operably coupled, rotation of the engaging tool 1200 simultaneously extends/retracts the tabs 130 of the coupled device 100/804 and moves the indicator ring 1114 with respect to the markings 1116.

FIG. 13 illustrates a bone fusion device insertion and measuring system 1300 according to some embodiments. As shown in FIG. 13, the system 1300 has the engaging tool 1200 and the measuring tool 1100 both operably coupled with the insertion instrument 802, with the bone fusion device 100/804 also being coupled to the instrument 802. As further shown in FIG. 13 and described above, when the device 100/804 is grasped by the coupling mechanism 806 in the closed position, the tabs 130 are able to be selectively extended or retracted by rotating the engaging tool 1200 with respect to the instrument 802 and/or device 100/804 as the tip 1206 is engaged within the positioning aperture 134. At the same time, the rotation of the engaging tool 1200 is able to move the indicator ring 1114 of the measuring tool 1100 with respect to the markings 1116 via the engagement of the interface gear 1208 and the gear wheel 1108, wherein the movement of the indicator ring 1114 is proportional to the amount of extension of the tabs 130 such that its alignment with the markings 1116 indicates the current amount of extension of the tabs 130. Consequently, the engaging tool 1200, measuring tool 1100, device 100/804 and/or insertion instrument 802 provide the advantage of enabling a user to control and determine a current amount that the tabs 130 are extended by observing the alignment of the height line 1115 with the markings 1116. Additionally, the removability of the engaging tool 1200 from the insertion instrument 802 beneficially enables the insertion instrument 802 to be used in concert with other tools or rods by simply removing the engaging tool 1200 when no longer needed. Similarly, the removability of the measuring tool 1100 enables different devices 100/804 having different sizes and/or rates of tab 130 extension to be used with the same insertion instrument 802 by simply replacing current measuring tool 1100 (having a first compatibilty marker 1112 that does not correspond to the desired device 100/804) with a different measuring tool 1100 having a compatibility marker 1112 that corresponds to the desired device 100/804.

Figure 14:
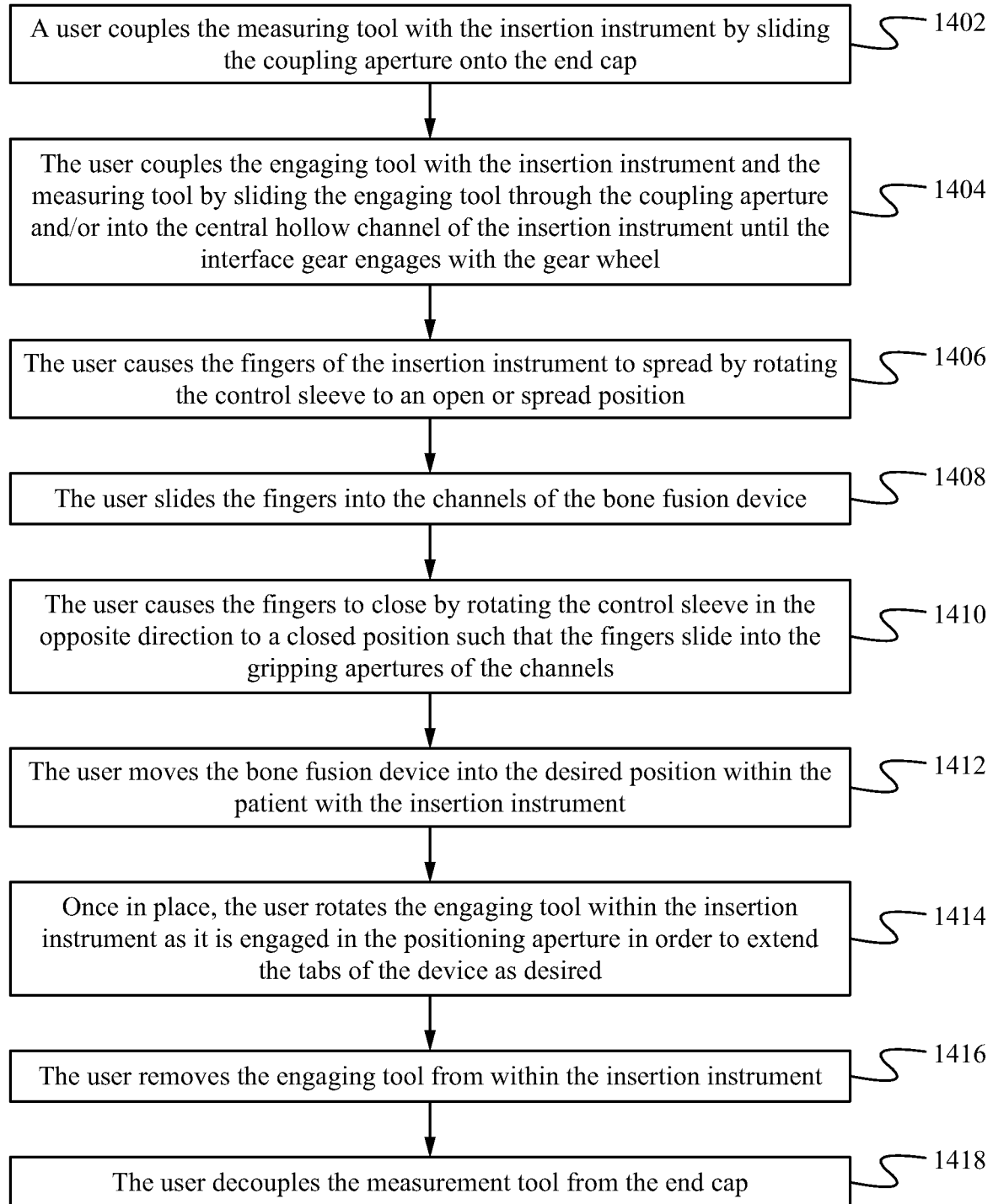
FIG. 14 illustrates a flow chart of a method of operation of the bone fusion system according to some embodiments.

A method of operation of the bone fusion system 1300 according to some embodiments will now be discussed in conjunction with the flow chart shown in FIG. 14. A user couples the measuring tool 1100 with the insertion instrument 802 by sliding the coupling aperture 1106 onto the end cap 914 at the step 1402. In some embodiments, step 1402 comprises selecting the measuring tool 1100 from a plurality of measuring tools 1100 each having a compatibility marker 1112 based on which of the tools 1100 has compatibility markers 1112 that corresponds to the desired bone fusion device 100/804. A user couples the engaging tool 1200 with the insertion instrument 802 and the measuring tool 1100 by sliding the engaging tool 1200 through the coupling aperture 1106 and/or into the central hollow channel of the insertion instrument 802 until the interface gear 1208 engages with the gear wheel 1108 at the step 1404. Alternatively, step 1402 is able to occur after the device 100/804 has been coupled to the insertion instrument 802 as described in step 1408.

A user causes the fingers 903 of the insertion instrument 802 to spread by rotating the control sleeve 908 to an open or spread position at the step 1406. The user slides the fingers 903 into the channels 122 of the bone fusion device 100/804 at the step 1408. The user causes the fingers 903 to close by rotating the control sleeve 908 in the opposite direction to a closed position such that the fingers 903 (or the tips of the fingers) slide into the gripping apertures 128 of the channels 122 thereby detachably coupling the insertion instrument 802 to the bone fusion device 100/804 at the step 1410. The user moves the bone fusion device 100/804 into the desired position within the patient with the insertion instrument 802 at the step 1412. In some embodiments, the inner cavity of the bone fusion device 100/804 is packed with a bone graft material prior to being positioned within the patient. In some embodiments, the desired position comprises replacing a spinal disc with the bone fusion device 804 in between two vertebrae. Alternatively, the desired position is able to comprise replacing a degenerated vertebrae with the bone fusion device 100/804 in between the two adjacent vertebrae and/or spinal discs. Alternatively, the insertion instrument 802 is able to be used to position other types of spinal devices such as a dynamic device, a total/partial artificial disc, a nucleus pulposus or other medical devices as are well known in the art. In some embodiments, the bone fusion device 100/804 is inserted anteriorly. Alternatively, the bone fusion device 100/804 is able to be inserted posteriorly, laterally or transforaminaly.

Once in place, the user rotates the engaging tool 1200 within the insertion instrument 802 as it is engaged in the positioning aperture 134 in order to extend the tabs 130 of the device 100/804 as desired at the step 1414. The user observes the alignment of the height line 1115 of the indicator ring 1114 with the height markings 1116 and stops rotating the engaging tool 1200 when the height line 1115 is aligned with the height marking 1116 indicating the desired height at the step 1416. The user removes the engaging tool 1200 from within the insertion instrument 802 at the step 1416. The user decouples the measurement tool 1100 from the end cap 914 at the step 1418. Alternatively, the measurement tool 1100 is able to remain on the end cap 914. As a result, the method of operating the bone fusion system 1300 enables the surgeon to securely position the bone fusion device 804 and extend the tabs 130 as needed with minimal possibility of the drive mechanism slipping out of the positioning aperture 134. Specifically, by coupling the fingers 903 within the gripping apertures 128 and the channels 122, the insertion instrument 802 is prevented from being pulled, pushed or twisted away from the bone fusion device 804. Thus, the procedure is made both safer and more efficient. In some embodiments, the measurement tool 1100 is able to be omitted and the engaging tool 1200 is able to be used with the insertion instrument 802 without also coupling with the measurement tool 1100.

Autograft Delivery Apparatus

Figure 15:
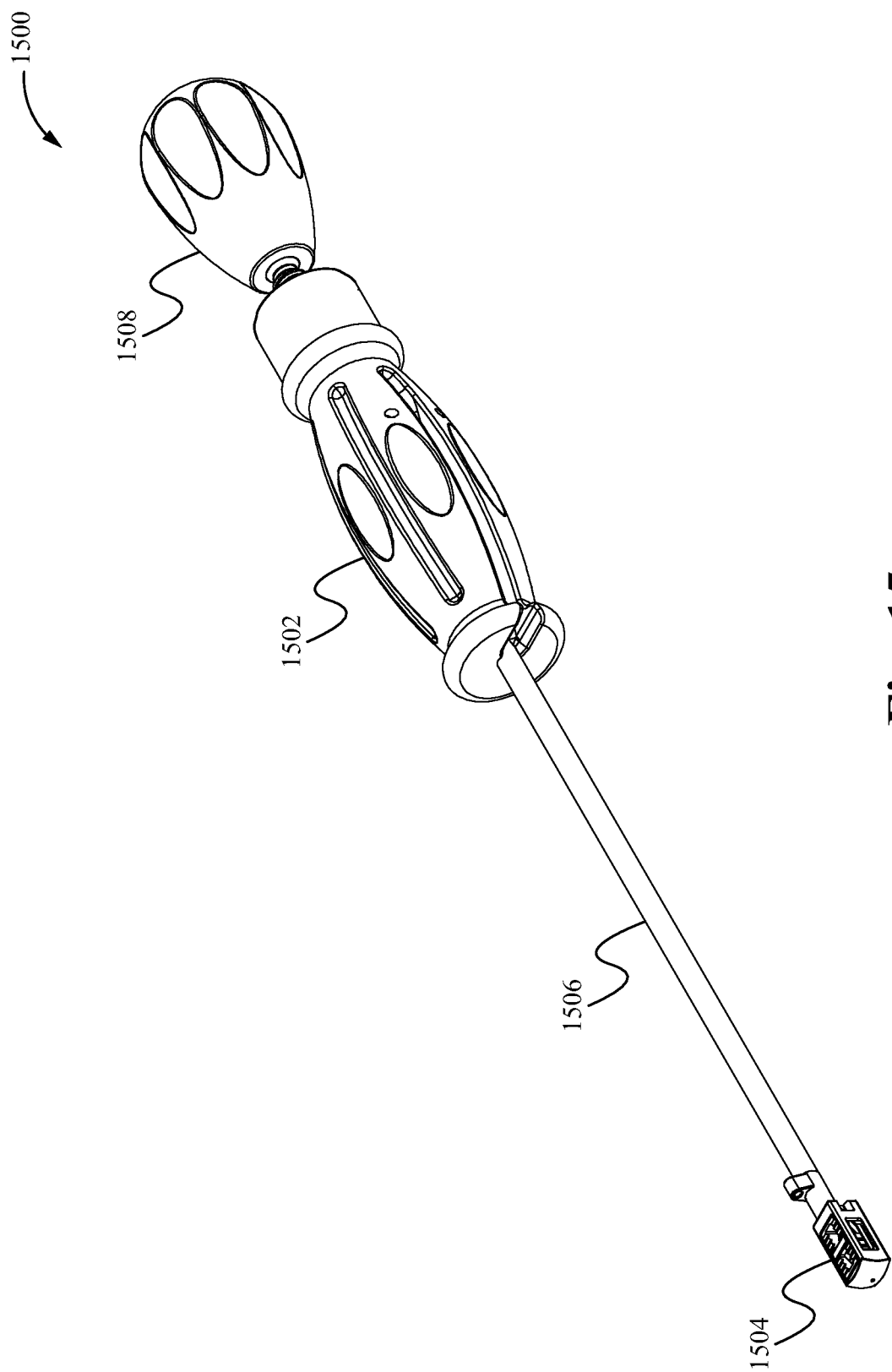
FIG. 15 illustrates a bone fusion device system according to some embodiments.
Figure 16A:
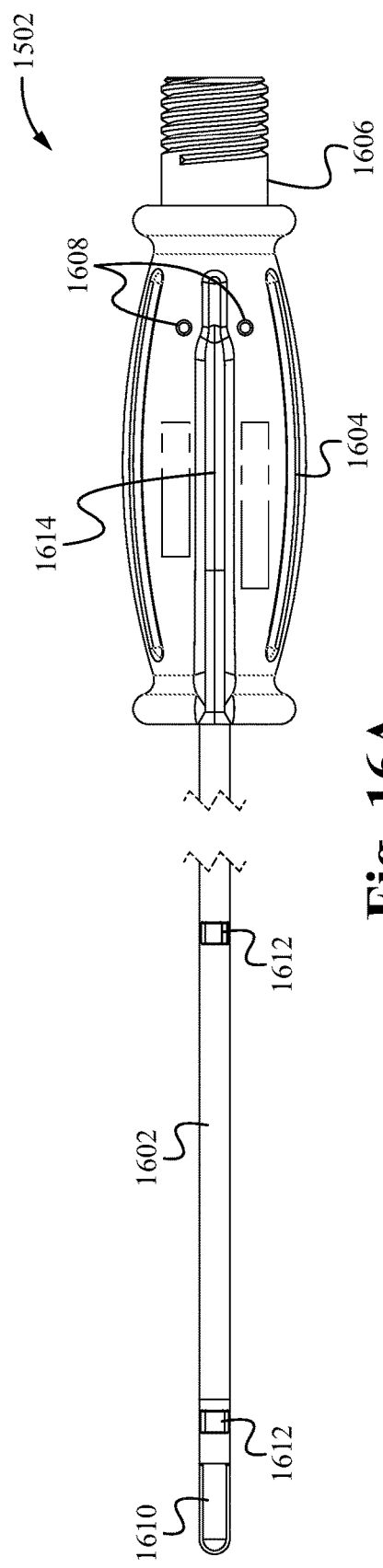
FIGS. 16A-D illustrate a top, side cross-sectional, perspective and front view, respectively, of the delivery member according to some embodiments.
Figure 16B:
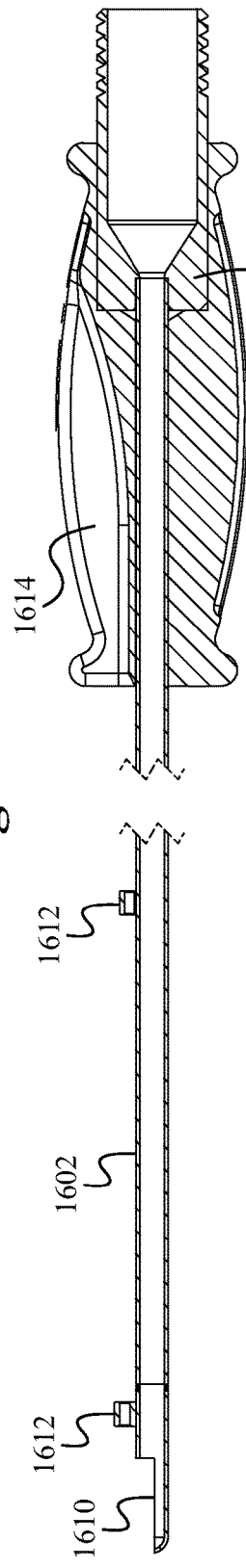
Figure 16C:
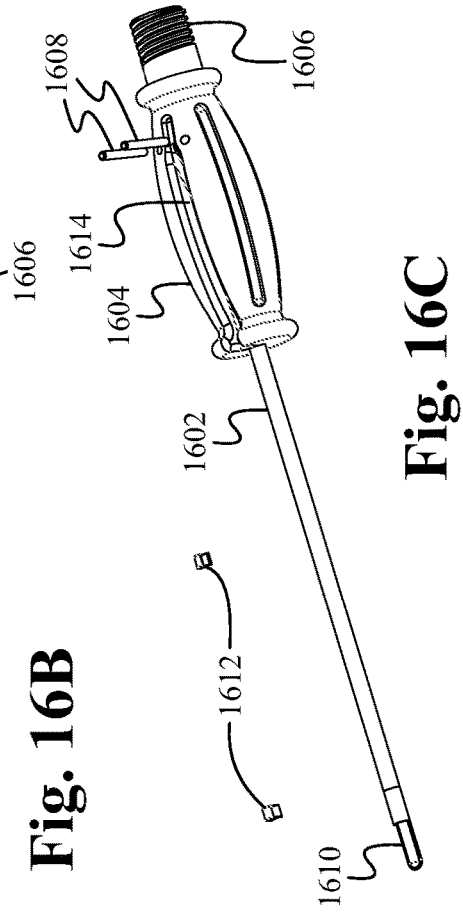
Figure 16D:
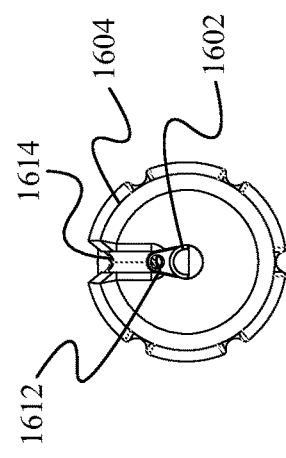

FIG. 15 illustrates a bone fusion device system 1500 according to some embodiments. As shown in FIG. 15, the bone fusion system 1500 comprises a bone fusion device 1504 and bone fusion delivery apparatus including a delivery member 1502, a docking rod 1506 and one or more plungers 1508. As shown in FIG. 15, the docking rod 1502 is able to detachably couple with the bone fusion device 1504 and thereby facilitate the coupling or interfacing of the delivery member 1502 and the bone fusion device 1504 for delivery of the autograft or other material to the inside of the device 1504 via the delivery member 1502. Specifically, the delivery member 1502 is able to slide onto and/or otherwise couple with the docking rod 1506, wherein the member 1502 and rod 1506 are configured such that, when the docking rod 1506 is coupled with the device 1504, coupling of the docking rod 1506 and the delivery member 1502 results in an coupling or interface alignment of the delivery member 1502 and the device 1504 (e.g. a channel 120 on the side of the device). The plungers 1508 are then able to detachably coupled to and/or used with the delivery member 1502 to force desired material through the delivery member 1502 into the bone fusion device 1504. The system 1500 is able to be combined with one or more of the components of the system 800 described above in order to create an insertion, measurement and/or delivery system. The bone fusion device 1504 is able to be substantially similar to the bone fusion devices 100, 804 described above. Alternatively, the bone fusion device 1504 is able to be other embodiments of bone fusion devices described herein or other types of bone fusion devices as are well known in the art. In some embodiments, the other types of bone fusion devices are able to be formed by one or more of polymers, bone, synthetic bone, metal or other biocompatible materials as are well known in the art.

FIGS. 16A-D illustrate a top, side cross-sectional, perspective and front view, respectively, of the delivery member 1502 according to some embodiments. As shown in FIGS. 16A-D, the delivery member 1502 comprises a delivery shaft 1602, a handle 1604 and a funnel 1606. The funnel 1606 is able to be at least partially coupled within a back end of the handle 1604 via one or more locking pins 1608. Alternatively, funnel 1606 is able to be integrated with the handle 1604 to form a single component or the funnel 1606 is able to be coupled with the handle 1604 via other coupling mechanisms as are well known in the art that replace or supplement the pins 1608. The a portion of the delivery shaft 1602 is able to be coupled within or through a front end of the handle 1604 such that a tip of the funnel 1606 aligns with, couples to and/or abuts an entrance aperture of the delivery shaft 1602. The remainder of the delivery shaft 1602 extends out from the front end of the handle 1604 and ends at a exit aperture 1610. The back end of the funnel 1606 is able to have a threaded outer or inner surface and/or have a tubular or circular shape such that one or more of the plungers 1508 are able to threadably couple with the funnel 1606 via the threading.

As shown in FIGS. 16A-D, the exit aperture 1610 is able to be defined by an L-shaped cutout of the tip of the delivery shaft 1602. In particular, this L-shape enables exit aperture 1610 to fit against or contour to a left or right front corner of the bone fusion device 1504 wherein the corner of the L-cutout meets the left or right front corner of the device 1504 and the scoop-like portion of the exit aperture 1610 extends along the corresponding left or right side of the bone fusion device 1504 (in order to align with one or more side channels 120). Alternatively, the exit aperture 1610 is able to comprise any other shapes that enable material to exit the tip of the shaft 1602. Indeed, in some embodiments the system 1500 is able to comprise two delivery members 1502, wherein the first member 1502 has an L-shaped exit aperture 1610 and the second member 1502 has a differently shaped exit aperture 1610 (e.g. an aperture created by a cross-section cut of the shaft 1602 orthogonal to the axis of the shaft 1602).

The delivery shaft 1602 is able to further comprise one or more coupling hoops 1612 that extend from the outer surface of the delivery shaft 1602. Specifically, each of the coupling hoops 1612 are able to be aligned such that their respective through-holes are aligned along a single axis. As a result, the coupling hoops 1612 enable the shaft 1602 to couple with the docking rod 1506 by sliding the docking rod 1506 through the through holes of the coupling hoops 1612 along the axis. In some embodiments, one or more of the coupling hoops 1612 are able to be only partial hoops or C-shaped such that they do not form a full loop. In such embodiments, the hoops 1612 are able to still have greater than fifty percent of the loop as a part of the C-shape in order to hold the docking rod 1506 within the C-shape. Although as shown in FIGS. 16A-D, the shaft 1602 has two hoops 1612, more or less hoops 1612 are able to be used.

The handle 1604 is able to comprise a docking channel 1614 configured for receiving a portion of the docking rod 1506. Specifically, the docking channel 1614 is able to be aligned with the single axis of the hoops 1612 such that the handle 1604 is able to couple with the docking rod 1506 at the same time as the shaft 1602 by sliding the docking rod 1506 along the axis through the coupling loops 1612 and into the docking channel 1614. In some embodiments, the docking channel 1614 is sized such that when the docking rod 1506 is fully slid into the channel 1614 (and through the hoops 1612) the exit aperture 1610 is aligned with one of the channels 120 of the bone fusion device 1504. Alternatively, the docking channel 1614 is able to be sloped to become shallower toward the back end of the handle 1604 such that the docking rod 1506 is guided away from the delivery member 1502 as the docking rod 1506 extends beyond the back of the docking channel 1614.

Figure 17:
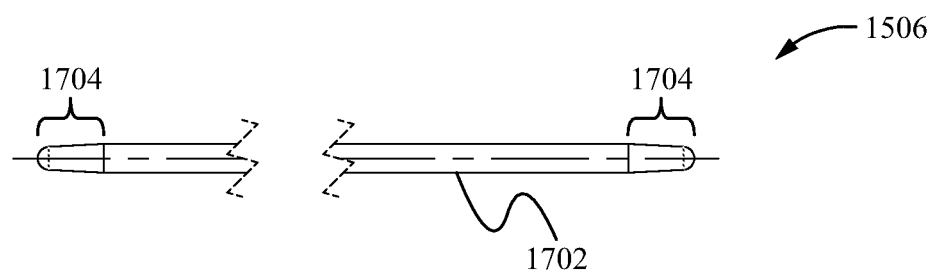
FIG. 17 illustrates the docking rod according to some embodiments.
Figure 18A:
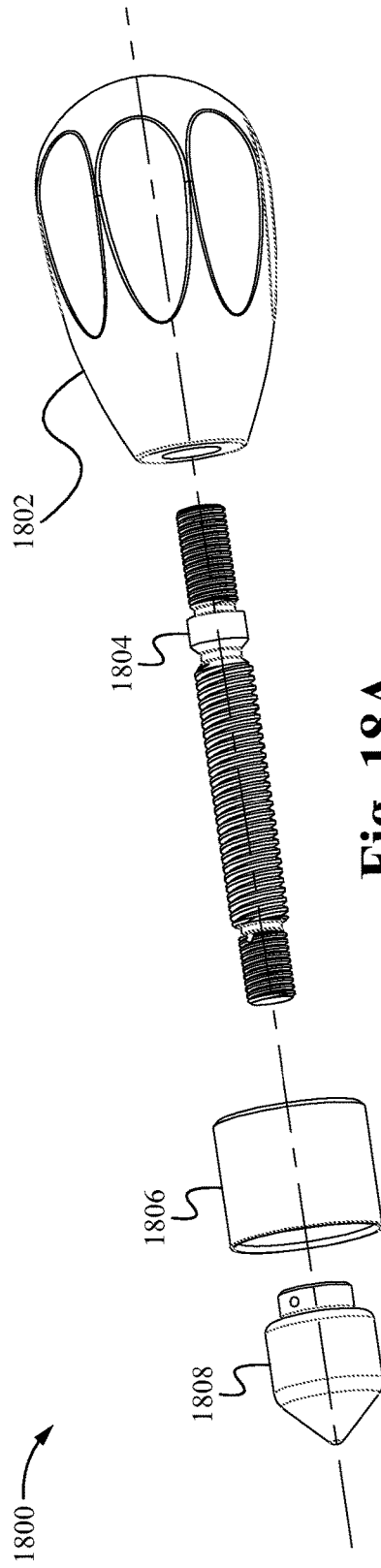
FIGS. 18A-D illustrate an exploded perspective view, a side view, a side cross-sectional view and a frontal view, respectively, of a short rigid plunger of the plungers according to some embodiments.
Figure 18B:
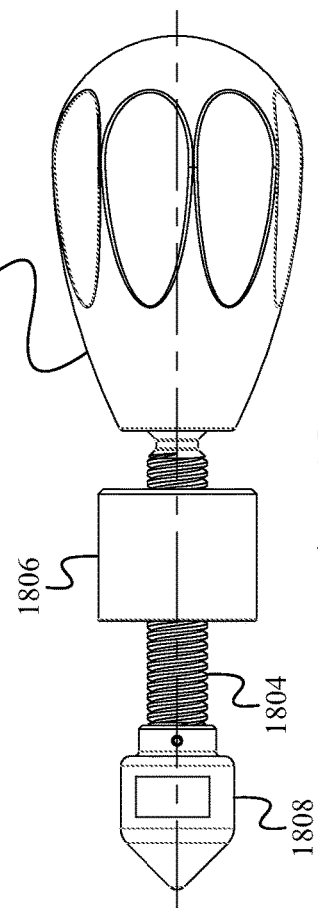
Figure 18C:
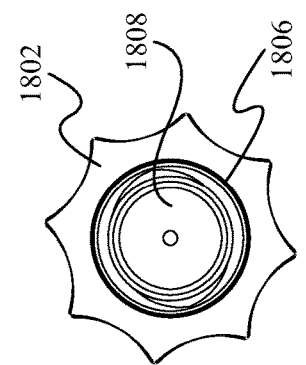
Figure 18D:
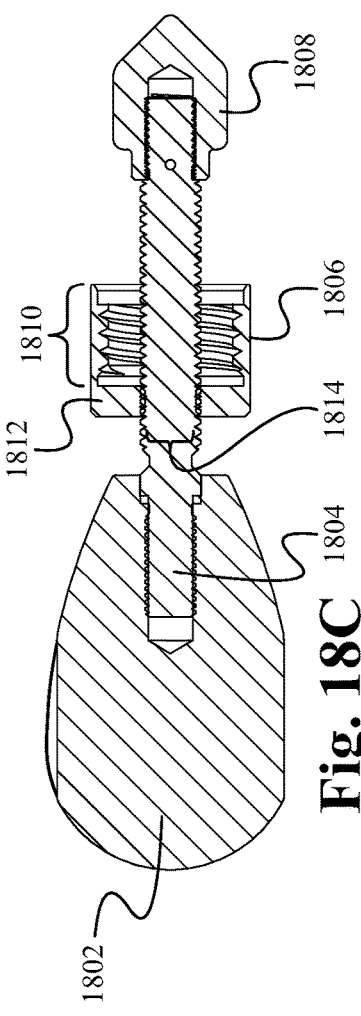

FIG. 17 illustrates the docking rod 1506 according to some embodiments. As shown in FIG. 17, the docking rod 1506 is able to have a long tubular body 1702 and a tapered tip 1704 at one or both ends of the body 1702. In particular, the tip 1704 is able to be sized and flexible such that it is able to slid into and thereby detachably couple to the positioning aperture 134 of the bone fusion device 1504 (e.g. via a friction fit). In some embodiments, the body 1702 and/or tips 1704 of the docking rod 1506 are able to be made of nitinol. Alternatively, the body 1702 and/or tips 1704 of the docking rod 1506 are able to be made of other materials and/or a combination of other materials and nitinol. In some embodiments, the docking rod 1506 is able to be flexible.

FIGS. 18A-D illustrate an exploded perspective view, a side view, a side cross-sectional view and a frontal view, respectively, of a short rigid plunger 1800 of the plungers 1508 according to some embodiments. As shown in FIGS. 18A-D, the short rigid plunger 1800 comprises a handle 1802, a screw 1804, a screw cap 1806 and a plunger head 1808. The handle 1802 and plunger head 1808 are coupled to opposite ends of the screw 1804 by screwing onto threading on either end of the screw 1804. Alternatively, other fastening methods are able to be used to couple the handle 1802 and head 1808 to the screw 1804 and the threading on the ends of the screw 1804 is able to be omitted. The head 1808 is able to have a diameter or circumference that is equal to or slightly smaller than the diameter and/or circumference of the inner surface of the funnel 1606 of the delivery member 1502. As a result, the head 1808 is able to slide into the funnel 1606 (e.g. adjacent to or contacting the inner walls of the funnel) and thereby push material down through the funnel into the shaft 1602 without the material escaping around the head 1808 between the head 1808 and the side walls of the funnel 1606. Additionally, the tapering portion of the head 1808 that points away from the screw 1804 is able to substantially match the contours of the bottom or funneling portion of the inner surface of the funnel 1606. As a result, the head 1808 is able to extend to the bottom of the funnel 1606 and push any remaining material out of the hole at the tip of the funnel 1606.

The cap 1806 has a hollow tubular body having a threaded inner surface that surrounds an inner cavity 1810. At one end of the inner cavity 1810 (facing the handle 1802), the cavity 1810 is bounded by a wall 1812 having a central screw aperture 1814 with a threaded inner aperture surface. At the other end of the cavity 1810 (facing the head 1808), there is no end wall and instead the cavity 1810 is exposed to the exterior of the body of the cap 1806. The size (e.g. diameter, radius, circumference), shape and threading of the inner aperture surface of the screw aperture 1814 is configured such that the cap 1806 is able to thread onto (and thereby couple to) a middle threaded portion of the screw 1804 in between the base of the handle 1802 and the base of the head 1806 when they are coupled to the ends of the screw 1804. As a result, head 1808 (and/or the screw 1804 and handle 1802) are able to move with respect to the cap 1806 by rotating the cap 1806 and the screw 1804 with respect to each other such that the threaded engagement between the two causes the cap 1806 to move up or down the screw 1804 depending on the direction of rotation.

The size (e.g. diameter, radius, circumference), shape and threading of the inner cavity surface of the inner cavity 1810 is configured such that the cap 1806 is able to thread onto (and thereby couple to) the threaded outer surface of the back end of the funnel 1606 of the delivery member 1502. Thus, when the short rigid plunger 1800 is coupled to the funnel 1606 (via threading the cap 1806 onto the back end of the funnel 1606), a user is able to closely control the plunging of the head 1808 into the funnel 1606 by controlling the rotation of the screw 1804 via the handle 1802 (which controls how much the screw 1804 pushes the head 1808 into or out of the funnel 1606. In some embodiments, the short rigid plunger 1800 is sized such that when the head 1808 is fully extended away from the cap 1806 (e.g. the cap 1806 has reached the base of the handle 1802 and/or the end of the central threading of the screw 1804 near the handle 1802) while the cap 1806 is coupled to the funnel 1606, the tapered end of the head 1808 abuts or contacts the bottom/funneling inner surface of the funnel 1606.

Figure 19A:
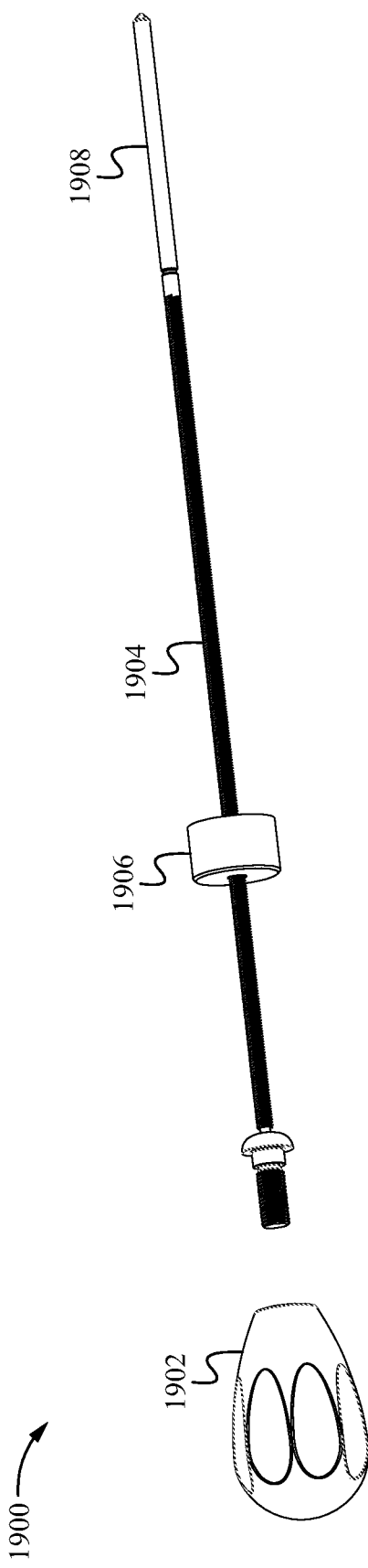
FIGS. 19A and 19B illustrate an exploded perspective view and a frontal view, respectively, of a long rigid plunger of the plungers according to some embodiments.
Figure 19B:
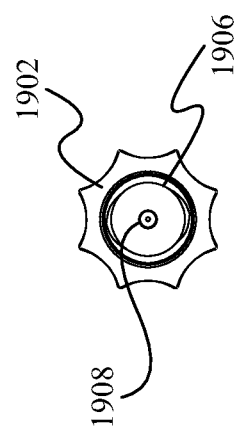

FIGS. 19A and 19B illustrate an exploded perspective view and a frontal view, respectively, of a long rigid plunger 1900 of the plungers 1508 according to some embodiments. In particular, the long rigid plunger 1900 is able to be substantially similar to the short rigid plunger 1800 except for the differences described herein. As shown in FIGS. 19A-B, similar to the short rigid plunger 1800, the long rigid plunger 1900 comprises a handle 1902, a screw 1904, a screw cap 1906 and a plunger head 1908. Unlike the short rigid plunger 1800 however, both the head 1908 and a portion of the screw 1904 coupled to the head 1908 are able to have diameters or circumferences that are equal to or slightly smaller than the diameter and/or circumference of the inner surface of the shaft 1602 of the delivery member 1502. As a result, the head 1908 and the portion of the screw 1904 are able to slide into the shaft 1602 (e.g. entering through the funnel 1606 and then sliding adjacent to or contacting the inner walls of the shaft) and thereby push material down through the shaft 1602 to and out of the exit aperture 1610 without the material escaping around the head 1908 between the head 1908 and the side walls of the shaft 1602. Thus, after the material has been pushed from the funnel 1606 in to the shaft by the short plunger 1800, the long plunger 1900 is able to push the material out the exit aperture 1610 into the bone fusion device 1504. Additionally, the tapering portion of the head 1908 that points away from the screw 1904 is able to substantially match the contours of the end portion of the inner surface of the shaft 1602/exit aperture 1610.

Like the short plunger 1800, when the long rigid plunger 1900 is coupled to the funnel 1606 (via threading the cap 1906 onto the back end of the funnel 1606), a user is able to closely control the plunging of the head 1908 into the funnel 1606 and through the shaft 1602 by controlling the rotation of the screw 1904 via the handle 1902 (which controls how much the screw 1904 pushes the head 1908 into or out of the funnel 1606/shaft 1602. In some embodiments, the long rigid plunger 1900 is sized such that when the head 1908 is fully extended away from the cap 1906 (e.g. the cap 1906 has reached the base of the handle 1902 and/or the end of the central threading of the screw 1904 near the handle 1902) while the cap 1806 is coupled to the funnel 1606, the tapered end of the head 1908 abuts or contacts the end inner surface of the shaft 1602 at the exit aperture 1610.

FIGS. 20A-C illustrate an exploded perspective view, a side view and a frontal view, respectively, of a flexible plunger 2000 of the plungers 1508 according to some embodiments. As shown in FIGS. 20A-C, the flexible plunger 2000 comprises a handle 2002, a coupling collar 2004, a crimp tube 2006 and one or more flexible rods 2008a, 2008b. The handle 2002 is threadably coupled onto a first end of the coupling collar 2004 and the crimp tube 2006 is threadably coupled into the second end of the coupling collar 2004 with the flexible rods 2008a, 2008b fixedly held within the channel through the crimp tube 2006. Alternatively, the handle 2002 and/or the crimp tube 2006 are able to be coupled to the coupling collar 2004 via different or additional fasteners as are known in the art. Alternatively, two or all three of the crimp tube 2006, the coupling collar 2004 and the handle 2002 are able to be formed as a single integrated component.

The flexible rods 2008 and/or the crimp tube 2004 are able to have diameters or circumferences that are smaller than the diameter and/or circumference of the inner surface of the shaft 1602 of the delivery member 1502. As a result, flexible rods 2008 and/or the crimp tube 2006 are able to slide into the shaft 1602 (e.g. entering through the funnel 1606) and thereby break up blockages and push material down through the shaft 1602 to and out of the exit aperture 1610. In particular, the flexible plunger 2000 is able to be sized to have a length such that when the flexible plunger 2000 is fully inserted into the delivery member 1502 (e.g. further insertion is blocked by the handle 2002 contacting the end of the funnel 1606 or the coupling collar 2004 contacting the bottom inner surface of the funnel 1606), the tip of one or more of the rods 2008 abuts or contacts the end inner surface of the shaft 1602 at the exit aperture 1610.

In some embodiments, the crimp tube 2006 comprises a single channel such that all of the flexible rods 2008 fit within the single channel. Alternatively, the crimp tube 2006 is able to comprise a plurality is isolated channels such that each rod 2008 is able to be fixedly held in a separate channel. As shown in FIGS. 20A-C, the rods 2008 are able to offset within the crimp tube 2006 such that the tip of one of the rods 2008a extends further from the end of the crimp tube 2006 than the tip of the other of the rods 2008b. Specifically, this aids the rods in clearing out material stuck within the shaft 1602. Alternatively, the rods 2008 are able to be not offset within the crimp tube 2006, but have different lengths such that their tips are still offset. Alternatively, the tips of the rods 2008 are able to be not offset either via the rods 2008 themselves not being offset in the crimp tube 2006 (and the same length) or being offset in the crimp tube 2006 but having lengths such that the tips are still aligned (i.e. the portion of the rods 2008 extending out from the crimp tube 2006 is of an equal length).

Although as shown in FIGS. 20A-C, the plunger 2000 comprises two flexible rods 2008, more or less flexible rods 2008 are able to be used. In some embodiments, some or all of the flexible rods 2008 are coupled together lengthwise along the entire portion that they are adjacent (e.g. lengthwise) such that the rods 2008 must flex together at that portion. Alternatively, the rods 2008 are able to be formed as a single multi-rod. Alternatively, the rods 2008 are able to be uncoupled at some or all of the entire portion that the rods 2008 are adjacent. For example, the entirety of the portion of the rods 2008 that extend out from the crimp tube 2006 (e.g. the exposed portion) are able to be disconnected such that they are able to flex separately. In some embodiments, the flexible rods 2008 are made of nitinol. Alternatively, the flexible rods 2008 are able to be made of other flexible materials or combinations of other flexible materials and/or nitinol as are known in the art.

A method of operation of the bone fusion system 1500 according to some embodiments will now be discussed in conjunction with the flow chart shown in FIG. 21. In some embodiments, the method described in FIG. 21 is able to be combined with the method described in FIG. 14. The user slides the docking rod 1506 through the central hollow channel of the insertion instrument 802 and couples the tip 1704 of the docking rod 1506 into/with the positioning aperture 134 of the bone fusion device 1504 at the step 2102. The user spreads the fingers 903 by rotating the control sleeve 908 to the open or spread position thereby removing the fingers 903 from the gripping apertures 128 and out of the channels 122 at the step 2104. The user then removes the insertion instrument 802 from the patient leaving the docking rod 1506 coupled to the bone fusion device 1504 at the step 2106. The user couples the delivery member 1502 onto the docking rod 1506 until the exit aperture 1610 is aligned with one or more of the channels 120 of the device 1504 at the step 2108. In some embodiments, the coupling comprises sliding the docking rod 1506 through one or more of the coupling hoops 1612 and/or into the docking channel 1614. In some embodiments, the coupling comprises abutting the corner of an L-shape of the exit aperture 1610 with a side corner of the bone fusion device 1504 such that the L-shape is substantially aligned with the two sides of the device 1504 that meet to create the side corner.

The user prepares and inserts desired material into the cavity of the funnel 1606 of the delivery member 1502 at the step 2110. The user then pushes the material through the funnel 1606 and the shaft 1602 out the exit aperture 1610 and into the bone fusion device 1504 using one or more of the plungers 1508 at the step 2112. In some embodiments, when the use of the plungers 1508 comprises using the short rigid plunger 1800, this use is able to comprise coupling the short rigid plunger 1800 to the end of the funnel 1606 and turning the handle 1802 such that the head 1808 pushes further into the funnel 1606 (e.g. until all of the material has been pushed into the shaft 1602 or the head 1808 contacts the bottom of the funnel 1606). Alternatively, the coupling is able to be omitted. In some embodiments, when the use of the plungers 1508 comprises using the long rigid plunger 1900, this use is able to comprise coupling the long rigid plunger 1900 to the end of the funnel 1606 and turning the handle 1902 such that the head 1908 pushes further into the shaft 1602 (e.g. until all of the material has been pushed through the shaft 1602 and/or out of the exit aperture 1610 or the head 1908 contacts the bottom of the shaft 1602 defining the exit aperture 1610). Alternatively, the coupling is able to be omitted. In some embodiments, when the use of the plungers 1508 comprises using the flexible plunger 2000, this use is able to comprise sliding the plunger 2000 into and/or out of the shaft 1602 and/or the funnel 1606 in order to break up any stuck or blocking portion of the material. In some embodiments, the delivery member 1502 is able to be rotated 180 degrees about the docking rod 1502 such that the exit aperture 1610 aligns with a channel 120 on the opposite side of the device 1504 in order to provide material through both the first channel 120 and the other channel 120.

Once a desired amount of the material has been delivered to the device 1504, the user removes or decouples the delivery member 1502 and/or docking rod 1506 from the bone fusion device 1504 at the step 2114. In some embodiments, the user decouples the delivery member 1502 from the docking rod 1506 before decoupling the docking rod 1506 from the device 1504. Alternatively, the user decouples the docking rod 1506 from the device 1504 while the delivery member 1502 is still coupled to the docking rod 1506. In some embodiments, decoupling the delivery member 1502 from the docking rod 1506 comprises sliding the delivery member 1502 off the docking rod 1506 until the docking rod 1506 slides out of the docking channel 1614 and/or out of the coupling hoops 1612. As a result, the method provides the advantage of enabling desired material (e.g. bone graft material) to easily be delivered to the bone fusion device 1504 after it is already positioned within a patient and/or with the plates 130 already expanded to the desired height (which increased the empty volume within the body of the device 1504. In some embodiments, one or more of the steps of the methods 1300 and/or 2100 are able to be omitted. For example, if the measuring tool 1100 and/or the engaging tool 1200 are not desired the steps involving one or both of the tools are able to be omitted or performed without that aspect. As another example, if bone graft material is not necessary, the steps involving the packing of the bone graft material using the delivery apparatus 1502 is able to be omitted.

Removal/Repositioning Tools

Figure 22:
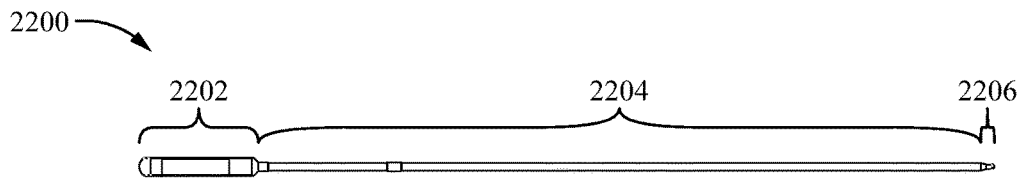
FIG. 22 illustrates a redocking tool according to some embodiments.

FIG. 22 illustrates a redocking tool 2200 according to some embodiments. As shown in FIG. 22, the redocking tool 2200 comprises base 2202 coupled to an elongated arm or rod 2204 having a redocking tip 2206. The elongated arm 2204 is able to be tubular and/or sized to slide and rotate within the central hollow channel of the insertion instrument 802 along the axis 900. The tip 2206 is able to be configured (e.g. contoured) to operably fit within or otherwise interface with the positioning aperture 134 of the device 804 such that when positioned within the aperture 134, rotation of the tip 2206 causes the positioning component 108 to correspondingly rotate. For example, the tip 2206 is able to have a hexagonal shape, a star-shape, a flat-head shape, a phillips head shape or other types of bit shapes as are known in the art. Alternatively, the tip 2206 is able to be shaped and/or couple to the positioning aperture 134 in the same manner as the tapered tip 1704 of the docking rod 1506. The length of the longest dimension of the redocking tool 2200 is able to be greater than the length of the longest dimension of the insertion instrument 802 such that when inserted into the central hollow channel the tool 2200 protrudes from one or both ends of the instrument 802. As a result, should an implanted device ever need to be removed or otherwise adjusted, the tip 2206 of the redocking tool 2200 is able to be coupled to the positioning aperture 134 of the device 804 and then the insertion instrument 802 slid down on the redocking tool 2200 thereby guiding the insertion instrument 802 to align with the device 804 in order to re-couple to the device 804 (as described above). In some embodiments, the redocking tool 2200 is slid into the insertion instrument 802 before the tip 2206 is coupled to the positioning aperture 134. Alternatively, the insertion instrument 802 is able to slid onto the redocking tool 2200 after the tip 2206 is coupled to the positioning aperture 134.

Figure 23:
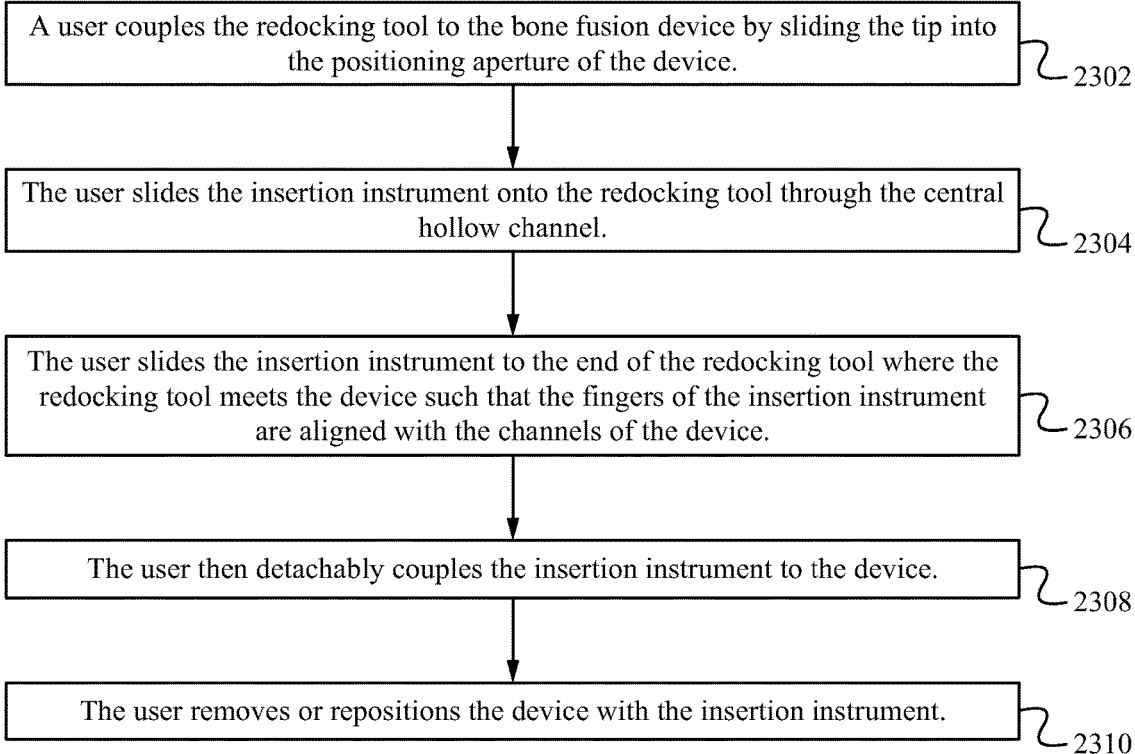
FIG. 23 illustrates a method of redocking with a bone fusion device according to some embodiments.

FIG. 23 illustrates a method of redocking with a bone fusion device according to some embodiments. As shown in FIG. 23, a user couples the redocking tool 2200 to the bone fusion device 804 by sliding the tip 2206 into the positioning aperture 134 of the device 804 at the step 2302. The user slides the insertion instrument 802 onto the redocking tool 2200 through the central hollow channel at the step 2304. Alternatively, the insertion instrument 802 is able to be slid onto the redocking tool 2200 before the redocking tool 2200 is coupled to the device 804. The user slides the insertion instrument 802 to the end of the redocking tool 2200 where the redocking tool 2200 meets the device 804 such that the fingers of the insertion instrument 802 are aligned with the channels 120 of the device 804 at the step 2306. The user then detachably couples the insertion instrument 802 to the device 804 at the step 2308. In some embodiments, the coupling of step 2208 is able to be substantially similar to steps 1406-1410 described above with reference to FIG. 14. The user removes or repositions the device 804 with the insertion instrument 802 at the step 2310. In some embodiments, the removal/repositioning comprises retracting the tabs/plates 130 using the engaging tool 1200 as described above. In such embodiments, the redocking tool 2200 is able to be removed from the central hollow channel to make room for the engaging tool 1200. Alternatively, the redocking tool 2200 is able to be rotated while coupled with the positioning aperture 134 in order to retract the tabs/plates 130. As a result, the method provides the advantage of enabling a device 804 to be removed or repositioned by safely guiding the insertion instrument 802 such that it is able to re-couple with the device 804.

Figure 24:
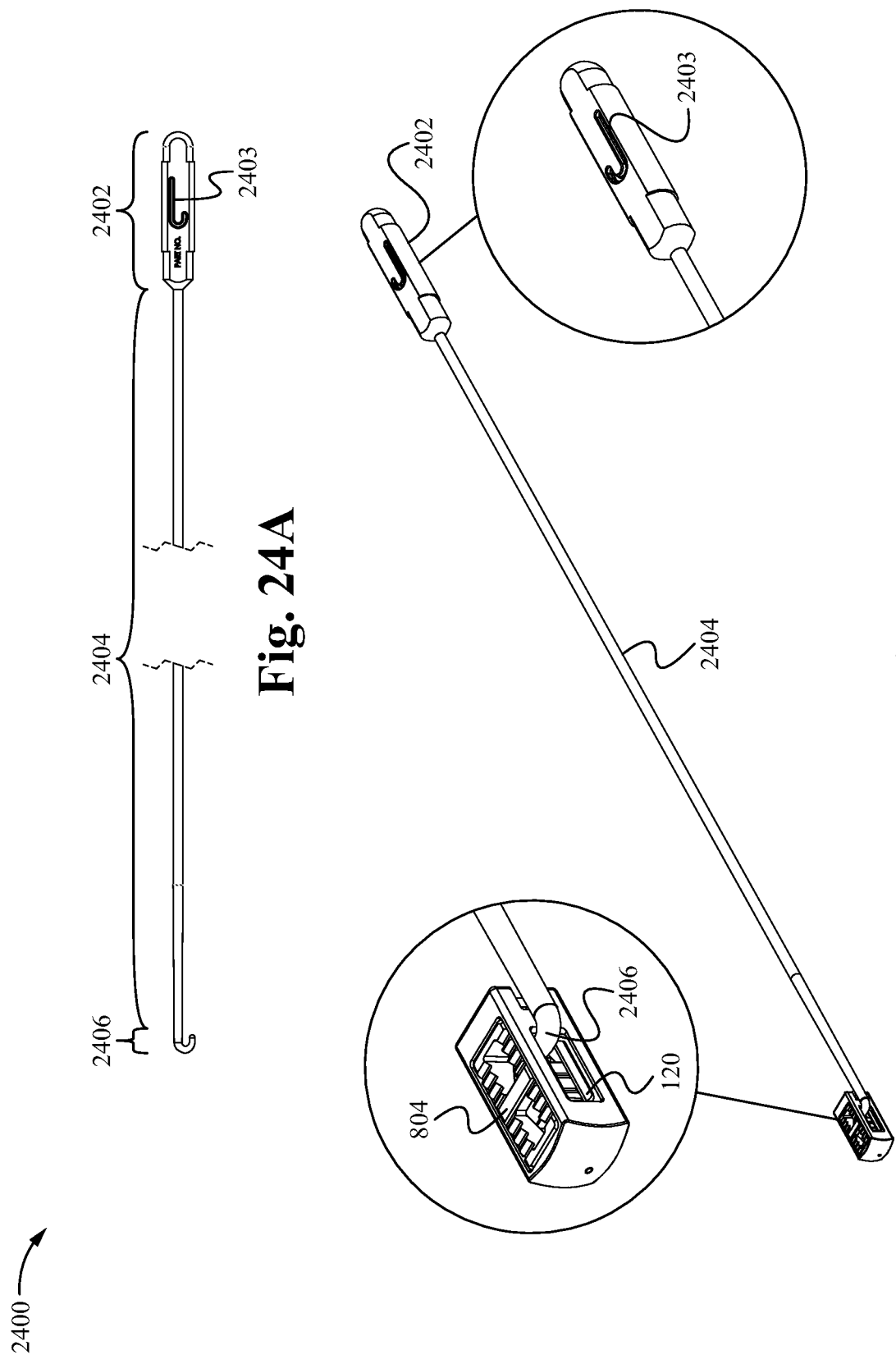
FIGS. 24A and 24B illustrate a rescue hook according to some embodiments.

FIGS. 24A and 24B illustrate a rescue hook 2400 according to some embodiments. As shown in FIG. 24A, the rescue hook 2400 comprises a base 2402 having a hook orientation indicator 2403 and coupled to an elongated arm or rod 2404 having a rescue hook 2406. The indicator 2403 is able to have an orientation that matches the rescue hook 2406 such that viewing the indicator 2403 is able to indicate the orientation of the rescue hook 2406. The elongated arm 2404 is able to be tubular. As shown in FIG. 24B, the hook 2406 is able to be sized such that the hooking portion is able to fit within one or more of the channels 120 of the device 804. In particular, the well created by the hook 2406 is able to be sized and/or contoured such that it is able to wrap around a side wall of the device 802 while being inserted into one of the channels 120 of the device 802 (thereby "hooking" the device 802). Alternatively, the hook 2406 is able to be inserted into any apertures on any sides of the device 802. As shown in FIG. 24, the well of the hook 2406 is rounded. Alternatively, the well of the hook 2406 is able to be squared (e.g. having two 90 degree turns) or otherwise be non-curved (e.g. coming to one or more concave points/edges) in order to form the U or hook shape. In some embodiments, the indicator 2403 is positioned on both sides of the base 2402. Alternatively, the indicator 2403 is able to be positioned on a single side of the base 2402. In some embodiments, two or more rescue hooks 2400 are able to be used simultaneously or concurrently to retrieve a device 802. For example, two hooks 2406 are able to be inserted into channels 120 on opposite sides of the device 802 at the same time to provide more stability in retrieving the device 802 with the rescue hooks 2400.

Figure 25:
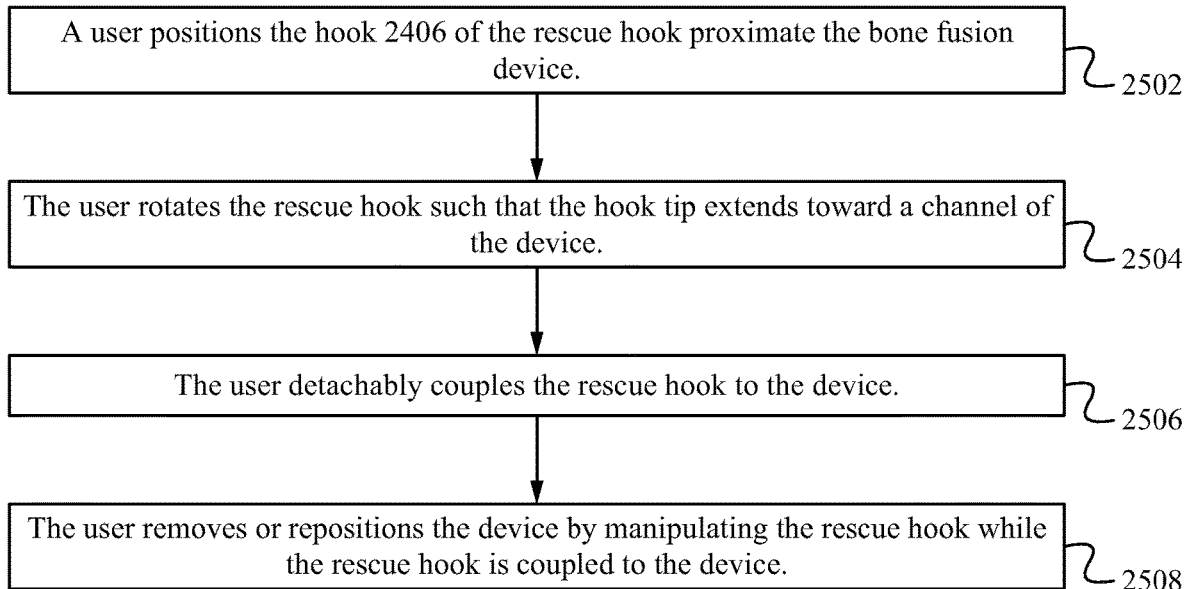
FIG. 25 illustrates a method of using a rescue hook according to some embodiments.

FIG. 25 illustrates a method of using a rescue hook 2400 according to some embodiments. As shown in FIG. 25, a user positions the hook 2406 of the rescue hook 2400 proximate the bone fusion device 804 at the step 2502. The user rotates the rescue hook 2400 such that the hook tip 2406 extends toward a channel 120 of the device 804 at the step 2504. In some embodiments, the user determines the orientation of the hook tip 2406 based on the indicator 2403 (e.g. the orientation of a hook marking of the indicator). The user detachably couples the rescue hook 2400 to the device 804 at the step 2506. In some embodiments, the coupling comprises inserting the rescue hook 2406 into the channel 120 of the bone fusion device 804. In some embodiments, the insertion comprises moving the hook 2400 such that a portion of the side wall of the device 804 defining the channel 120 slides into the well of the hook tip 2406. The user removes or repositions the device 804 by manipulating the rescue hook 2400 while the rescue hook 2400 is coupled to the device 804 at the step 2508. In some embodiments, step 2506 is able to be repeated with one or more additional hooks 2400 such that step 2508 is able to include the manipulating of each of the rescue hooks 2400 coupled to the device 804 in step 2506. Thus, the rescue hook 2400 provides the advantage of enabling a bone fusion device 804 to be removed or repositioned if necessary even if the device 804 cannot be re-docked with due to its position within the patient.

Additionally, it should be noted that although described separately from the insertion and measurement system and the material delivery system, the redocking tool 2200 and/or rescue hook 2400 are able to be a part of one or both of the systems. Similarly, although described separately from the insertion and measurement method and the material delivery method, the redocking tool method and/or rescue hook method are able to be combined with one or both of the methods.

Thus, the bone fusion device, apparatus and method described herein has numerous advantages. Specifically, the system and method provide the advantage of enabling the bone fusion device to be safely positioned and expanded using the insertion instrument. Further, they provide the advantage of enabling the precise measurement of the expansion level of the tabs of the bone fusion device using the measurement system. Moreover, they provide the advantage of enabling desired material to be safely delivered to the bone fusion device while positioned within a patent using the bone graft delivery apparatus and docking rod and in the desired quantity. They provide the advantage of enabling redocking with the device after in position using the redocking rod and/or recovering or moving a bone fusion device that cannot be accessed by the redocking rod using the rescue hook rod. Additionally, the fingers and fingertips coupled to the channels having gripping apertures ensure the non-slippage of the driving mechanism during the operation of the bone fusion apparatus. Also, as mentioned above, the method of use requires only a small incision and minimally invasive surgical procedure advantageously promoting health and rapid recovery by the patient. Indeed, bone growth occurs around the bone fusion device and particularly at the locations of the extended tabs, such that the bone fusion device is further secured by the bone growth, which further promotes a superior, robust bone fusion result. Additionally, the insertion instrument has a hollow central channel that enables the drive mechanism and/or a docking rod to be selectively removed or inserted into the positioning aperture as desired. Similarly, the hollow central channel of the delivery apparatus enables multiple different types of plungers to be used in concert to precisely deliver material to and/or within the bone fusion device.

The present invention has been described in terms of specific embodiments incorporating details to facilitate the understanding of principles of construction and operation of the invention. Such reference herein to specific embodiments and details thereof is not intended to limit the scope of the claims appended hereto. It will be apparent to those skilled in the art that modification may be made in the embodiments chosen for illustration without departing from the spirit and scope of the invention. For example, although the systems are described above separately, one or more components of two or more of the systems are able to be combined into a single system. Further, it should be noted that although the above bone fusion devices are described in reference to a pair of extending blocks, a pair of screws, and wherein each tab is shaped such that the ends are larger than the middle, and the size of the tab gradually increases while going from the middle to the ends, the use of a single extending block in the above embodiments is contemplated. Specifically, if using a single extending block, the above embodiments would operate the same except the positioning means would comprise a single screw that when engaged would cause the single extending block to move from one end of the screw to the other end thereby exerting a force against the tabs such that they move into the extended position. In such embodiments, each tab is shaped such that one end is larger than the opposite end, and the size of the tab gradually increases going from the smaller end to the larger end.

What is claimed is:

1. A bone fusion system for inserting a bone fusion device into a desired location, the system comprising:
    an engaging tool comprising a handle, an elongated member having a contoured tip and an interface gear, wherein the elongated member and the interface gear are both coupled to a base of the handle with the interface gear being centered around the elongated member; and
    a measuring tool comprising an indicating mechanism that indicates a variable tab extension value, wherein the indicating mechanism comprises an indicating screw, a screw gear coupled to the indicating screw, a ring threaded onto the indicating screw and an offset gear operably coupled to the screw gear such that rotation of the offset gear causes rotation of the indicating screw via the screw gear thereby causing the ring to move up or down the indicating screw, and further wherein the offset gear is detachably coupled with the interface gear of the engaging tool.

2. The system of claim 1, further comprising an insertion instrument comprising a first end, a second end opposite the first end, a coupling mechanism having a control shaft and a plurality of fingers configured to move between a closed position wherein the plurality of fingers are close together to a spread position wherein the plurality of fingers are farther apart based on manipulation of the control shaft.

3. The system of claim 2, wherein the control shaft has a hollow axial cavity that extends from the first end to the second end, and further wherein the engaging tool detachably couples with the insertion instrument by sliding into the hollow axial cavity such that the base of the handle is adjacent to the second end.

4. The system of claim 3, wherein the offset gear comprises a first set of teeth and a second set of teeth, wherein the first set of teeth are operably coupled with the screw gear and, when coupled to the insertion instrument, the interface gear of the engaging tool is operably coupled with the second set of teeth such that rotation of the engaging tool causes rotation of the offset gear via the interface gear.

5. The system of claim 4, further comprising a bone fusion device having a positioning screw, a body and one or more extendable tabs, wherein the body of the bone fusion device is detachably coupled to the first end of the insertion instrument by the coupling mechanism, wherein the positioning screw has a positioning aperture and operably coupled with the one or more extendable tabs such that rotation of the screw causes the one or more extendable tabs to extend from or retract into the body of the bone fusion device.

6. The system of claim 5, wherein, when the bone fusion device and the engaging tool are both coupled to the insertion instrument, the contoured tip of the engaging tool slides into the positioning aperture of the positioning screw such that rotation of the engaging tool causes the positioning screw to rotate thereby extending or retracting the one or more extendable tabs.

7. The system of claim 6, wherein the measuring tool couples to the insertion instrument by sliding the second end of the insertion instrument into a coupling aperture of the measuring tool and the engaging tool couples to the insertion instrument by sliding through the coupling aperture and the second end of the insertion instrument into the hollow axial cavity.

8. The system of claim 7, wherein the measuring tool further comprises a compatibility marker that indicates a type of bone fusion device whose tab extension or retraction rate is proportional to a distance the ring moves up or down the indicating screw when the indicating screw is rotated with the positioning screw by the engaging tool.

9. A method of operation of a bone fusion system, the method comprising:
providing a measuring tool comprising an indicating mechanism that indicates a variable tab extension value, wherein the indicating mechanism comprises an indicating screw, a screw gear coupled to the indicating screw, a ring threaded onto the indicating screw and an offset gear operably coupled to the screw gear;
detachably coupling an engaging tool to the offset gear of the measuring tool, the engaging tool comprising a handle, an elongated member having a contoured tip and an interface gear, wherein the elongated member and the interface gear are both coupled to a base of the handle with the interface gear being centered around the elongated member; and
turning the handle thereby rotating the offset gear which causes rotation of the indicating screw via the screw gear which moves the ring up or down the indicating screw.

10. The method of claim 9, further comprising:
providing an insertion instrument comprising a first end, a second end opposite the first end, a coupling mechanism having a control shaft and a plurality of fingers configured to move between a closed position wherein the plurality of fingers are close together to a spread position wherein the plurality of fingers are farther apart based on manipulation of the control shaft; and
detachably coupling the measuring tool and the engaging tool to the second end of the insertion instrument.

11. The method of claim 10, wherein the control shaft has a hollow axial cavity that extends from the first end to the second end.

12. The method of claim 11, wherein the offset gear comprises a first set of teeth and a second set of teeth, wherein the first set of teeth are operably coupled with the screw gear and, when coupled to the insertion instrument, the interface gear of the engaging tool is operably coupled with the second set of teeth such that rotation of the engaging tool causes rotation of the offset gear via the interface gear, wherein rotating the offset gear comprises rotating the handle of the engaging tool.

13. The method of claim 12, further comprising detachably coupling a bone fusion device to the first end of the insertion instrument using the coupling mechanism, wherein the bone fusion device comprises a body and one or more extendable tabs, wherein the bone fusion device comprises a positioning screw having a positioning aperture and operably coupled with the one or more extendable tabs such that rotation of the screw causes the one or more extendable tabs to extend from or retract into the body of the bone fusion device.

14. The method of claim 13, wherein coupling the engaging tool to the second end of the insertion instrument comprises sliding the contoured tip of the engaging tool into the positioning aperture of the positioning screw when the bone fusion device is coupled to the insertion instrument such that rotation of the engaging tool causes the positioning screw to rotate thereby extending or retracting the one or more extendable tabs.

15. The method of claim 14, wherein coupling the measuring tool to the insertion instrument comprises sliding the second end of the insertion instrument into a coupling aperture of the measuring tool, and wherein the engaging tool couples to the insertion instrument by sliding through the coupling aperture and the second end of the insertion instrument into the hollow axial cavity.

16. The method of claim 15, wherein the measuring tool further comprises a compatibility marker that indicates a type of bone fusion device whose tab extension or retraction rate is proportional to a distance the ring moves up or down the indicating screw when the indicating screw is rotated with the positioning screw by the engaging tool.

17. The method of claim 16, wherein the detachably coupling of the bone fusion device to the insertion instrument comprises:
spreading a plurality of fingers of an insertion instrument with a control shaft of the insertion instrument;
sliding the plurality of fingers of the insertion instrument into one or more surface channels of a bone fusion device;
contracting the plurality of fingers with the control shaft such that the plurality of fingers move into the surface channels and the insertion instrument is detachably coupled with the bone fusion device.

18. A measuring tool for use in a bone fusion device insertion system, the measuring tool comprising:
a screw that is able to rotate about a screw axis;

ring threaded onto the screw such that rotation of the screw causes the ring to move up or down the screw a distance along the screw axis;

a screw gear coupled to an end of the screw and centered around the screw axis such that rotation of the screw gear causes rotation of the screw; and an offset gear offset from the screw axis and operably coupled with the screw gear such that rotation of the offset gear causes the screw gear to correspondingly rotate about an offset axis, wherein the offset axis is non-perpendicular to the screw axis, and further wherein a number of rotations of the screw gear in a direction is proportional to the distance moved by the ring caused by the rotation of the screw gear.

19. The tool of claim 18, further comprising a housing including a gear chamber and a screw chamber, wherein the gear chamber comprises a coupling aperture that extends through the gear chamber in a direction and is non-circular in a plane orthogonal to that direction.

20. The tool of claim 19, wherein the offset gear has a gear aperture that extends through the offset gear and aligns with the coupling aperture.

21. The tool of claim 20, wherein the offset gear comprises a first set of teeth and a second set of teeth, wherein the first set of teeth are operably coupled with the screw gear and the second set of teeth are accessible from outside the gear chamber via the coupling aperture.

22. The tool of claim 21, wherein the screw chamber comprises a viewing aperture that extends along a length of the screw such that the length of the screw and the ring are visible from outside the screw chamber via the viewing aperture.

23. The tool of claim 22, wherein the ring at least partially protrudes into the viewing aperture such that the inner walls of the screw chamber defining the viewing aperture prevent the ring from rotating with the screw when the screw rotates within the screw chamber.

24. The tool of claim 23, wherein the housing comprises a plurality of height lines positioned on an outer surface of the housing along the perimeter of the viewing aperture, wherein the height lines are all orthogonal to the screw axis within the screw chamber.

25. The tool of claim 24, wherein the outer surface of the housing further comprises a compatibility marker that indicates a type of a bone fusion device whose tab extension or retraction rate is proportional to a distance the ring moves up or down the screw when the screw is rotated.

26. An engaging tool for use in a bone fusion device insertion system, the engaging tool comprising:

a handle having a base;

an elongated member having a first end and a second end opposite the first end and coupled with the base of the handle, wherein the elongated member is longer than the handle; and an interface gear having a set of teeth and coupled with the base of the handle such that the set of teeth are centered around and surround a portion of the elongated member but are separated from and do not contact the elongated member, wherein the first end of the elongated member extends away from the base of the handle beyond the interface gear, and further wherein the handle and the second end of the elongated member are operably coupled with the interface gear such that rotation of the handle causes the elongated member and the interface gear to rotate together.

27. The tool of claim 26, wherein the elongated member has a central axis and a contoured tip that is non-circular in a plane orthogonal to the central axis.

28. The tool of claim 27, wherein the set of teeth protrude away from the base of the handle.

\* \* \* \* \*